US011505612B2

(12) United States Patent
Liu et al.

(10) Patent No.: US 11,505,612 B2
(45) Date of Patent: *Nov. 22, 2022

(54) METHOD OF TREATING DISEASES USING AN IL-17 RECEPTOR ANTIBODY FORMULATION

(71) Applicant: Amgen K-A, Inc., Thousand Oaks, CA (US)

(72) Inventors: Dingjiang Liu, Oak Park, CA (US); Holly Zhuohong Huang, Thousand Oaks, CA (US); David Andrew Martin, Seattle, WA (US); Christopher Boyd Russell, Bainbridge Island, WA (US); David H. Salinger, Seattle, WA (US); Scott Walter Baumgartner, Thousand Oaks, CA (US); Christopher Endres, Seattle, WA (US)

(73) Assignee: AMGEN K-A, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/015,029

(22) Filed: Sep. 8, 2020

(65) Prior Publication Data

US 2020/0399384 A1  Dec. 24, 2020

Related U.S. Application Data

(60) Continuation of application No. 16/053,564, filed on Aug. 2, 2018, now Pat. No. 10,808,033, which is a continuation of application No. 14/499,691, filed on Sep. 29, 2014, now Pat. No. 10,072,085, which is a division of application No. 13/521,999, filed as application No. PCT/US2011/020985 on Jan. 12, 2011, now Pat. No. 8,883,151.

(60) Provisional application No. 61/422,059, filed on Dec. 10, 2010, provisional application No. 61/295,387, filed on Jan. 15, 2010.

(51) Int. Cl.
*A61K 39/395* (2006.01)
*C07K 16/28* (2006.01)
*A61K 39/00* (2006.01)

(52) U.S. Cl.
CPC .... *C07K 16/2866* (2013.01); *A61K 39/39591* (2013.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/76* (2013.01)

(58) Field of Classification Search
CPC .......... C07K 16/2866; C07K 2317/565; C07K 2317/76; A61K 2039/505
See application file for complete search history.

(56) References Cited

U.S. PATENT DOCUMENTS

| | | |
|---|---|---|
| 4,946,778 A | 8/1990 | Ladner et al. |
| 5,116,964 A | 5/1992 | Capon et al. |
| 5,136,021 A | 8/1992 | Dembinski et al. |
| 5,530,101 A | 6/1996 | Queen et al. |
| 5,703,088 A | 12/1997 | Sharpe et al. |
| 5,716,805 A | 2/1998 | Srinivasan et al. |
| 5,869,286 A | 2/1999 | Yao et al. |
| 6,043,344 A | 3/2000 | Jacobs et al. |
| 6,072,033 A | 6/2000 | Yao et al. |
| 6,072,037 A | 6/2000 | Yao et al. |
| 6,083,906 A | 7/2000 | Troutt |
| 6,096,305 A | 8/2000 | Yao et al. |
| 6,100,235 A | 8/2000 | Yao et al. |
| 6,114,598 A | 9/2000 | Kucherlapati et al. |
| 6,162,963 A | 12/2000 | Kucherlapati et al. |
| 6,171,586 B1 | 1/2001 | Lam et al. |
| 6,191,104 B1 | 2/2001 | Spriggs et al. |
| 6,197,525 B1 | 3/2001 | Yao et al. |
| 6,406,867 B1 | 6/2002 | Yu et al. |
| 6,680,057 B1 | 1/2004 | Yao et al. |
| 6,793,919 B2 | 9/2004 | Mohler |
| 6,833,268 B1 | 12/2004 | Green et al. |
| 7,049,426 B2 | 5/2006 | Green et al. |
| 7,064,244 B2 | 6/2006 | Jakobovits et al. |
| 7,273,843 B2 | 9/2007 | Yao et al. |
| 7,432,237 B2 | 10/2008 | Yao et al. |
| 7,767,206 B2 | 8/2010 | Tocker et al. |
| 7,786,284 B2 | 8/2010 | Tocker et al. |
| 7,833,527 B2 | 11/2010 | Tocker et al. |
| 7,939,070 B2 | 5/2011 | Tocker et al. |
| 8,435,518 B2 | 5/2013 | Tocker |
| 8,883,151 B2 | 11/2014 | Liu et al. |
| 2003/0180255 A1 | 9/2003 | Goddard et al. |
| 2005/0013814 A1 | 1/2005 | Mohler |
| 2006/0275306 A1 | 12/2006 | Andya et al. |
| 2007/0129302 A1 | 6/2007 | Gao et al. |

(Continued)

FOREIGN PATENT DOCUMENTS

| | | |
|---|---|---|
| EP | 0308378 | 3/1989 |
| EP | 0315062 | 5/1989 |

(Continued)

OTHER PUBLICATIONS

"Monoclonal anti-human IL-17 R antibody," <http://www.rndsystems.com> R&D Systems, 2004.

(Continued)

*Primary Examiner* — Dong Jiang

(74) *Attorney, Agent, or Firm* — Casimir Jones SC; Lisa Mueller

(57) ABSTRACT

The present disclosure relates to AM-14 pharmaceutical formulations and therapeutic dosing regimens for the treatment of disease.

6 Claims, 10 Drawing Sheets

Specification includes a Sequence Listing.

(56) References Cited

U.S. PATENT DOCUMENTS

| | | |
|---|---|---|
| 2007/0134199 A1 | 6/2007 | Frevert |
| 2008/0213282 A1 | 9/2008 | Jacob et al. |
| 2008/0219979 A1 | 9/2008 | Tocker et al. |
| 2008/0220479 A1 | 9/2008 | Tocker et al. |
| 2008/0221307 A1 | 9/2008 | Tocker et al. |
| 2009/0068737 A1 | 3/2009 | Yao et al. |
| 2009/0074758 A1 | 3/2009 | Tocker et al. |
| 2009/0130122 A1 | 5/2009 | Mohler |
| 2009/0274703 A1 | 11/2009 | Mohler |
| 2009/0291076 A1 | 11/2009 | Morichika et al. |
| 2010/0028345 A1 | 2/2010 | Tocker et al. |
| 2010/0233186 A1 | 9/2010 | Yao et al. |
| 2010/0278840 A1 | 11/2010 | Mohler |
| 2010/0292442 A1 | 11/2010 | Tocker et al. |
| 2011/0008356 A1 | 1/2011 | Peschon et al. |
| 2011/0008841 A1 | 1/2011 | Tocker et al. |
| 2011/0052600 A1 | 3/2011 | Budelsky et al. |
| 2011/0081339 A1 | 4/2011 | Tocker et al. |
| 2011/0166331 A1 | 7/2011 | Tocker et al. |
| 2012/0201821 A1 | 8/2012 | Gonzalez et al. |
| 2012/0251547 A1 | 10/2012 | Tocker et al. |
| 2012/0308566 A1 | 12/2012 | Martin et al. |
| 2013/0004969 A1 | 1/2013 | Peschon et al. |
| 2014/0234330 A1 | 8/2014 | Budelsky et al. |
| 2014/0322238 A1 | 10/2014 | Budelsky et al. |
| 2014/0356355 A1 | 12/2014 | Tocker et al. |
| 2016/0208004 A1 | 7/2016 | Budelsky et al. |

FOREIGN PATENT DOCUMENTS

| | | |
|---|---|---|
| EP | 0393438 | 10/1990 |
| EP | 0398327 | 11/1990 |
| EP | 0412486 | 2/1991 |
| EP | 0417563 | 3/1991 |
| EP | 0418014 | 3/1991 |
| EP | 0422339 | 4/1991 |
| EP | 0433900 | 6/1991 |
| EP | 0464533 | 1/1992 |
| EP | 0512528 | 11/1992 |
| EP | 0526905 | 2/1993 |
| EP | 0568928 | 11/1993 |
| EP | 1977763 | 10/2008 |
| FR | 2910324 | 6/2008 |
| GB | 2218101 | 11/1989 |
| GB | 2243569 | 11/1991 |
| JP | 1991-127800 | 5/1991 |
| WO | WO 198909622 | 10/1989 |
| WO | WO 199013575 | 11/1990 |
| WO | WO 199103553 | 3/1991 |
| WO | WO 199116437 | 10/1991 |
| WO | WO 199201002 | 1/1992 |
| WO | WO 199211018 | 7/1992 |
| WO | WO 199213095 | 8/1992 |
| WO | WO 199216221 | 10/1992 |
| WO | WO 199307863 | 4/1993 |
| WO | WO 199311161 | 6/1993 |
| WO | WO 199321946 | 11/1993 |
| WO | WO 199406476 | 3/1994 |
| WO | WO 199413804 | 6/1994 |
| WO | WO 199518826 | 7/1995 |
| WO | WO 199534326 | 12/1995 |
| WO | WO 199629408 | 9/1996 |
| WO | WO 199704097 | 2/1997 |
| WO | WO 199801555 | 1/1998 |
| WO | WO 199823284 | 6/1998 |
| WO | WO 199914240 | 3/1999 |
| WO | WO 199960127 | 11/1999 |
| WO | WO 200015759 | 3/2000 |
| WO | WO 200055204 | 9/2000 |
| WO | WO 2001024814 | 4/2001 |
| WO | WO 200168705 | 9/2001 |
| WO | WO 200168859 | 9/2001 |
| WO | WO 2002058717 | 8/2002 |
| WO | WO 2003072060 | 9/2003 |
| WO | WO 2004002519 | 1/2004 |
| WO | WO 2004003019 | 1/2004 |
| WO | WO 2005016275 | 2/2005 |
| WO | WO 2005063290 | 7/2005 |
| WO | WO 2005063291 | 7/2005 |
| WO | WO 2006054059 | 5/2006 |
| WO | WO 2006088925 | 8/2006 |
| WO | WO 2006138181 | 12/2006 |
| WO | WO 2007019232 | 2/2007 |
| WO | WO 2007027761 | 3/2007 |
| WO | WO 2007037795 | 4/2007 |
| WO | WO 2007053533 | 5/2007 |
| WO | WO 2007092772 | 8/2007 |
| WO | WO 2008049070 | 4/2008 |
| WO | WO 2008054603 | 5/2008 |
| WO | WO 2008079290 | 7/2008 |
| WO | WO 2008084237 | 7/2008 |
| WO | WO 2008118930 | 10/2008 |
| WO | WO 2008156709 | 12/2008 |
| WO | WO 2009006301 | 1/2009 |
| WO | WO 2009026122 | 2/2009 |
| WO | WO 2009136976 | 11/2009 |
| WO | WO 2011046958 | 4/2011 |
| WO | WO 2011088120 | 7/2011 |
| WO | WO 2012045848 | 4/2012 |
| WO | WO 2012061129 | 5/2012 |
| WO | WO 2013016220 | 1/2013 |
| WO | WO 2015153144 | 10/2015 |
| WO | WO 2016031250 | 3/2016 |

OTHER PUBLICATIONS

Aarvak et al., "Analysis of IL-17 and other cytokines and surface makers of RA inflammatory T cell clones," American College of Rheumatology (ACR) meeting, Poster 1448, Nov. 1997.

Aarvak et al., "IL-17 is produced by some proinflammatory Th1/Th0 cells but not by Th2 Cells," J. Immunol. 162:1246-1251, 1999.

Aggarwal, S. and Gurney, A., "IL-17: prototype member of an emerging cytokine family," J. Leukocyte Biol, 71:1-8, 2002.

Albanesi et al., "IL-17 is produced by nickel-specific T lymphocytes and regulates ICAM-1 expression and chemokine production in human keratinocytes: Synergistic or antagonist effects with IFN-γ and TNF-α," J. Immunol., 162:494-502, 1999.

Albrecht et al., "Primary structure of the herpesvirus saimiri genome," J. Virol., 66(8):5047-5058, 1992.

Amin, A. R. et al., "The expression and regulation of nitric oxide synthase in human osteoarthritis-affected chondrocytes: Evidence for up-regulated neuronal nitric oxide synthase," J. Exp. Med., 182:2097-2102, Dec. 1995.

Ankarcrona, M. et al., "Interleukin-1 β-induced nitric oxide production activates apoptosis in pancreatic RINm5F cells," Exp Cell Rsh, 213:172-177, 1994.

Anonymous, Study to evaluate the safety, tolerability, and efficacy of AMG 827 in subjects with psoriasis, <<<http://clinicaltrials.aov/ct2/show/NCT00975637>>>, dated Sep. 10, 2009.

Arend, W. et al., "Inhibition of the production and effects of interleukin-1 and tumor necrosis factor α in the rheumatoid arthritis," Arthritis & Rhem., 38(2):151-160, 1995.

Attur, M. G. et al., "Interleukin-17 up-regulation of nitric oxide production in human osteoarthritis cartilage," Arthritis & Rheum., 40(6):1050-1053, 1997.

Ballantyne et al., "Blocking IL-25 prevents airway hyperresponsiveness in allergic asthma," J Allergy Clin Immunol, 2007, 120(6):1324-31.

Baragi, V. M. et al., "Transplantation of transduced chondrocytes protects articular cartilage from interleukin 1-induced extracellular matrix degradation," J. Clin. Invest., 96(5):2454-2460, 1995.

Barker et al., "p75NTR is positively promiscuous: novel partners and new insights," Neuron, 42:529-33 (2004).

Bird et al., "Single-chain antigen-binding proteins," Science 242:423-426, 1988.

Bowie et al., "Deciphering the message in protein sequences: Tolerence to amino acid substitutions," Science, 47:1306-1310, 1990.

(56) References Cited

OTHER PUBLICATIONS

Brorson, K. et al., "Mutational analysis of avidity and fine specificity of anti-levan antibodies," J. Immunol., 163:6694-6701, 1999.
Brummell, DA et al., "Probing the combining site of an anti-carbohydrate antibody by saturation-mutagenesis: role of the heavy-chain CDR3 residues," Biochem., 32:1180-1187, 1993.
Burks, E. et al., "In vitro scanning saturation mutagenesis of an antibody biding pocket," Proc. Tatl. Acad. Sci. USA, 94:412-417, 1997.
Busse et al., "Randomized, Double-Blind, Placebo-controlled Study of Brodalumab, a Human Anti-IL-17 Receptor Monoclonal Antibody, in Moderate to Severe Asthma," Am J Respir Crit Care Med, 2013, 188(11):1294-1302.
Cannetti et al., "IL-18 enhances collagen-induced arthritis by recruiting neutrophils via TNF-α and leukotriene B4," J Immunol, 171:1009-1015, 2003.
Caron, J. P. et al., "Chondroprotective effect of intraarticular injections of interleukin-1 receptor antagonist in experimental osteoarthritis," Arthritis & Rheum., 39(9):1535-1544, 1996.
Casset et al., "A peptide mimetic of an anti-CD4 monoclonal antibody by rational design," BBRC 307, 2003, 198-205.
Chabaud et al., "The combination of tumor necrosis factor a blockade with interleukin-1 and interleukin-17 blockade is more effective for controlling synovial inflammation and bone resorption in an ex vivo model," Arthritis Rheum, 44(6):1293-1303 (2001).
Chabaud, M. et al., "Contributionof interleukin 17 to synovium matrix destruction in rheumatoid arthritis," Cytokine, 12(7):1092-1099, 2000.
Chabaud, M. et al., "Enhancing effect of IL-17 on IL-1-Induced IL-6 and leukemia inhibitory factor production by rheumatoid arthritis synoviocytes and its regulation by Th2 cytokines," J. Immunol., 161:409-414, 1998.
Chabaud, M. et al., "Regulation of the effects of IL 17 on IL 6 and LIF production by RA synoviocytes," American College of Rheumatology (ACR) meeting, Poster 1449, Nov. 1997.
Chang et al., "Interleukin-17C Promotes Th17 Cell Responses and Autoimmune Disease via Interleukin-17 Receptor E," Immunity, vol. 35, vol. 4, pp. 611-621, (2011).
Charles et al., "Regulation of cytokines, cytokine inhibitors, and acute-phase proteins following anti-TNF-α therapy in rheumatoid arthritis," J Immunol, 163:1521-1528, 1999.
Chen et al., "Selection and Analysis of an Optimized Anti-VEGF Antibody: Crystal Structure of an Affinity-matured Fab in Complex with Antigen," J. Mol. Bio. 293, 1999, 865-881.
Clinicaltrials.gov, <https://clinicaltrials.gov/archive/NCT02052609/2014_01_13> (Oct. 16, 2014, pp. 12, search for brodalumab).
Coleman, P. M., "Effects of amino acid sequence changes on atibody-antigen interactions," Res. Immunol., 145:33-36, 1994.
Crystal, R., "Transfer of genes to humans: Early lessons and obstacles to success," Sci., 270:404-410, 1995.
Cua et al., "Innate IL-17-producing cells: the sentinels of the immune system," Nat Rev Immunol., 2010, 10:479-489.
Daugherty et al., "Formulation and delivery issues for monoclonal antibody therapeutics." Adv. Drug Deliv. Rev., 58(5-6): 686-706 (2006).
Davies et al., "Affinity improvement of single antibody VH domains: residues in all three hypervariable regions affect antigen binding," Immunotechnology, vol. 2, No. 3, pp. 169-179, 1996.
De Graaf et al., "Expression of scFvs and scFv fusion proteins in eukaryotic cells," Methods Mol Biol. 178:379-87, 2002.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, 2002, 169, 3076-3084.
Deonarain, M. "Ligand-targeted receptor-mediated vectors fo gene delivery," Exp. Opin. Ther. Patents, vol. 8:53-69, 1998.
Dogra et al., "Biologic therapy in psoriasis," Indian J. Dermatol. Venereol. Leprol., 72(4):256-265, 2006.
Dudler et al., "In vivo effects of murine recombinant interleukin-17 on synovial joint in mice," American College of Rheumatology (ACR) meeting, Poster 1450, Nov. 1997.
Dufner, P. et al., "Harnessing phage and ribosome display for antibody optimization," Trends Biotechnol., 24(11):523-529, 2006.
Fanslow et al., "Regulation of alloreactivity I vivo IL-4 and the soluble IL-4 receptor," J. Immunol., 47(2):535-540, 1991.
Fanslow et al., "Regulation of alloreactivity in vivo by a soluble form of the interleukin-1 receptor," Science, 248:739-742, 1990.
Fort et al., "IL-25 Induces IL-4, IL-5, and IL-13 and Th2-Associated Pathologies In Vivo," Immunity, 2001, 15:985-995.
Fossiez et al., "T cell interleukin-17 induces stromal cells to produce proinflammatory and hematopoietic cytokines," J. Exp. Med., 183:2593-2603, 1996.
Fouilhoux et al., "Production of IL-17 and its regulation in rheumatoid synovium," American College of Rheumatology (ACR) meeting, Poster 1447, 1997.
Frömmel, C. and Holzhütter, H. G., "An estimate on the effect of point mutation and natural selection on the rate of amino acid replacement in proteins," J. Mol. Evol., 21:233-257, 1985.
Fujino et al., "Increased expression of interleukin 17 in inflammatory bowel disease.," Gut, 52: 65-70 (2003).
Gaffen et al., "The IL-17 cytokine family, Vitamins and Hormones," Academic Press, New York, NY, US, 255-82 (2006).
Gaffen, "Structure and signalling in the IL-17 receptor family." Nat Rev Immunol., 9(8): 556-68 (2009).
GenBank Accession No. H55639 (1995).
GenBank Accession No. MMU31993 (1996).
GenBank Accession No. NM_014339 (2014).
GenBank Accession No. NM_018725 (2014).
Green et al., "Antigen-specific human monoclonal antibodies from mice engineered with huma Ig heavy and light chain YACs," Nat Genet, 7:13-21, 1994.
Green et al., "Regulation of B cell development by variable gene complexity in mice reconstituted with human immunoglobulin yeast artificial chromosomes," J Exp Med, 188(3):483-495, 1998.
Harrington et al., "Interleukin 17-producing CD4+ effector T cells develop via lineage distinct from the T helper type 1 and 2 lineages," Nat. Immunol., 6(11):1123-32 (2005).
Haudenschild et al., "Soluble and transmembrane isoforms of novel interleukin-17 receptor-like protein by RNA splicing and expression in prostate cancer," Journal of Biological Chemistry, vol. 277, No. 6, pp. 4309-4316, 2002.
Hermanns-Le et al., "Ustekinumab in Psoriasis Immunopathology with Emphasis on the Th17-IL23 Axis: A Primer," J. Biomed. Biotech. 2012: 1-6, 2012.
Holliger et al., "Diabodies: small bivalent and bispecific antibody fragments," Proc. Natl. Acad. Sci. U.S.A. 90:6444-6448, 1993.
Holliger et al., "Engineering bispecific antibodies," Current Opinion Biotechnol, 1993, vol. 4, Issue 4, pp. 446-449.
Holm et al., "Functional mapping and single chain construction of the anti-cytokeratin 8 monoclonal antibody TS1," Mol. Immunol. 2007, 44:1075-1084.
Holt et al., "Domain antibodies: proteins for therapy," Trends in Biotechnology, vol. 21, No. 11, pp. 484-490, (2003).
Honorati et al., "IL-17 enhances the susceptibility of U-2 OS osteosarcoma cells to NK cell lysis," Clinical and Experimental Immunology Sep. 2003, vol. 133, No. 3, pp. 344-349, 2003.
Hu et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res. 56:3055-3061, 1996.
Huston et al., "Protein engineering of antibody binding sites: Recovery of specific activity in an anti-digoxin single-chain Fv analogue produced in *Escherichia coli*," Proc. Natl. Acad. Sci. U.S.A. 85:5879-5883, 1988.
Hwang et al., "Expression of IL-17 homologs and their receptors in the synovial cells of rheumatoid arthritis patients," Mol. Cells, 19(2):180-4 (2005).
Hymowitz et al., "IL-17s adopt a cystine knot fold fold: structure and activity of a novel cytokine, IL-17F, and implications for receptor biding," EMBO J., 20:5332-41 (2001).

(56) References Cited

OTHER PUBLICATIONS

Infante-Duarte et al., "Microbial lipopeptides induce the production of IL-17 in the Th cells, J. Immunol.," 65:6107-15 (2000).
International Preliminary Examination Report for Application No. PCT/US2001/049504 dated Apr. 24, 2003 (7 pages).
International Preliminary Report on Patentability for Application No. PCT/US2007/021174 dated Apr. 7, 2009 (12 pages).
International Preliminary Report on Patentability for Application No. PCT/US2008/007460 dated Dec. 17, 2009 (7 pages).
International Preliminary Report on Patentability for Application No. PCT/US2011/020985 dated Jul. 17, 2012 (7 pages).
International Search Report and Written Opinion for Application No. PCT/JP2015/004306 dated Oct. 13, 2015 (10 pages).
International Search Report and Written Opinion for Application No. PCT/US2009/001085 dated Feb. 17, 2010 (10 pages).
International Search Report and Written Opinion for Application No. PCT/US2010/052366 dated Dec. 23, 2010 (22 pages).
International Search Report and Written Opinion for Application No. PCT/US2012/047677 dated Oct. 18, 2012 (20 pages).
Jang, Y. J. et al., "The structural basis for DNA biding by an anti-DNA autoantibody," Mol. Immunol., 35:1207-1217, 1998.
Jia et al., "A novel method of multiplexed competitive antibody binning for the characterization of monoclonal antibodies," J Immunol Methods, 288:91-98, 2004.
Jones, "Replacing the complementarity-determining regions in a human antibody with those from a mouse," Nature 321:522-525, 1986.
Joosten et al., "IL-1αβ Blockade Prevents Cartilage and Bone Destruction in Murine Type II Collagen-Induced Arthritis, Whereas TNF-α Blockade Only Ameliorates Joint Inflammation," J. Immunol., 163:5049-5055, 1999.
Jovanovic et al., "IL-17 stimulates the production and expresion of proinflammatory cytokines, IL-13 and TNF-a, by human macrophages," J. Immunol., 160:3513-21 (1998).
Jovanovic et al., "IL-17 stimulates the secretion of proinflammatory cytokines by human macrophages," American College of Rheumatology (ACR) meeting, Poster 1446, Nov. 1997.
Jovanovic et al., "Stimulation of 92-kd gelatinase (matrix metalloproteinase 9) production by interleukin-17 in human monocyte/macrophanges," Arthritis & Rheum., 43(5):1134-44 (2000).
Kamerzell et al., "Increasing IgG Concentration Modulates the Conformational Heterogeneity and Bonding Network that Influence Solution Properties," J. Phys. Chern., 113:6109-18 (2009).
Kauffman et al., "A phase I study evaluating the safety, pharmacokinetics, and clinical response of a human IL-12 p40 antibody in subjects with plaque psoriasis." J.Invest. Dermatol., 123: 1037-44 (2004).
Kawaguchi et al., "IL-17 cytokine family," J. Allergy Clin. Immunol., 114:1265 (2004).
Kawaguchi M et al: "Identification of a novel cytokine, ML-1, and its expression in subjects with asthma." Journal of Immunology, 2001, vol. 167, No. 8, pp. 4430-4435.
Kimura et al., "IL-6-dependent and independent pathways in the development of interleukin 17-producing T helper cells," Proc Natl Acad Sci, USA, 104(29):12099-12104, 2007.
Kircik and Kumar, "Scalp psoriasis," J. Drugs Dermolog. 9:s101-s102, 2010.
Kobayashi, H. et al., "Tryptophan H33 plays an important role in pyrimidine (6-4) pyrimidine photoproduct binding by hign-affinity antibody," Protein Eng., 12:879-884, 1999.
Kolls et al., "Interleukin-17 family members and inflammation." Immunity, 21:467-76 (2004).
Konishi et al., "IL-18 contributes to the spontaneous development of atopic dermatitis-like inflammatory skin lesion independently of IgE/stat6 under specific pathogen-free conditions," Proc Natl Acad Sci, USA, 99(17):11340-11345, 2002.
Kortt et al., "Dimeric and trimeric antibodies: high avidity scFvs for cancer targeting," Biomol. Eng. 18:95-108, 2001.
Kortt et al., "Single-chain Fv fragments of anti-neuraminidase antibody NC10 containing five- and ten-residue linkers form dimers and with zero-residue linker a trimer," Prot. Eng. 10(4):423, 1997.
Kotake, S., "IL-17 in synovial fluids from patients with rheumatoid arthritis is a potent stimulator of osteoclastogenesis," J. Clin. Invest., 103(9):1345-1352, 1999.
Kriangkum et al., "Bispecific and bifunctional single chain recombinant antibodies," Biomol. Eng. 18(2):31-40, 2001.
Kuestner et al., "Identification of the IL-17 receptor-related molecle, IL-17RC as a receptor for IL17A and IL-17F," J Immunol. Oct. 15, 2007;179(8):5462-73.
Kumar, S. et al., "Molecular cloning and expressing of the Fabs of human autoantibodies in *Escherichia coli*," J. Biol. Chem., 275(45):35129-35136, 2000.
Kurasawa et al., "Increased interleukin-17 production in patients with systemic sclerosis," Arthritis & Rheum., 43(11):2455-63 (2000).
Langrish et al., "IL-23 drives a pathogenic T cell population that induces autoimmune inflammation," J Exp Med, 201(2):233-240 (2005).
Lee et al., "IL-18 E42A mutant is resistant to the inhibitory effects of HPV-16 E6 and E7 oncogenes on the IL-18-mediated immune response," Cancer Lett., 229:261-270, 2005.
Leonardi et al., "Anti-Interleukin-17 Monoclonal Antibody Ixekizumab in Chronic Plaque Psoriasis," New England Journal of Medicine, vol. 366, No. 13, pp. 1190-1199, 2012.
Li et al., "Cloning and characterization of IL-17B and IL-17C, two new members of the IL-17 cytokine family," Proc. Natl. Acad. Sci. USA, 97(2):773-8 (2000).
Liew, "Nitric oxide in infectious and autoimmune diseases," CIBA Foundation Symposium, 195:234-244, 1995.
Linden et al., "Airway neutrophils and interleukin-17." Eur. Respir. J., 15(5): 973-7 (2000).
Littman et al., "Th17 and regulatory T cells in mediating and restraining inflammation," Cell, 2010, 140(6):845-58.
Livingston et al., "Identification and Characterization of Synthetic Small Molecule Macrocycle Antagonists of Human IL17A," ACR Annual Meeting, Nov. 9-14, 2012.
Li et al., "The expression of interleukin-17, interferon-gamma, and macrophage inflammatory protein-3 alpha mRNA in patients with psoriasis vulgaris." Huazhong Univ. Sci. Technolog. Med. Sci. 24: 294-6 (2004).
Lotz et al., "IL-17 promotes cartilage degradation, Arthritis and Rheum.," 39 suppl. (9):S120 (1996).
Lu et al., "The yin and yang of neurotrophin action," Nat. Rev. Immunol., 6:603-14 (2005).
Lubberts et al., "IL-17 promotes bone erosion in murine collagen-induced arthritis through loss of the receptor activator of NF-x13 ligand/osteoprotegerin balance," J. Immunol, 170:2655-62 (2003).
Lubberts et al., "IL-1-independent role of IL-17 in synovial inflamation and joint destruction during collagen-induced arthritis," J. Immunol, 167:1004-13 (2001).
Lubberts et al., "The role of T cell interleukin-17 in conducting destructive arthritis: lessons from animal models," Arthritis Res. Ther., 7:29-37 (2005).
MacCallum et al., "Antibody-antigen Interactions: Contact Analysis and Binding Site Topography," J. Mol. Biol., 1996, 262:732-745.
Mangan et al., "Transforming growth factor-β induces development of the TH17 lineage," Nature, 441:231-234, 2006.
Mannon et al., "Anti-interleukin-12 antibody for active Crohn's disease.," N. Engl. J Med. 351:2069-2079 (2004).
Matusevicius et al., "Interleukin-17 mRNA expression in blood and CSF mononuclear cells is augmented in multiple sclerosis." Mult Seier., 5:101-4 (1999).
McAllister et al., "Role of IL-17A, IL-17F, and the IL-17 receptor in regulating growth-related oncogene-alpha and granulocyte colony-stimulating factor in bronchial epithelium: implications for airway inflammation in cystic fibrosis." J. Immunol., 175: 404-12 (2005).
McInnes et al., "Efficacy and safe of secukinumab, a fully human anti-interleukin-17A monoclonal antibody, in patients with moderate-to-severe psoriatic arthritis: a 24-week, randomised, double-blind, placebo-controlled, phase II proof-of-concept trial," Ann Rheum Dis, 2013, pp. 1-8.
Mease et al., "Managing patients with psoriatric disease: the diagnosis and pharmacologic treatment of psoriatic arthritis in patients with psoriasis," Drugs, 2014, vol. 74, No. 4, p. 423-441.

(56) References Cited

OTHER PUBLICATIONS

Mendez et al., "Functional transplant of megabase human immunoglobulin loci recapitulates human antibody response in mice," Nat Genet, 15:146-156, 1997.
Miller et al., "Targeted vectors for gene therapy," FASEB J., vol. 9:190-199, 1995.
Miossec, "Interleukin-17 in rheumatoid arthritis," Arthritis & Rheum, 48(3):594-601 (2003).
Molet et al., "IL-17 is increased in asthmatic airways and induces human bronchial fibroblasts to produce cytokines." J. Allergy Clin. Immunol., 108:430-8 (2001).
Moseley et al., "Interleukin-17 family and IL-17 receptors," Cytokine & Growth Factor Reviews, 14:155-74 (2003).
Nakae et al., "Suppression of immune induction of collagen-induced arthritis in IL-17-deficient mice," J. Immunol., 171:6173-7 (2003).
Nakae et al., IL-17 production from activated T cells is required for the spontaneous development of destructive arthritis in mice deficient in IL-I receptor antagonist, Proc. Natl. Acad. Sci. USA, 100(10):5986-90 (2003).
Nanevicz et al., "Mechanisms of thrombin receptor agonist specificity," J Biol Chem, 270(37):21619-21625, 1995.
Neve et al., "Expression of an efficient small molecular weight tumour necrosis factor/lymphotoxin antagonist," Cytokine, 8(5):365-370, 1996.
Ngo et al., "Computational Protein Structure Prediction, and the Levinthal Paradox," The Protein Folding Problem and Tertiary Structure Prediction, 1994, pp. 433, 491-495.
Nicholas et al., "Gene Expression in Cells Infected with Gammaherpesvirus Saimiri: Properties of Transcripts from Two Immediate-Early Genes," Virol., 179:189-200, 1990.
Nickoloff, B. and Nestle, F., "Recent insights into the immunopathogenesis of psoriasis provide new therapeutic opportunities," J. Clin. Invest., 113(12):1664-1675, 2004.
Niederau et al., "Inflammatory mediators and acute phase proteins in patients with Crohn's disease and ulcerative colitis," Hepato-Gastroenterol., 44:90-107, 1997.
Numasaki et al., "IL-17 enhances the net angiogenic activity and in vivo growth of human non-small cell lung cancer in SCID mice through promoting CXCR-2-dependent angiogenesis," Journal of Immunology, vol. 175, No. 9, pp. 6177-6189, 2005.
Numasaki et al., "Regulatory roles of IL-17 and IL-17F in G-CSF production by lung microvascular endothelial cells stimulated with IL-1beta and/or TNF-alpha." Immunol. Lett., 95:97-104 (2004).
Oda et al., "Interleukin-17F induces pulmonary neutrophilia and amplifies antigen-induced allergic response." American J. Resp. Grit. Care Med., 171: 12-18 (2005).
Ouyang et al., "The biological functions of T helper 17 cell effector cytokines in inflammation," Immunity, 2008, 28(4):454-67.
Papp et al., "Brodalumab, an Anti-Interleukin-17-Receptor Antibody for Psoriasis," NEJM 2012, 366(13):1181-9.
Park et al., "A distinct lineage of CD4 T cells regulates tissue inflammation by producing interleukin 17," Nat Immunol, 6(11):1133-1141, 2005.
Pelidou et al., "Enhancement of Acute Phase and Inhibition of Chronic Phase of Experimental Autoimmune Neuritis in Lewis Rats by Intranasal Administration of Recombinant Mouse Interleukin 17: Potential Immunoregulatory Role," Exp. Neuro, 163:165-172, 2000.
Petersen, T., "In vivo pharmacological disease models for psoriasis and atopic dermatitis in drug discovery," Basic & Clinical Pharmacology & Toxicology, 99:104-115, 2006.
Pincus, "The American College of Rheumatology (ACR) core data set and derivate "patient only" indices to assess rheumatoid arthritis," Clin. Exp. Rheumatol. 23(5) Suppl. 39:S109-13 (2005).
Pongcharoen et al., "The effect of interleukin-17 on the proliferation and invasion of JEG-3 human choriocarcinoma cells," American Journal of Reproductive Immunology, vol. 55, No. 4, pp. 291-300, 2006.

Ramirez-Carrozzi et al., "IL-17C regulates the innate immune function of epithelial cells in an autocrine manner," Nature Immunology, vol. 12, No. 12, pp. 1159-1166 (2011).
Reiter et al., "Engineering antibody Fv fragments for cancer detection and therapy: Bisulfide-stabilized Fv fragments," Nature Biotech. 14:1239-1245, 1996.
Rich et al., "Nail Psoriasis Severity Index: a useful tool for evaluation of nail psoriasis," J. Am. Acad. Dermatol. 49(2): 206-12, 2003.
Rickel et al., "Identification of functional roles for both IL-17RB and IL-17RA in mediating IL-25-induced activities." J. Immunol., 181: 4299-310 (2008).
Rong et al., "IL-17RD (Sef or IL-17RLM) interacts with IL-17 receptor and mediates IL-17 signaling.," Cell Res., 19:208-15 (2009).
Roque et al., "Antibodies and genetically engineered related molecules: production and purification," Biotechnol. Prog. 20:639-654, 2004.
Rouvier et al., "CLTA-8, Cloned from an Activated T Cell, Bearing AU-Rich Messenger RNA Instability Sequences, and Homologous to a Herpesvirus Saimiri Gene," J. Immunol., 150:5445-5456, 1993.
Rudikoff et al., "Single amino acid substitution altering antigen-binding specificity," Proc Natl Acad Sci USA 1982, vol. 79, p. 1979.
Saenz et al., "Welcome to the neighborhood: epithelial cell-derived cytokines license innate and adaptive immune responses at mucosal sites," Immunol Rev., 2008, 226:172-190.
Sambrook et al., Molecular Cloning: A Laboratory Manual, 3rd ed., Cold Spring Harbor Laboratory Press, Cold Spring Harbor, N.Y.
Schnyder et al., "IL-17 reduces TNF-induced Rantes and VCAM-1 expression," Cytokine, 31(3):191-202 (2005).
Shen et al., "Structure-function relationships in the IL-17 receptor: Implications for signal transduction and therapy," Cytokine, Academic Press Ltd., vol. 41, No. 2, pp. 92-104 (2008).
Simon et al., "Peptoids: a modular approach to drug discovery," Proc. Natl. Acad. Sci. U.S.A. 89:9367, 1992.
Smith-Gill, S. et al., "Contributions of immunoglobulin heavy and light chains to antibody specificity for lysozyme and two haptens," J. Immunol., 139(12):4135-4144, 1987.
Song et al., "IL-17RE is the functional receptor for IL-17C and mediates mucosal immunity to infection with instestinal pathogens," Nature Immunology, vol. 12, No. 12, pp. 1151-1158, (2011).
Song, M. et al., "Light chain of natural antibody plays a dominant role in protein antigen binding," Biochem. Biophys. Res. Comm., 268:390-394, 2000.
Spriggs, "Interleukin-17 and its receptor," J. Clin. Immunol., 17(5):366-9 (1997).
Steiner et al., "Expression and function of pro-inflammatory interleukin IL-17 and IL-17 receptor in normal, benign hyperplastic, and malignant prostate," The Prostate Aug. 1, 2003 LNKD, vol. 56, No. 3, pp. 171-182, 2003.
Stemmer et al., "Single-step assembly of a gene and entire plasmid from large numbers of oligodeoxyribonucleotides," Gene, 164:49-53, 1995.
Sykes et al., "Xenograft Tolerance," Immunological Reviews, vol. 141:245-276, 1994.
Teunissen et al., "Interleukin-17 and interferon-γ synergize in the enhancement of proinflammatory cytokine production by human keratinocytes," J. Invest. Dermatol., 111:645-9 (1998).
Tian et al., "Evi27 encodes a novel membrane protein with homology to the IL17 receptor," Ocogene, 19:2098 (2000).
Tomlinson et al., "Methods for generating multivalent and bispecific antibody fragments. Methods Enzymol," Methods Enzymol. 326:461-479, 2000.
Toy et al., "Cutting edge: interleukin 17 signals through a heteromeric receptor complex." J. Immunol. 177:36-9 (2006).
Trofatter et al., "An Expression-independent Catalog of Genes from Human Chromosome 22," Genome Res. 3(6):214-224 (1995).
Umezawa, "BSD Medical Reports Clinical Study Data: brodalumab in psoriasis," Wireless News, 2014 <http:search.proquest.com/docview/210289466> retrieved from the internet on May 13, 2015.
Vajdos et al., "Comprehensive Functional Maps of the Antigen-binding Site of an Anti-ErbB2 Antibody Obtained with Shotgun Scanning Mutagenesis," J. Mol. Biol. 320, 2002,415-428.

(56) References Cited

OTHER PUBLICATIONS

Van de Kerkhof, PCM, "Consistent control of psoriasis by continuos long-term therapy: the promise of biological treatments," JEADV, 1468-3083:639-650, 2006.
Verhoeyen et al., "Reshaping human antibodies: Grafting an antilysozyme activity," Science 239:1534-1536, 1988.
Verma et al., "Gene Theraphy-promises, problems and prospects," Nature, vol. 389:239-242, 1997.
Viswanathan et al., "Total skin clearance results in improvements in health-related quality of life and reduced symptom severity among patients with moderate to severe psoriasis," J Dermatolog Treat, 2015, 26(3):235-239.
Wang et al., IL-25 augments type 2 immune responses by enhancing the expansion and functions of TSLP-DC-activated Th2 memory cells, J Exp Med., 2007, 204(8):1837-1847.
Ward et al., "Binding activities of a repertoire of single immunoglobulin variable domains secreted from *Escherichia coli*," Nature, 1989, 341:544-546.
Webmd.com definition for DMARDS, pp. 1-3, Jul. 2, 2009.
Wong et al., Elevation of proinflammatory cytokine (IL-18, IL-17, IL-12) and Th2 cytokine (IL-4) concentrations in patiens with systemic lupus erythematosus, Lupu, 9:589-93 (2000).
Wozel, "Psoriasis treatment in difficult locations: scalp, nails, and intertriginous areas," Clin. Derm. 26:448-459, 2008.
Wright et al., "The Human IL-17F/IL-17A Heterodimeric Cytokine Signals through the IL-17RA/IL-17RC Receptor Complex," J Immunol, 2008, 181(4):2799-2805.
Wu et al., "Humanization of a Murine Monoclonal Antibody by Simultaneous Optimization of Framework and CDR Residues," J. Mol. Biol. 294, 1999, 151-162.
Yao et al., "Complete nucleotide sequence of the mouse CTLA8 gene," Gene, 168:223-225, 1996.
Yao et al., "Herpesvirus saimiri encodes a new cytokine, IL-17, which binds to a novel cytokine receptor," Immunity, 3:811-21 (1995).
Yao et al., "Human 1L-17: A novel cytokine derived from T cells," J. Immunol., 155:5483-5486 (1995).
Yao et al., "Molecular characterization of human interleukin (IL)-17 receptor." Cytokine, 9(11):794-800 (1997).
Ye et al., "Requirement of interleukin 17 receptor signaling for lung CXC chemokine and granulocyte colony-stimulating factor expression, neutrophils recruitment, and host defense," J. Exp. Med., 194(4):519-27 (2001).
Yoshimoto et al., "IL-12 up-regulates IL-18 receptor expression on T cells Th1 cells ad B cells: Synergism with IL-18 for IFN-y production," J Immunol, 161:3400-3407, 1998.
You et al., "Differential expression of IL-17RC isoforms in androgen-dependent and adrogen-independent prostate cancers," vol. 9, No. 6, pp. 464-470, (2007).
You et al., Interleukin-17 receptor-like gene is a novel antiapoptotic gene highly expressed in androgen-independent prostate cancer, Cancer Res., 66(1):175-83 (2006).
Zhou et al., "IL-17A versus IL-17F induced intracellular signal transduction pathways and modulation by IL-17RA and IL-17RC RNA interference in AGS gastric adenocarcinoma cells," Cytokine, vol. 38, No. 3, pp. 157-164, 2007.
Ziolkowska et al., "High levels of IL-17 in rheumatoid arthritis patients: IL-15 triggers in vitro IL-17 production via cyclosporine A-sensitive mechanism," J. Immunol., 64:2832-8 (2000).
Zupnick et al., "Mutational analysis of the p53 core domain L1 loop," J Biol Chem, 281(29):20464-20473, 2006.

METHOD OF TREATING DISEASES USING AN IL-17 RECEPTOR ANTIBODY FORMULATION

CROSS-REFERENCE TO RELATED APPLICATIONS

This application is a continuation of copending U.S. application Ser. No. 16/053,564, filed Aug. 2, 2018, which is a continuation of U.S. application Ser. No. 14/499,691, filed Sep. 29, 2014, now U.S. Pat. No. 10,072,085, which is a divisional of U.S. application Ser. No. 13/521,999, filed Jul. 12, 2012, now U.S. Pat. No. 8,883,151, which is a national phase application under 35 U.S.C. § 371 of PCT International Application No. PCT/US2011/020985, filed Jan. 12, 2011, which claims the benefit under 35 U.S.C. 119(e) of U.S. patent application No. 61/295,387, filed Jan. 15, 2010 and U.S. patent application No. 61/422,059, filed Dec. 10, 2010, which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 13,202 Byte ASCII (Text) file named "36253-306-SQL_ST25.TXT," created on Sep. 8, 2020.

BACKGROUND

Interleukin-17 (IL-17A) is an inflammatory cytokine initially identified as a transcript selectively expressed by activated T cells. IL-17A and IL-17F bind and activate IL-17RA. IL-17RA has been shown to be important in regulating immune responses. Activation of the IL-17RA leads to production of cytokines, chemokines, growth factors, and other proteins that contribute to the symptoms and/or pathology of numerous diseases. IL-17A is an inflammatory cytokine that induces the production of cytokines and other mediators leading to diseases and physiological effects such as inflammation, cartilage degradation, and bone resorption. IL-17A may play a role in a number of inflammatory conditions including arthritis (rheumatoid arthritis), psoriasis, inflammatory bowel disease, multiple sclerosis, and asthma. (Li et al., 2004, *Huazhong Univ. Sci. Technolog. Med. Sci.* 24:294-296; Fujino et al., 2003, *Gut.* 52:65-70; Kauffman et al., 2004, *J. Invest. Dermatol.* 123:1037-1044; Mannon et al., 2004, *N. Engl. J Med.* 351:2069-2079; Matusevicius et al., 1999, *Mult Scler* 5, 101-104; Linden et al., *Eur Respir J.* 2000 May; 15(5):973-7; Molet et al., 2001, *J. Allergy Clin. Immunol.* 108:430-438). Recent studies have suggested that IL-17F plays a role in the induction of inflammatory responses (Oda et al., 2006, *American J. Resp. Crit. Care Medicine*, Jan. 15, 2006; Numasaki et al., 2004, *Immunol Lett.* 95:97-104).

IL-17 Receptor A (IL-17RA) has been shown to bind and be activated by IL-17A and IL-17F. Five additional IL-17-like ligands (IL-17B-IL-17F) and four additional IL-17RA-like receptors (IL-17RB-IL-17RE) have been identified (Kolls and Linden, 2004, *Immunity* 21:467-476; Gaffen, 2009, *Nat Rev Immunol* 8:556-568). IL-17 Receptor C (IL-17RC) has been shown to bind and be activated by IL-17A and IL-17F. IL-17RA and IL-17RC form a functional heteromeric receptor complex (Toy et al., 2006, *J. Immunol.* 177:36-39; McAllister et al., 2005, *J. Immunol.* 175:404-412). In addition, IL-17 Receptor B (IL-17RB) has also been shown to require IL-17RA for IL-25 mediated activity (Rickel, et al., 2008, *J. Immunol.* 181:4299-4310), and IL-17RD interacts with IL-17RA to mediate IL-17 signaling (Rong, et al., 2009, *Cell Research* 19:208-215).

DETAILED DESCRIPTION

Figure 1:
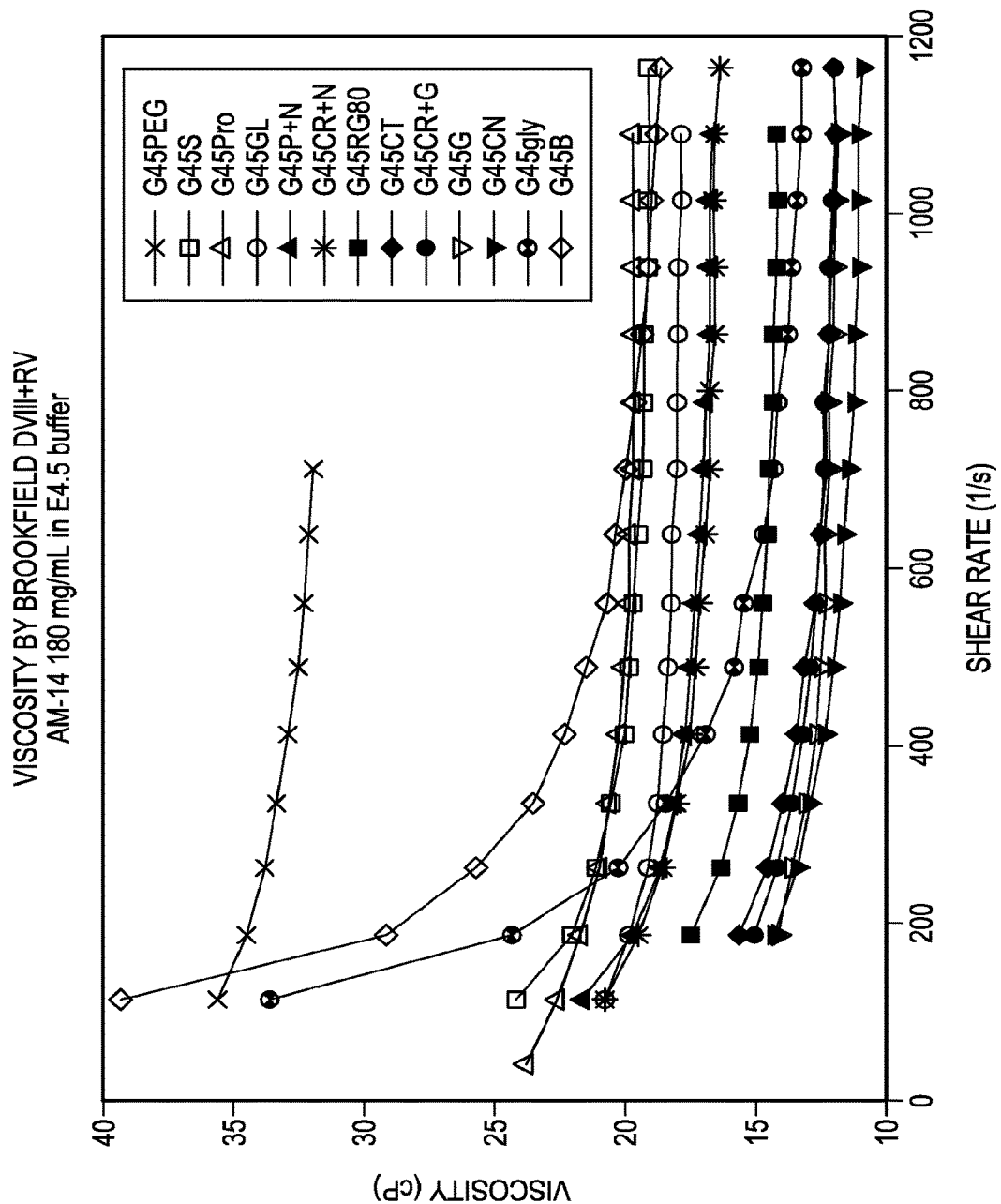
FIG. 1: A graph depicting the relationship between viscosity and shear rate for various AM-14 formulations. Various excipients were evaluated in a 10 mM glutamate, pH 4.5 buffer with AM-14 held constant at approximately 180 mg/ml.

It is understood that any and all of the various attributes of the embodiments provided herein that are described in separate paragraphs and are later combined in a specific embodiment or the selection of a specific embodiment from a list of embodiments does not constitute added or new matter. Applicants affirmatively state that all such combinations are specifically envisioned and are specifically encompassed by this disclosure.

IL-17 Receptor "A"

"IL-17 receptor A" or "IL-17RA" (interchangeably used herein, as well as IL-17 receptor and IL-17R all refer to the same receptor) is the cell surface receptor known in the art (see for example Yao, et al., 1997, *Cytokine* Vol. 9, No. 11:794-800). The cloning, characterization of IL-17RA is described, for example, in U.S. Pat. No. 6,072,033, which is incorporated herein by reference in its entirety. IL-17RA binds, at a minimum, IL-17A and/or IL-17F and is activated by IL-17A and/or IL-17F or other IL-17 ligands, as well as heteromeric forms of one or more IL-17 ligands, such as but not limited to, IL-17A/IL-17F heteromers.

IL-17RA Antibody Biopharmaceutical Formulations

Aspects of the present invention are directed to biopharmaceutical formulations (also referred to herein as simply "formulation") incorporating the AM-14 antibody, as variously defined herein. AM-14 is described in detail in WO 2008/054603, U.S. Ser. No. 11/906,094, U.S. Pat. Nos. 7,786,234, 7,833,527, and 7,767,206 which are herein incorporated by reference in their entirety. AM-14 specifically binds to human IL-17RA and inhibits the biological activity of IL-17A, IL-17F, and IL-17A/IL-17F heterodimers, and/or the activation of IL-17RA as well as a heteromeric complex of IL-17RA and IL-17RC (IL-17 Receptor "C"). AM-14 also has the unique property of inhibiting IL-17RB (IL-17 Receptor "B") activation through its ligand IL-25, while not being bound by this theory, presumably by affecting the heteromeric receptor complex comprising IL-17RA and IL-17RB. The IL-17RA-RB complex and the use of AM-14 in inhibiting the biological activity of IL-25 are described in PCT/US2009/001085 and is herein incorporated by reference in its entirety.

AM-14 comprises a heavy chain sequence comprising SEQ ID NO:1 (or alternatively the heavy chain sequence comprising SEQ ID NO:12 which has the COOH-terminus Lys removed from SEQ ID NO:1) and a light chain sequence comprising SEQ ID NO:2, or a human IL-17RA binding fragment thereof. AM-14 comprises a heavy chain variable region sequence comprising SEQ ID NO:3 and a light chain variable region sequence comprising SEQ ID NO:4, or a human IL-17RA binding fragment thereof, wherein said AM-14 antibody binds human IL-17RA. AM-14 comprises a heavy chain CDR1 comprising SEQ ID NO:5, a heavy chain CDR2 comprising SEQ ID NO:6 (or alternatively the heavy chain CDR2 comprising SEQ ID NO:7), a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, or a human IL-17RA binding fragment thereof, wherein said AM-14 antibody binds human IL-17RA.

As used herein, the term "biopharmaceutical" is intended to mean a macromolecule such as a polypeptide, nucleic acid, carbohydrate or lipid, or building block thereof, that is intended for use as a pharmaceutical, which in this instance is the antibody AM-14. A "biopharmaceutical formulation" refers to a pharmaceutically acceptable medium that is compatible with a biopharmaceutical and is safe and non-toxic when administered to humans.

The term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It is understood that when describing a range of values, the characteristic being described can be an individual value found within the range. For example, "a pH from about pH 4 to about pH 6," can be, but is not limited to, pH 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH.

A formulation comprising a buffering solution and AM-14 is provided. The buffering solution may comprise a glutamic acid or an acetic acid buffer. The buffering solution comprises a glutamic acid buffer. The specification also provides a method of preparing the formulation, methods of treating a condition using the formulated AM-14, and a kit containing components of the formulation.

A highly significant advance has been made in the formulation of AM-14 (i.e., biopharmaceutical formulations of AM-14) in that high concentrations of AM-14 in solution have been achieved. Therefore, embodiments include highly concentrated AM-14 formulations. High concentration AM-14 formulations are desirable in that this allows lower volume administration and/or fewer administrations and consequently less discomfort to the patient.

An additional highly significant advance is that AM-14 formulations have comparatively low viscosity at high protein concentrations. AM-14 formulations having lower viscosity are highly desirable, in that this facilitates manufacturability (such as but not limited to processing, filtering, and filling), the use standard syringe and needle configurations (as appropriate for the route of administration), adaptability to art-known auto-injector and microinfusion devices, ease of administration, and reducing shear forces to AM-14 upon administration. An added benefit of lower viscosity AM-14 formulations is less discomfort to the patient upon administration.

A further highly significant advance over the art is that AM-14 formulations described herein having high concentration of AM-14 (i.e., >100 mg/ml) are surprisingly stable, as described in the stability studies in Example 1.

In addition, it has been surprisingly found that glutamate-based formulations at 10 mM glutamate do not induce unacceptable stinging/pain upon subcutaneous injection, as described in Example 5.

Embodiments of AM-14 formulations include a biopharmaceutical formulation of AM-14 having a concentration range of AM-14 in solution of 60 to 250 mg/ml, 60 to 240 mg/ml, 60 to 230 mg/ml, 60 to 220 mg/ml, 60 to 210 mg/ml, 60 to 200 mg/ml, 60 to 190 mg/ml, 60 to 180 mg/ml, 60 to 170 mg/ml, 60 to 160 mg/ml, 60 to 150 mg/ml, 60 to 140 mg/ml, 60 to 130 mg/ml, 60 to 120 mg/ml, 60 to 110 mg/ml, 60 to 100 mg/ml, 70 to 250 mg/ml, 70 to 240 mg/ml, 70 to 230 mg/ml, 70 to 220 mg/ml, 70 to 210 mg/ml, 70 to 200 mg/ml, 70 to 190 mg/ml, 70 to 180 mg/ml, 70 to 170 mg/ml, 70 to 160 mg/ml, 70 to 150 mg/ml, 70 to 140 mg/ml, 70 to 130 mg/ml, 70 to 120 mg/ml, 70 to 110 mg/ml, 70 to 100 mg/ml, 80 to 250 mg/ml, 80 to 240 mg/ml, 80 to 230 mg/ml, 80 to 220 mg/ml, 80 to 210 mg/ml, 80 to 200 mg/ml, 80 to 190 mg/ml, 80 to 180 mg/ml, 80 to 170 mg/ml, 80 to 160 mg/ml, 80 to 150 mg/ml, 80 to 140 mg/ml, 80 to 130 mg/ml, 80 to 120 mg/ml, 80 to 110 mg/ml, 80 to 100 mg/ml, 90 to 250 mg/ml, 90 to 240 mg/ml, 90 to 230 mg/ml, 90 to 220 mg/ml, 90 to 210 mg/ml, 90 to 200 mg/ml, 90 to 190 mg/ml, 90 to 180 mg/ml, 90 to 170 mg/ml, 90 to 160 mg/ml, 90 to 150 mg/ml, 90 to 140 mg/ml, 90 to 130 mg/ml, 90 to 120 mg/ml, 90 to 110 mg/ml, 90 to 100 mg/ml, 100 to 250 mg/ml, 100 to 240 mg/ml, 100 to 230 mg/ml, 100 to 220 mg/ml, 100 to 210 mg/ml, 100 to 200 mg/ml, 100 to 190 mg/ml, 100 to 180 mg/ml, 100 to 170 mg/ml, 100 to 160 mg/ml, 100 to 150 mg/ml, 100 to 140 mg/ml, 100 to 130 mg/ml, 100 to 120 mg/ml, 100 to 110 mg/ml, 110 to 250 mg/ml, 110 to 240 mg/ml, 110 to 230 mg/ml, 110 to 220 mg/ml, 110 to 210 mg/ml, 110 to 200 mg/ml, 110 to 190 mg/ml, 110 to 180 mg/ml, 110 to 170 mg/ml, 110 to 160 mg/ml, 110 to 150 mg/ml, 110 to 140 mg/ml, 110 to 130 mg/ml, 110 to 120 mg/ml, 120 to 250 mg/ml, 120 to 240 mg/ml, 120 to 230 mg/ml, 120 to 220 mg/ml, 120 to 210 mg/ml, 120 to 200 mg/ml, 120 to 190 mg/ml, 120 to 180 mg/ml, 120 to 170 mg/ml, 120 to 160 mg/ml, 120 to 150 mg/ml, 120 to 140 mg/ml, 120 to 130 mg/ml, 130 to 250 mg/ml, 130 to 240 mg/ml, 130 to 230 mg/ml, 130 to 220 mg/ml, 130 to 210 mg/ml, 130 to 200 mg/ml, 130 to 190 mg/ml, 130 to 180 mg/ml, 130 to 170 mg/ml, 130 to 160 mg/ml, 130 to 150 mg/ml, 130 to 140 mg/ml, 140 to 250 mg/ml, 140 to 240 mg/ml, 140 to 230 mg/ml, 140 to 220 mg/ml, 140 to 210 mg/ml, 140 to 200 mg/ml, 140 to 190 mg/ml, 140 to 180 mg/ml, 140 to 170 mg/ml, 140 to 160 mg/ml, 140 to 150 mg/ml, 150 to 250 mg/ml, 150 to 240 mg/ml, 150 to 230 mg/ml, 150 to 220 mg/ml, 150 to 210 mg/ml, 150 to 200 mg/ml, 150 to 190 mg/ml, 150 to 180 mg/ml, 150 to 170 mg/ml, 150 to 160 mg/ml, 160 to 250 mg/ml, 160 to 240 mg/ml, 160 to 230 mg/ml, 160 to 220 mg/ml, 160 to 210 mg/ml, 160 to 200 mg/ml, 160 to 190 mg/ml, 160 to 180 mg/ml, 160 to 170 mg/ml, 180 to 250 mg/ml, 180 to 240 mg/ml, 180 to 230 mg/ml, 180 to 220 mg/ml, 180 to 210 mg/ml, 180 to 200 mg/ml, 180 to 190 mg/ml, 190 to 250 mg/ml, 190 to 240 mg/ml, 190 to 230 mg/ml, 190 to 220 mg/ml, 190 to 210 mg/ml, 190 to 200 mg/ml, 200 to 250 mg/ml, 200 to 240 mg/ml, 200 to 230 mg/ml, 200 to 220 mg/ml, 200 to 210 mg/ml, 210 to 250 mg/ml, 210 to 240 mg/ml, 210 to 230 mg/ml, 210 to 220 mg/ml, 220 to 250 mg/ml, 220 to 240 mg/ml, 220 to 230 mg/ml, 230 to 250 mg/ml, 230 to 240 mg/ml, or 240 to 250 mg/ml.

Embodiments of AM-14 formulations include a biopharmaceutical formulation of AM-14 having a concentration of at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, or 250 mg/ml. Embodiments of AM-14 formulations include a biopharmaceutical formulation of AM-14 having a concentration of 100-150 mg/ml±0.01-5%. Embodiments of AM-14 formulations include a biopharmaceutical formulation of AM-14 having a concentration of 140 mg/ml±0.01-5%.

Embodiments of AM-14 formulations comprise an acetic acid or glutamic acid buffer wherein the acetic acid or glutamic acid buffer concentration is from about 5 to 30±0.2 mM, including 5±0.2, 6±0.2, 7±0.2, 8±0.2, 9±0.2, 10±0.2, 11±0.2, 12±0.2, 13±0.2, 14±0.2, 15±0.2, 16±0.2, 17±0.2, 18±0.2, 19±0.2, 20±0.2, 21±0.2, 22±0.2, 23±0.2, 24±0.2, 25±0.2, 26±0.2, 27±0.2, 28±0.2, 29±0.2, or 30±0.2 mM. Embodiments of AM-14 formulations comprise a glutamic acid buffer wherein the glutamic acid buffer concentration is 10±0.2 mM.

As used herein, the term "acetic acid buffer" is intended to mean a buffer comprising acetic acid. The buffer can be made from an acetate salt, for example, sodium acetate. Other salts can be used, for example, potassium, ammonium, calcium or magnesium salts of acetate. "Acetic acid buffer" and "acetate buffer" are used interchangeably.

As used herein, the term "glutamic acid buffer" is intended to mean a buffer comprising glutamic acid. The buffer can be made from a glutamate salt, for example, sodium glutamate. Other salts can be used, for example, potassium, ammonium, calcium or magnesium salts of glutamate. "Glutamic acid buffer" and "glutamate buffer" are used interchangeably. In other embodiments, the glutamic acid and/or the acetic acid buffers can be used in combination with proline as an excipient (including L-proline).

Embodiments of AM-14 formulations comprise an acetic acid or glutamic acid buffer having a pH of 4.5 to 5.5±0.2, or a range of 4.8 to 5.2±0.2, including a pH of 4.6±0.2, 4.7±0.2, 4.8±0.2, 4.9±0.2, 5.0±0.2, 5.1±0.2, 5.2±0.2, 5.3±0.2, 5.4±0.2, and 5.5±0.2. Embodiments of AM-14 formulations comprise a glutamic acid buffer having a pH of 4.8±0.2.

As used herein, the term "excipient" is intended to mean a therapeutically inactive substance. Excipients can be included in a biopharmaceutical formulation for a wide variety of purposes including, for example, as a diluent, vehicle, buffer, stabilizer, tonicity agent, bulking agent, surfactant, cryoprotectant, lyoprotectant, anti-oxidant, metal ion source, chelating agent and/or preservative. Optimal excipients also are chosen to enhance or provide stabilization with reference to the mode of administration for an aqueous biopharmaceutical formulation of the invention. For example, parenteral routes of intravenous (IV), subcutaneous (SC) or intramuscular (IM) administration can be more safe and efficacious when all components of the formulation maintain physical and chemical stability during manufacture, storage and administration. The excipients exemplified herein for use in a biopharmaceutical formulation exhibit these and other characteristics. Excipients are well known in the art and can be found described in, for example, Wang W., Int. J. Pharm. 185:129-88 (1999) and Wang W., Int. J. Pharm. 203:1-60 (2000).

Excipients include, for example, polyols such as sorbitol or mannitol; sugars such as sucrose, lactose or dextrose;

polymers such as polyethylene glycol; salts such as NaCl, KCl or calcium phosphate, amino acids such as glycine, methionine or glutamic acid, surfactants, metal ions, buffer salts such as propionate, acetate or succinate, preservatives and polypeptides such as human serum albumin, as well as saline and water. Other excipients useful in either a liquid or lyophilized biopharmaceutical formulation of the invention include, for example, fucose, cellobiose, maltotriose, melibiose, octulose, ribose, xylitol, arginine, histidine, glycine, alanine, methionine, glutamic acid, lysine, imidazole, glycylglycine, mannosylglycerate, Triton X-100, Pluronic F-127, cellulose, cyclodextrin, dextran (10, 40 and/or 70 kD), polydextrose, maltodextrin, ficoll, gelatin, hydroxypropylmeth, sodium phosphate, potassium phosphate, ZnCl2, zinc, zinc oxide, sodium citrate, trisodium citrate, tromethamine, copper, fibronectin, heparin, human serum albumin, protamine, glycerin, glycerol, EDTA, metacresol, benzyl alcohol and phenol. Sugar alcohols, also known as a polyols, polyhydric alcohols, or polyalcohols, are hydrogenated forms of carbohydrate having a carbonyl group reduced to a primary or secondary hydroxyl group. Polyols can be used as stabilizing excipients and/or isotonicity agents in both liquid and lyophilized formulations. Polyols can protect biopharmaceuticals from both physical and chemical degradation pathways. Preferentially excluded co-solvents increase the effective surface tension of solvent at the protein interface whereby the most energetically favorable structural conformations are those with the smallest surface areas. Specific examples of sugar alcohols include sorbitol, glycerol, mannitol, xylitol, maltitol, lactitol, erythritol and threitol. Reducing sugars include, for example, sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars contain an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof.

Embodiments of AM-14 formulations include sucrose, glycine, proline, glycerol, and/or sorbitol as excipients, which can be included at concentration ranges of about 1 to 20% (w/v)±0.2% (w/v), or a range of 5 to 10% (w/v)±0.2% (w/v), or a range of 3 to 9% (w/v)±0.2% (w/v), including a concentration of 1±0.2, 2±0.2, 3±0.2, 4±0.2, 5±0.2, 6±0.2, 7±0.2, 8±0.2, 9±0.2, 10±0.2, 11±0.2, 12±0.2, 13±0.2, 14±0.2, 15±0.2, 16±0.2, 17±0.2, 18±0.2, 19±0.2, or 20%±0.2% (w/v).

As used herein, the term "surfactant" is intended to mean a substance that functions to reduce the surface tension of a liquid in which it is dissolved. Surfactants can be included in a biopharmaceutical formulation for a variety of purposes including, for example, to prevent or control aggregation, particle formation and/or surface adsorption in liquid formulations or to prevent or control these phenomena during the lyophilization and/or reconstitution process in lyophilized formulations. Surfactants include, for example, amphipathic organic compounds that exhibit partial solubility in both organic solvents and aqueous solutions. General characteristics of surfactants include their ability to reduce the surface tension of water, reduce the interfacial tension between oil and water and also form micelles. Surfactants of the invention include non-ionic and ionic surfactants. Surfactants are well known in the art and can be found described in, for example, Randolph T. W. and Jones L. S., Surfactant-protein interactions. Pharm Biotechnol. 13:159-75 (2002). Non-ionic surfactants include, for example, alkyl poly (ethylene oxide), alkyl polyglucosides such as octyl glucoside and decyl maltoside, fatty alcohols such as cetyl alcohol and oleyl alcohol, cocamide MEA, cocamide DEA, and cocamide TEA. Specific examples of non-ionic surfactants include the polysorbates including, for example, polysorbate 20, polysorbate 28, polysorbate 40, polysorbate 60, polysorbate 65, polysorbate 80, polysorbate 81, polysorbate 85 and the like; the poloxamers including, for example, poloxamer 188, also known as poloxalkol or poly(ethylene oxide)-poly(propylene oxide), poloxamer 407 or polyethylene-polypropylene glycol and the like, and polyethylene glycol (PEG). Polysorbate 20 is synonymous with TWEEN 20®, sorbitan monolaurate and polyoxyethylene sorbitan monolaurate. Ionic surfactants include, for example, anionic, cationic and zwitterionic surfactants. Anionic surfactants include, for example, sulfonate-based or carboxylate-based surfactants such as soaps, fatty acid salts, sodium dodecyl sulfate (SDS), ammonium lauryl sulfate and other alkyl sulfate salts. Cationic surfactants include, for example, quaternary ammonium-based surfactants such as cetyl trimethylammonium bromide (CTAB), other alkyltrimethylammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho glycinate.

Embodiments of AM-14 formulations include polysorbate 20 (polyoxyethylene sorbitan monolaurate) as a surfactant, which can be included at concentration ranges of about 0.003 to 1% (w/v), or a range of about 0.008 to 0.02% (w/v) including 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1% (w/v). Embodiments of AM-14 formulations comprise glutamate based buffers comprising polysorbate 20 (polyoxyethylene sorbitan monolaurate) as a surfactant at concentration of about 0.005-0.02% (w/v). Embodiments of AM-14 formulations comprise polysorbate 20 (polyoxyethylene sorbitan monolaurate) as a surfactant at concentration of about 0.01% (w/v).

An AM-14 formulation can be prepared to be isotonic relative to a reference solution or fluid (i.e., blood serum). An isotonic solution has a substantially similar amount of dissolved solute in it compared to the things around it so that it is osmotically stable. Unless expressly compared to a specific solution or fluid, isotonic or isotonicity is exemplary used herein by reference to human blood serum (e.g., 300 mOsmol/kg). Therefore, an isotonic AM-14 formulation will contain a substantially similar concentration of solutes or exhibit substantially similar osmotic pressure as human blood. In general, an isotonic solution contains about the same concentration of solutes as normal saline for humans and many other mammals, which is about 0.9 weight percent (0.009 g/ml) salt in aqueous solution (e.g., 0.009 g/ml NaCl). Embodiments of AM-14 formulations include those that are isotonic or near isotonic and have an osmolarity range of about 250 to 400 osm/L or 275 to 325 osm/L, including an osmolarity of 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 osm/L.

Embodiments of AM-14 formulations include those described herein that have low viscosity despite having a high concentration of antibody in solution. Embodiments of AM-14 formulations, such as those listed in the next paragraph, include AM-14 formulations having a viscosity of between 4 and 10 cP at 25 degrees C. Embodiments of AM-14 formulations, such as those listed in the next paragraph, include AM-14 formulations having a viscosity of between 5 and 7 cP at 25 degrees C. Embodiments of AM-14 formulations, such as those listed in the next paragraph, include AM-14 formulations having a viscosity of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 cP at 25 degrees C. Of course it is understood that these ranges and values are not limited to the enumerated numbers and includes further fractional increments (for example 4.11, 4.12, 4.13, etc.).

Embodiments of AM-14 formulations include, but are not limited to 100-150 mg/mL AM-14, formulated with 5-15 mM glutamic acid, 7-9% (w/v) sucrose, 0.003-0.02% (w/v) polysorbate 20, pH 4.5-5.5±0.2. Embodiments of AM-14 formulations include about 105 mg/mL AM-14, formulated with 10 mM glutamic acid, 8% (w/v) sucrose, 0.01% (w/v) polysorbate 20, pH 4.8±0.2. Embodiments of AM-14 formulations include about 110 mg/mL AM-14, formulated with 10 mM glutamic acid, 8% (w/v) sucrose, 0.01% (w/v) polysorbate 20, pH 4.8±0.2. Embodiments of AM-14 formulations include about 120 mg/mL AM-14, formulated with 10 mM glutamic acid, 8% (w/v) sucrose, 0.01% (w/v) polysorbate 20, pH 4.8±0.2. Embodiments of AM-14 formulations include about 130 mg/mL AM-14, formulated with 10 mM glutamic acid, 8% (w/v) sucrose, 0.01% (w/v) polysorbate 20, pH 4.8±0.2. Embodiments of AM-14 formulations include about 140 mg/mL AM-14, formulated with 10 mM glutamic acid, 8% (w/v) sucrose, 0.01% (w/v) polysorbate 20, pH 4.8±0.2. Embodiments of AM-14 formulations include about 150 mg/mL AM-14, formulated with 10 mM glutamic acid, 8% (w/v) sucrose, 0.01% (w/v) polysorbate 20, pH 4.8±0.2.

Embodiments of AM-14 formulations include, but are not limited to 100-150 mg/mL AM-14, formulated with 5-15 mM glutamic acid, 1-3% (w/v) glycine, 0.003-0.02% (w/v) polysorbate 20, pH 4.5-5.5±0.2. Embodiments of AM-14 formulations include about 105 mg/mL AM-14, formulated with 10 mM glutamic acid, 2% (w/v) glycine, 0.01% (w/v) polysorbate 20, pH 4.8±0.2. Embodiments of AM-14 formulations include about 110 mg/mL AM-14, formulated with 10 mM glutamic acid, 2% (w/v) glycine, 0.01% (w/v) polysorbate 20, pH 4.8±0.2. Embodiments of AM-14 formulations include about 120 mg/mL AM-14, formulated with 10 mM glutamic acid, 2% (w/v) glycine, 0.01% (w/v) polysorbate 20, pH 4.8±0.2. Embodiments of AM-14 formulations include about 130 mg/mL AM-14, formulated with 10 mM glutamic acid, 2% (w/v) glycine, 0.01% (w/v) polysorbate 20, pH 4.8±0.2. Embodiments of AM-14 formulations include about 140 mg/mL AM-14, formulated with 10 mM glutamic acid, 2% (w/v) glycine, 0.01% (w/v) polysorbate 20, pH 4.8±0.2. Embodiments of AM-14 formulations include about 150 mg/mL AM-14, formulated with 10 mM glutamic acid, 2% (w/v) glycine, 0.01% (w/v) polysorbate 20, pH 4.8±0.2.

Embodiments of AM-14 formulations include, but are not limited to 100-150 mg/mL AM-14, formulated with 5-15 mM glutamic acid, 2-4% (w/v) proline, 0.003-0.02% (w/v) polysorbate 20, pH 4.5-5.5±0.2. Embodiments of AM-14 formulations include about 105 mg/mL AM-14, formulated with 10 mM glutamic acid, 3% (w/v) L-proline, 0.01% (w/v) polysorbate 20, pH 4.8±0.2. Embodiments of AM-14 formulations include about 110 mg/mL AM-14, formulated with 10 mM glutamic acid, 3% (w/v) L-proline, 0.01% (w/v) polysorbate 20, pH 4.8±0.2. Embodiments of AM-14 formulations include about 120 mg/mL AM-14, formulated with 10 mM glutamic acid, 3% (w/v) L-proline, 0.01% (w/v) polysorbate 20, pH 4.8±0.2. Embodiments of AM-14 formulations include about 130 mg/mL AM-14, formulated with 10 mM glutamic acid, 3% (w/v) L-proline, 0.01% (w/v) polysorbate 20, pH 4.8±0.2. Embodiments of AM-14 formulations include about 140 mg/mL AM-14, formulated with 10 mM glutamic acid, 3% (w/v) L-proline, 0.01% (w/v) polysorbate 20, pH 4.8±0.2. Embodiments of AM-14 formulations include 140 mg/mL AM-14, formulated with 10 mM glutamic acid, 3% (w/v) L-proline, 0.01% (w/v) polysorbate 20, pH 4.8. Embodiments of AM-14 formulations include about 150 mg/mL AM-14, formulated with 10 mM glutamic acid, 3% (w/v) L-proline, 0.01% (w/v) polysorbate 20, pH 4.8±0.2.

Embodiments of AM-14 formulations include, but are not limited to 100-150 mg/mL AM-14, formulated with 5-15 mM acetic acid, 1-3% (w/v) glycine, 0.003-0.02% (w/v) polysorbate 20, pH 4.5-5.5±0.2. Embodiments of AM-14 formulations include about 105 mg/mL AM-14, formulated with 10 mM acetic acid, 2% (w/v) glycine, 0.01% (w/v) polysorbate 20, pH 4.8±0.2. Embodiments of AM-14 formulations include about 110 mg/mL AM-14, formulated with 10 mM acetic acid, 2% (w/v) glycine, 0.01% (w/v) polysorbate 20, pH 4.8±0.2. Embodiments of AM-14 formulations include about 120 mg/mL AM-14, formulated with 10 mM acetic acid, 2% (w/v) glycine, 0.01% (w/v) polysorbate 20, pH 4.8±0.2. Embodiments of AM-14 formulations include about 130 mg/mL AM-14, formulated with 10 mM acetic acid, 2% (w/v) glycine, 0.01% (w/v) polysorbate 20, pH 4.8±0.2. Embodiments of AM-14 formulations include about 140 mg/mL AM-14, formulated with 10 mM acetic acid, 2% (w/v) glycine, 0.01% (w/v) polysorbate 20, pH 4.8±0.2. Embodiments of AM-14 formulations include about 150 mg/mL AM-14, formulated with 10 mM acetic acid, 2% (w/v) glycine, 0.01% (w/v) polysorbate 20, pH 4.8±0.2.

Embodiments of AM-14 formulations include, but are not limited to 100-150 mg/mL AM-14, formulated with 5-15 mM acetic acid, 2-4% (w/v) proline, 0.003-0.02% (w/v) polysorbate 20, pH 4.5-5.5±0.2. Embodiments of AM-14 formulations include about 105 mg/mL AM-14, formulated with 10 mM acetic acid, 3% (w/v) L-proline, 0.01% (w/v) polysorbate 20, pH 4.8±0.2. Embodiments of AM-14 formulations include about 110 mg/mL AM-14, formulated with 10 mM acetic acid, 3% (w/v) L-proline, 0.01% (w/v) polysorbate 20, pH 4.8±0.2. Embodiments of AM-14 formulations include about 120 mg/mL AM-14, formulated with 10 mM acetic acid, 3% (w/v) L-proline, 0.01% (w/v) polysorbate 20, pH 4.8±0.2. Embodiments of AM-14 formulations include about 130 mg/mL AM-14, formulated with 10 mM acetic acid, 3% (w/v) L-proline, 0.01% (w/v) polysorbate 20, pH 4.8±0.2. Embodiments of AM-14 formulations include about 140 mg/mL AM-14, formulated with 10 mM acetic acid, 3% (w/v) L-proline, 0.01% (w/v) polysorbate 20, pH 4.8±0.2. Embodiments of AM-14 formulations include about 150 mg/mL AM-14, formulated with 10 mM acetic acid, 3% (w/v) L-proline, 0.01% (w/v) polysorbate 20, pH 4.8±0.2.

Embodiments of AM-14 formulations include, but are not limited to 100-150 mg/mL AM-14, formulated with 5-15 mM acetic acid, 7-9% (w/v) sucrose, 0.003-0.02% (w/v) polysorbate 20, pH 4.5-5.5±0.2. Embodiments of AM-14 formulations include about 105 mg/mL AM-14, formulated with 10 mM acetic acid, 8% (w/v) sucrose, 0.01% (w/v) polysorbate 20, pH 4.8±0.2. Embodiments of AM-14 formulations include about 110 mg/mL AM-14, formulated with 10 mM acetic acid, 8% (w/v) sucrose, 0.01% (w/v) polysorbate 20, pH 4.8±0.2. Embodiments of AM-14 formulations include about 120 mg/mL AM-14, formulated with 10 mM acetic acid, 8% (w/v) sucrose, 0.01% (w/v) polysorbate 20, pH 4.8±0.2. Embodiments of AM-14 formulations include about 130 mg/mL AM-14, formulated with 10 mM acetic acid, 8% (w/v) sucrose, 0.01% (w/v) polysorbate 20, pH 4.8±0.2. Embodiments of AM-14 formulations include about 140 mg/mL AM-14, formulated with 10 mM acetic acid, 8% (w/v) sucrose, 0.01% (w/v) polysorbate 20, pH 4.8±0.2. Embodiments of AM-14 formulations include about 150 mg/mL AM-14, formulated with 10 mM acetic acid, 8% (w/v) sucrose, 0.01% (w/v) polysorbate 20, pH 4.8±0.2.

Embodiments of AM-14 formulations include, but are not limited to 100-150 mg/mL AM-14, formulated with 5-15 mM acetic acid, 2-4% (w/v) glycerol, 0.003-0.02% (w/v) polysorbate 20, pH 4.5-5.5±0.2. Embodiments of AM-14 formulations include about 105 mg/mL AM-14, formulated with 10 mM acetic acid, 3% (w/v) glycerol, 0.01% (w/v) polysorbate 20, pH 4.8±0.2. Embodiments of AM-14 formulations include about 110 mg/mL AM-14, formulated with 10 mM acetic acid, 3% (w/v) glycerol, 0.01% (w/v) polysorbate 20, pH 4.8±0.2. Embodiments of AM-14 formulations include about 120 mg/mL AM-14, formulated with 10 mM acetic acid, 3% (w/v) glycerol, 0.01% (w/v) polysorbate 20, pH 4.8±0.2. Embodiments of AM-14 formulations include about 130 mg/mL AM-14, formulated with 10 mM acetic acid, 3% (w/v) glycerol, 0.01% (w/v) polysorbate 20, pH 4.8±0.2. Embodiments of AM-14 formulations include about 140 mg/mL AM-14, formulated with 10 mM acetic acid, 3% (w/v) glycerol, 0.01% (w/v) polysorbate 20, pH 4.8±0.2. Embodiments of AM-14 formulations include about 150 mg/mL AM-14, formulated with 10 mM acetic acid, 3% (w/v) glycerol, 0.01% (w/v) polysorbate 20, pH 4.8±0.2.

Embodiments of AM-14 formulations include, but are not limited to 100-150 mg/mL AM-14, formulated with 5-15 mM acetic acid, 3.5-5.5% (w/v) sorbitol, 0.003-0.02% (w/v) polysorbate 20, pH 4.5-5.5±0.2. Embodiments of AM-14 formulations include about 105 mg/mL AM-14, formulated with 10 mM acetic acid, 4.5% (w/v) sorbitol, 0.01% (w/v) polysorbate 20, pH 4.8±0.2. Embodiments of AM-14 formulations include about 110 mg/mL AM-14, formulated with 10 mM acetic acid, 4.5% (w/v) sorbitol, 0.01% (w/v) polysorbate 20, pH 4.8±0.2. Embodiments of AM-14 formulations include about 120 mg/mL AM-14, formulated with 10 mM acetic acid, 4.5% (w/v) sorbitol, 0.01% (w/v) polysorbate 20, pH 4.8±0.2. Embodiments of AM-14 formulations include about 130 mg/mL AM-14, formulated with 10 mM acetic acid, 4.5% (w/v) sorbitol, 0.01% (w/v) polysorbate 20, pH 4.8±0.2. Embodiments of AM-14 formulations include about 140 mg/mL AM-14, formulated with 10 mM acetic acid, 4.5% (w/v) sorbitol, 0.01% (w/v) polysorbate 20, pH 4.8±0.2. Embodiments of AM-14 formulations include about 150 mg/mL AM-14, formulated with 10 mM acetic acid, 4.5% (w/v) sorbitol, 0.01% (w/v) polysorbate 20, pH 4.8±0.2.

Embodiments of AM-14 formulations include, but are not limited to 100-150 mg/mL AM-14, formulated with 5-15 mM glutamic acid, 7-9% (w/v) sucrose, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM glutamic acid, 8% (w/v) sucrose, 0.01% (w/v) polysorbate 20, pH 4.8±0.2, 5-7 cP at 25 degrees C. Embodiments of AM-14 formulations include about 110 mg/mL AM-14, formulated with 10 mM glutamic acid, 8% (w/v) sucrose, 0.01% (w/v) polysorbate 20, pH 4.8±0.2, 5-7 cP at 25 degrees C. Embodiments of AM-14 formulations include about 120 mg/mL AM-14, formulated with 10 mM glutamic acid, 8% (w/v) sucrose, 0.01% (w/v) polysorbate 20, pH 4.8±0.2, 5-7 cP at 25 degrees C. Embodiments of AM-14 formulations include about 130 mg/mL AM-14, formulated with 10 mM glutamic acid, 8% (w/v) sucrose, 0.01% (w/v) polysorbate 20, pH 4.8±0.2, 5-7 cP at 25 degrees C. Embodiments of AM-14 formulations include about 140 mg/mL AM-14, formulated with 10 mM glutamic acid, 8% (w/v) sucrose, 0.01% (w/v) polysorbate 20, pH 4.8±0.2, 5-7 cP at 25 degrees C. Embodiments of AM-14 formulations include about 150 mg/mL AM-14, formulated with 10 mM glutamic acid, 8% (w/v) sucrose, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM glutamic acid, 1-3% (w/v) glycine, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM glutamic acid, 2% (w/v) glycine, 0.01% (w/v) polysorbate 20, pH 4.8±0.2, 5-7 cP at 25 degrees C. Embodiments of AM-14 formulations include about 110 mg/mL AM-14, formulated with 10 mM glutamic acid, 2% (w/v) glycine, 0.01% (w/v) polysorbate 20, pH 4.8±0.2, 5-7 cP at 25 degrees C. Embodiments of AM-14 formulations include about 120 mg/mL AM-14, formulated with 10 mM glutamic acid, 2% (w/v) glycine, 0.01% (w/v) polysorbate 20, pH 4.8±0.2, 5-7 cP at 25 degrees C. Embodiments of AM-14 formulations include about 130 mg/mL AM-14, formulated with 10 mM glutamic acid, 2% (w/v) glycine, 0.01% (w/v) polysorbate 20, pH 4.8±0.2, 5-7 cP at 25 degrees C. Embodiments of AM-14 formulations include about 140 mg/mL AM-14, formulated with 10 mM glutamic acid, 2% (w/v) glycine, 0.01% (w/v) polysorbate 20, pH 4.8±0.2, 5-7 cP at 25 degrees C. Embodiments of AM-14 formulations include about 150 mg/mL AM-14, formulated with 10 mM glutamic acid, 2% (w/v) glycine, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM glutamic acid, 2-4% (w/v) proline, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM glutamic acid, 3% (w/v) L-proline, 0.01% (w/v) polysorbate 20, pH 4.8±0.2, 5-7 cP at 25 degrees C. Embodiments of AM-14 formulations include about 110 mg/mL AM-14, formulated with 10 mM glutamic acid, 3% (w/v) L-proline, 0.01% (w/v) polysorbate 20, pH 4.8±0.2, 5-7 cP at 25 degrees C. Embodiments of AM-14 formulations include about 120 mg/mL AM-14, formulated with 10 mM glutamic acid, 3% (w/v)

L-proline, 0.01% (w/v) polysorbate 20, pH 4.8±0.2, 5-7 cP at 25 degrees C. Embodiments of AM-14 formulations include about 130 mg/mL AM-14, formulated with 10 mM glutamic acid, 3% (w/v) L-proline, 0.01% (w/v) polysorbate 20, pH 4.8±0.2, 5-7 cP at 25 degrees C. Embodiments of AM-14 formulations include about 140 mg/mL AM-14, formulated with 10 mM glutamic acid, 3% (w/v) L-proline, 0.01% (w/v) polysorbate 20, pH 4.8±0.2, 5-7 cP at 25 degrees C. Embodiments of AM-14 formulations include about 150 mg/mL AM-14, formulated with 10 mM glutamic acid, 3% (w/v) L-proline, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM acetic acid, 1-3% (w/v) glycine, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM acetic acid, 2% (w/v) glycine, 0.01% (w/v) polysorbate 20, pH 4.8±0.2, 5-7 cP at 25 degrees C. Embodiments of AM-14 formulations include about 110 mg/mL AM-14, formulated with 10 mM acetic acid, 2% (w/v) glycine, 0.01% (w/v) polysorbate 20, pH 4.8±0.2, 5-7 cP at 25 degrees C. Embodiments of AM-14 formulations include about 120 mg/mL AM-14, formulated with 10 mM acetic acid, 2% (w/v) glycine, 0.01% (w/v) polysorbate 20, pH 4.8±0.2, 5-7 cP at 25 degrees C. Embodiments of AM-14 formulations include about 130 mg/mL AM-14, formulated with 10 mM acetic acid, 2% (w/v) glycine, 0.01% (w/v) polysorbate 20, pH 4.8±0.2, 5-7 cP at 25 degrees C. Embodiments of AM-14 formulations include about 140 mg/mL AM-14, formulated with 10 mM acetic acid, 2% (w/v) glycine, 0.01% (w/v) polysorbate 20, pH 4.8±0.2, 5-7 cP at 25 degrees C. Embodiments of AM-14 formulations include about 150 mg/mL AM-14, formulated with 10 mM acetic acid, 2% (w/v) glycine, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM acetic acid, 2-4% (w/v) proline, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM acetic acid, 3% (w/v) L-proline, 0.01% (w/v) polysorbate 20, pH 4.8±0.2, 5-7 cP at 25 degrees C. Embodiments of AM-14 formulations include about 110 mg/mL AM-14, formulated with 10 mM acetic acid, 3% (w/v) L-proline, 0.01% (w/v) polysorbate 20, pH 4.8±0.2, 5-7 cP at 25 degrees C. Embodiments of AM-14 formulations include about 120 mg/mL AM-14, formulated with 10 mM acetic acid, 3% (w/v) L-proline, 0.01% (w/v) polysorbate 20, pH 4.8±0.2, 5-7 cP at 25 degrees C. Embodiments of AM-14 formulations include about 130 mg/mL AM-14, formulated with 10 mM acetic acid, 3% (w/v) L-proline, 0.01% (w/v) polysorbate 20, pH 4.8±0.2, 5-7 cP at 25 degrees C. Embodiments of AM-14 formulations include about 140 mg/mL AM-14, formulated with 10 mM acetic acid, 3% (w/v) L-proline, 0.01% (w/v) polysorbate 20, pH 4.8±0.2, 5-7 cP at 25 degrees C. Embodiments of AM-14 formulations include about 150 mg/mL AM-14, formulated with 10 mM acetic acid, 3% (w/v) L-proline, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM acetic acid, 7-9% (w/v) sucrose, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM acetic acid, 8% (w/v) sucrose, 0.01% (w/v) polysorbate 20, pH 4.8±0.2, 5-7 cP at 25 degrees C. Embodiments of AM-14 formulations include about 110 mg/mL AM-14, formulated with 10 mM acetic acid, 8% (w/v) sucrose, 0.01% (w/v) polysorbate 20, pH 4.8±0.2, 5-7 cP at 25 degrees C. Embodiments of AM-14 formulations include about 120 mg/mL AM-14, formulated with 10 mM acetic acid, 8% (w/v) sucrose, 0.01% (w/v) polysorbate 20, pH 4.8±0.2, 5-7 cP at 25 degrees C. Embodiments of AM-14 formulations include about 130 mg/mL AM-14, formulated with 10 mM acetic acid, 8% (w/v) sucrose, 0.01% (w/v) polysorbate 20, pH 4.8±0.2, 5-7 cP at 25 degrees C. Embodiments of AM-14 formulations include about 140 mg/mL AM-14, formulated with 10 mM acetic acid, 8% (w/v) sucrose, 0.01% (w/v) polysorbate 20, pH 4.8±0.2, 5-7 cP at 25 degrees C. Embodiments of AM-14 formulations include about 150 mg/mL AM-14, formulated with 10 mM acetic acid, 8% (w/v) sucrose, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM acetic acid, 2-4% (w/v) glycerol, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM acetic acid, 3% (w/v) glycerol, 0.01% (w/v) polysorbate 20, pH 4.8±0.2, 5-7 cP at 25 degrees C. Embodiments of AM-14 formulations include about 110 mg/mL AM-14, formulated with 10 mM acetic acid, 3% (w/v) glycerol, 0.01% (w/v) polysorbate 20, pH 4.8±0.2, 5-7 cP at 25 degrees C. Embodiments of AM-14 formulations include about 120 mg/mL AM-14, formulated with 10 mM acetic acid, 3% (w/v) glycerol, 0.01% (w/v) polysorbate 20, pH 4.8±0.2, 5-7 cP at 25 degrees C. Embodiments of AM-14 formulations include about 130 mg/mL AM-14, formulated with 10 mM acetic acid, 3% (w/v) glycerol, 0.01% (w/v) polysorbate 20, pH 4.8±0.2, 5-7 cP at 25 degrees C. Embodiments of AM-14 formulations include about 140 mg/mL AM-14, formulated with 10 mM acetic acid, 3% (w/v) glycerol, 0.01% (w/v) polysorbate 20, pH 4.8±0.2, 5-7 cP at 25 degrees C. Embodiments of AM-14 formulations include about 150 mg/mL AM-14, formulated with 10 mM acetic acid, 3% (w/v) glycerol, 0.01% (w/v) polysorbate 20, pH 4.8±0.2, 5-7 cP at 25 degrees C.

Embodiments of AM-14 formulations include, but are not limited to 100-150 mg/mL AM-14, formulated with 5-15 mM acetic acid, 3.5-5.5% (w/v) sorbitol, 0.003-0.02% (w/v) polysorbate 20, pH 4.5-5.5±0.2, 4-10 cP at 25 degrees C. Embodiments of AM-14 formulations include about 105 mg/mL AM-14, formulated with 10 mM acetic acid, 4.5% (w/v) sorbitol, 0.01% (w/v) polysorbate 20, pH 4.8±0.2, 5-7 cP at 25 degrees C. Embodiments of AM-14 formulations include about 110 mg/mL AM-14, formulated with 10 mM acetic acid, 4.5% (w/v) sorbitol, 0.01% (w/v) polysorbate 20, pH 4.8±0.2, 5-7 cP at 25 degrees C. Embodiments of AM-14 formulations include about 120 mg/mL AM-14, formulated with 10 mM acetic acid, 4.5% (w/v) sorbitol, 0.01% (w/v) polysorbate 20, pH 4.8±0.2, 5-7 cP at 25 degrees C. Embodiments of AM-14 formulations include about 130 mg/mL AM-14, formulated with 10 mM acetic acid, 4.5% (w/v) sorbitol, 0.01% (w/v) polysorbate 20, pH 4.8±0.2, 5-7 cP at 25 degrees C. Embodiments of AM-14 formulations include about 140 mg/mL AM-14, formulated with 10 mM acetic acid, 4.5% (w/v) sorbitol, 0.01% (w/v) polysorbate 20, pH 4.8±0.2, 5-7 cP at 25 degrees C. Embodiments of AM-14 formulations include about 150 mg/mL AM-14, formulated with 10 mM acetic acid, 4.5% (w/v) sorbitol, 0.01% (w/v) polysorbate 20, pH 4.8±0.2, 5-7 cP at 25 degrees C. The term "about" means±0.01 to 5.0%.

Stability of an AM-14 biopharmaceutical formulation of the invention refers to the retention of structure and/or function of a biopharmaceutical within a formulation. A biopharmaceutical in a formulation of the invention will exhibit attributes such as resistance to change or deterioration that affect stability or function and therefore maintain consistent functional characteristics over time. Accordingly, AM-14 formulations will exhibit, for example, reliability and safety with respect to activity per volume or activity units.

In one embodiment, the stability of an AM-14 biopharmaceutical within a formulation of the invention includes, for example, the retention of physical and/or chemical stability. Biopharmaceutical stability of AM-14 can be assessed by, for example, determining whether the AM-14 has been subjected to physical and/or chemical degradation, including chemical modification of its structure. Stability may be measured by any means known in the art, such as measuring protein aggregates and/or protein break-down products by photometric and/or chromatographic methods. Retention in stability of a AM-14 in a formulation includes, for example, retention of physical and/or chemical stability between about 80-100%, including retention of stability at least about 99%, 98%, 97%, 96%, 95%, 94%, 93%, 92%, 91%, 90%, 89%, 88%, 87%, 86%, 85%, 84%, 83%, 82%, 81% or 80% compared to the stability of AM-14 at an initial time point. Example 1 describes such stability studies and exemplary means for measuring physical and/or chemical stability.

Embodiments include AM-14 formulations such as: 100-150 mg/mL AM-14, formulated with 5-15 mM glutamic acid, 7-9% (w/v) sucrose, 0.003-0.02% (w/v) polysorbate 20, pH 4.5-5.5±0.2; such as 140 mg/mL AM-14, formulated with 10 mM glutamic acid, 8% (w/v) sucrose, 0.01% (w/v) polysorbate 20, pH 4.8±0.2; 100-150 mg/mL AM-14, formulated with 5-15 mM glutamic acid, 1-3% (w/v) glycine, 0.003-0.02% (w/v) polysorbate 20, pH 4.5-5.5±0.2, such as 140 mg/mL AM-14, formulated with 10 mM glutamic acid, 2% (w/v) glycine, 0.01% (w/v) polysorbate 20, pH 4.8±0.2; 100-1500 mg/mL AM-14, formulated with 5-15 mM glutamic acid, 2-4% (w/v) proline, 0.003-0.02% (w/v) polysorbate 20, pH 4.5-5.5±0.2, such as about 140 mg/mL AM-14, formulated with 10 mM glutamic acid, 3% (w/v) L-proline, 0.01% (w/v) polysorbate 20, pH 4.8±0.2, and 140 mg/mL AM-14, formulated with 10 mM glutamic acid, 3% (w/v) L-proline, 0.01% (w/v) polysorbate 20, pH 4.8±0.2; 100-150 mg/mL AM-14, formulated with 5-15 mM acetic acid, 1-3% (w/v) glycine, 0.003-0.02% (w/v) polysorbate 20, pH 4.5-5.5±0.2, such as 140 mg/mL AM-14, formulated with 10 mM acetic acid, 2% (w/v) glycine, 0.01% (w/v) polysorbate 20, pH 4.8±0.2; 100-150 mg/mL AM-14, formulated with 5-15 mM acetic acid, 2-4% (w/v) proline, 0.003-0.02% (w/v) polysorbate 20, pH 4.5-5.5±0.2, such as 140 mg/mL AM-14, formulated with 10 mM acetic acid, 3% (w/v) L-proline, 0.01% (w/v) polysorbate 20, pH 4.8±0.2; 100-150 mg/mL AM-14, formulated with 5-15 mM acetic acid, 7-9% (w/v) sucrose, 0.003-0.02% (w/v) polysorbate 20, pH 4.5-5.5±0.2, such as 140 mg/mL AM-14, formulated with 10 mM acetic acid, 8% (w/v) polysorbate 20, pH 4.8±0.2; 100-150 mg/mL AM-14, formulated with 5-15 mM acetic acid, 2-4% (w/v) glycerol, 0.003-0.02% (w/v) polysorbate 20, pH 4.5-5.5±0.2, such as 140 mg/mL AM-14, formulated with 10 mM acetic acid, 3% (w/v) glycerol, 0.01% (w/v) polysorbate 20, pH 4.8±0.2; 100-150 mg/mL AM-14, formulated with 5-15 mM acetic acid, 3.5-5.5% (w/v) sorbitol, 0.003-0.02% (w/v) polysorbate 20, pH 4.5-5.5±0.2, such as 140 mg/mL AM-14, formulated with 10 mM acetic acid, 4.5% (w/v) sorbitol, 0.01% (w/v) polysorbate 20, pH 4.8±0.2; 100-150 mg/mL AM-14, formulated with 5-15 mM glutamic acid, 7-9% (w/v) sucrose, 0.003-0.02% (w/v) polysorbate 20, pH 4.5-5.5±0.2, 4-10 cP at 25 degrees C., such as 140 mg/mL AM-14, formulated with 10 mM glutamic acid, 8% (w/v) sucrose, 0.01% (w/v) polysorbate 20, pH 4.8±0.2, 5-7 cP at 25 degrees C.; 100-150 mg/mL AM-14, formulated with 5-15 mM glutamic acid, 1-3% (w/v) glycine, 0.003-0.02% (w/v) polysorbate 20, pH 4.5-5.5±0.2, 4-10 cP at 25 degrees C., such as 140 mg/mL AM-14, formulated with 10 mM glutamic acid, 2% (w/v) glycine, 0.01% (w/v) polysorbate 20, pH 4.8±0.2, 5-7 cP at 25 degrees C.; 100-150 mg/mL AM-14, formulated with 5-15 mM glutamic acid, 2-4% (w/v) proline, 0.003-0.02% (w/v) polysorbate 20, pH 4.5-5.5±0.2, 4-10 cP at 25 degrees C., such as 140 mg/mL AM-14, formulated with 10 mM glutamic acid, 3% (w/v) L-proline, 0.01% (w/v) polysorbate 20, pH 4.8±0.2, 5-7 cP at 25 degrees C.; 100-150 mg/mL AM-14, formulated with 5-15 mM acetic acid, 1-3% (w/v) glycine, 0.003-0.02% (w/v) polysorbate 20, pH 4.5-5.5±0.2, 4-10 cP at 25 degrees C., such as 140 mg/mL AM-14, formulated with 10 mM acetic acid, 2% (w/v) glycine, 0.01% (w/v) polysorbate 20, pH 4.8±0.2, 5-7 cP at 25 degrees C.; 100-150 mg/mL AM-14, formulated with 5-15 mM acetic acid, 2-4% (w/v) proline, 0.003-0.02% (w/v) polysorbate 20, pH 4.5-5.5±0.2, 4-10 cP at 25 degrees C., such as 140 mg/mL AM-14, formulated with 10 mM acetic acid, 3% (w/v) L-proline, 0.01% (w/v) polysorbate 20, pH 4.8±0.2, 5-7 cP at 25 degrees C.; 100-150 mg/mL AM-14, formulated with 5-15 mM acetic acid, 7-9% (w/v) sucrose, 0.003-0.02% (w/v) polysorbate 20, pH 4.5-5.5±0.2, 4-10 cP at 25 degrees C., such as 140 mg/mL AM-14, formulated with 10 mM acetic acid, 8% (w/v) sucrose, 0.01% (w/v) polysorbate 20, pH 4.8±0.2, 5-7 cP at 25 degrees C.; 100-150 mg/mL AM-14, formulated with 5-15 mM acetic acid, 2-4% (w/v) glycerol, 0.003-0.02% (w/v) polysorbate 20, pH 4.5-5.5±0.2, 4-10 cP at 25 degrees C., such as 140 mg/mL AM-14, formulated with 10 mM acetic acid, 3% (w/v) glycerol, 0.01% (w/v) polysorbate 20, pH 4.8±0.2, 5-7 cP at 25 degrees C.; 100-150 mg/mL AM-14, formulated with 5-15 mM acetic acid, 3.5-5.5% (w/v) sorbitol, 0.003-0.02% (w/v) polysorbate 20, pH 4.5-5.5±0.2, 4-10 cP at 25 degrees C., such as 140 mg/mL AM-14, formulated with 10 mM acetic acid, 4.5% (w/v) sorbitol, 0.01% (w/v) polysorbate 20, pH 4.8±0.2, 5-7 cP at 25 degrees C. having retention of physical and/or chemical stability between about 80-100%, including retention of stability at least about 99%, 98%, 97%, 96%, 95%, 94%, 93%, 92%, 91%, 90%, 89%, 88%, 87%, 86%, 85%, 84%, 83%, 82%, 81% or 80% compared to the stability of AM-14 at an initial time point.

A biopharmaceutical formulation of the invention will, in general, be prepared according to pharmaceutical standards and using pharmaceutical grade reagents. Similarly, a biopharmaceutical formulation of the invention will, in general, be prepared using sterile reagents in a sterile manufacturing environment or sterilized following preparation. Sterile injectable solutions can be prepared using well known procedures in the art including, for example, by incorporating AM-14 in a formulation described herein followed by sterilization microfiltration. In the specific embodiment of sterile powders for the preparation of sterile injectable solutions, particularly useful methods of preparation include, for example, vacuum drying and freeze-drying (lyophilization) as described previously. Such drying methods will yield a powder of the one or more biopharmaceuticals together with any additional desired components from a previously sterile-filtered solution thereof.

Embodiments include pharmaceutical containers comprising a vessel and/or vessel means and a pharmaceutical formulation of AM-14 as disclosed herein. A vessel and/or vessel means is something that holds the pharmaceutical formulation of AM-14 and can be any suitable vessel known in the art, including, but not limited to a vial, bottle, syringe, or any of a variety of formats well known in the art for packaging pharmaceutical formulations, including subcutaneous and transdermal delivery devices. The syringe may be filled with a pharmaceutical formulation of AM-14 as disclosed herein prior to distribution to end users (i.e. "prefilled syringe").

Embodiments of the invention include a prefilled syringe containing a pharmaceutical formulation of AM-14 as disclosed herein, wherein the prefilled syringe is in the form of an "autoinjector," such as but not limited to SureClick®, EverGentle®, Avanti®, DosePro®, and Leva®, or a version thereof. Embodiments of the invention include a prefilled syringe containing AM-14 at about 140 mg/mL formulated with 10 mM glutamic acid, 3% (w/v) L-proline, 0.01% (w/v) polysorbate 20, pH 4.8±0.2 in the form of an "autoinjector," such as but not limited to SureClick®, EverGentle®, Avanti®, DosePro®, and Leva®, or a version thereof. Embodiments of the invention include a prefilled syringe containing a pharmaceutical formulation of AM-14 as disclosed herein, wherein the prefilled syringe is in the form of any suitable micro-infusion pump known in the art. Embodiments of the invention include a prefilled syringe in the form of a micro-infusion pump containing AM-14 at about 140 mg/mL, formulated with 10 mM glutamic acid, 3% (w/v) L-proline, 0.01% (w/v) polysorbate 20, pH 4.8±0.2. A "microinfuser" is any micro-infusion pump for subcutaneous drug delivery. Embodiments of the invention include transdermal delivery of a pharmaceutical formulation of AM-14 as disclosed herein. Embodiments of the invention include any transdermal delivery system containing AM-14 at about 140 mg/mL, formulated with 10 mM glutamic acid, 3% (w/v) L-proline, 0.01% (w/v) polysorbate 20, pH 4.8±0.2.

Kits are also embodiments of the invention and comprise one or more pharmaceutical containers of AM-14 described in the preceding paragraphs together with instructions on the use of AM-14. It is understood the kit may contain other components.

II. Formulations, Dosage and Treatment Regimens

AM-14 in a pharmaceutical composition comprising AM-14 at about 100-150 mg/mL formulated with 10 mM glutamic acid, 3% (w/v) L-proline, 0.01% (w/v) polysorbate 20, pH 4.8±0.2, and in particular AM-14 in a pharmaceutical composition comprising AM-14 at about 140 mg/mL formulated with 10 mM glutamic acid, 3% (w/v) L-proline, 0.01% (w/v) polysorbate 20, pH 4.8±0.2 may be used to treat adult, juvenile, and/or pediatric patient populations having diseases including, but are not limited to, IL-17-related inflammation, IL-17-related autoimmune disease, IL-17-related cartilage inflammation and/or bone degradation, arthritis, rheumatoid arthritis, SEA Syndrome (Seronegativity, Enthesopathy, Arthropathy Syndrome), pauciarticular rheumatoid arthritis, polyarticular rheumatoid arthritis, systemic onset rheumatoid arthritis, ankylosing spondylitis, enteropathic arthritis, reactive arthritis, Reiter's Syndrome, dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus, Graves' disease, Addison's disease, Raynaud's phenomenon, autoimmune hepatitis, GVHD, pernicious anemia, vitiligo, Kawasaki's Disease, ANCA-associated vasculitides, pemphigus bullous pemphigoid, autoimmune ovarian failure, Hashimoto's thyroiditis, uveitis, thrombotic thrombocytopenic, purpura, hemolytic uremic syndrome, periodic fever syndromes, familial mediterranean fever, TNF receptor-1 associated periodic syndrome, hyper-IgD syndrome, Marshall's syndrome, cryopyrin-associated periodic syndromes, PAPA (Pyogenic arthritis, pyoderma gangrenosum, and acne) syndrome, Blau syndrome, interstitial pneumonias (such as usual interstitial pneumonia, desquamative interstitial pneumonia, respiratory bronchiolitis associated interstitial lung disease, acute interstitial pneumonia, nonspecific interstitial pneumonia, lymphocytic interstitial pneumonia, cryptogenic organizing pneumonitis), pulmonary fibrosis, fibrosing syndromes (such as scleredema, scleromyxedema, overlap syndromes, nephrogenic systemic fibrosis, amyloidosis, eosinophilic fasciitis, chronic graft-versus-host disease, drug-induced scleroderma, and environmental exposure fibrosis), neutrophilic dermatoses (such as, pyoderma gangrenosum, SAPHO (synovitis, acne, pustulosis, hyperostosis, and osteitis) syndrome, palmoplantar pustulosis, subcorneal pustular dermatosis, bowel-associated dermatosis-arthritis syndrome, Behcet's disease, neutrophilic dermatoses associated with rheumatoid arthritis, rheumatoid neutrophilic dermatosis, neutrophilic eccrine hidradenitis, and neutrophilic dermatosis of the dorsal hands), sepsis/SIRS, post-cardiac injury syndrome, and Dressler's Syndrome, idiopathic arthritis, and the like.

AM-14 in a pharmaceutical composition comprising AM-14 at about 140 mg/mL formulated with 10 mM glutamic acid, 3% (w/v) L-proline, 0.01% (w/v) polysorbate 20, pH 4.8±0.2 may be used to treat adult, juvenile, and/or pediatric patient populations having diseases including, but are not limited to, IL-17-related inflammation, IL-17-related autoimmune disease, IL-17-related cartilage inflammation and/or bone degradation, arthritis, rheumatoid arthritis, ankylosing spondylitis, psoriatic arthritis, scleroderma, psoriasis, plaque psoriasis, guttate psoriasis, dermatitis, atopic dermatitis, inflammatory bowel disease (IBD), Crohn's disease, ulcerative colitis, celiac disease, multiple sclerosis (MS), asthma, and COPD.

AM-14 in a pharmaceutical composition comprising AM-14 at about 140 mg/mL formulated with 10 mM glutamic acid, 3% (w/v) L-proline, 0.01% (w/v) polysorbate 20, pH 4.8±0.2 may be used to treat adult, juvenile, and/or pediatric patient populations having diseases including, but are not limited to, rheumatoid arthritis, ankylosing spondylitis, psoriatic arthritis, psoriasis, plaque psoriasis, Crohn's disease, multiple sclerosis (MS), and asthma.

As described in Examples 2 and 6, AM-14 shows efficacy in treating psoriasis in human patients. Examples 2 and 6 provide clinical evidence of AM-14's efficacy in treating psoriasis in human patients having psoriasis, and in particular, plaque psoriasis. Subcutaneous and intravenous administration of AM-14 significantly reduced the symptoms of psoriasis. Example 2 describes the reduction in psoriatic symptoms, as measured by the art-accepted PASI scoring system. Tables 2.9, 2.9, 2.10, and 2.11 show PASI scores and % PASI (i.e., % reduction in PASI score).

Figure 12:
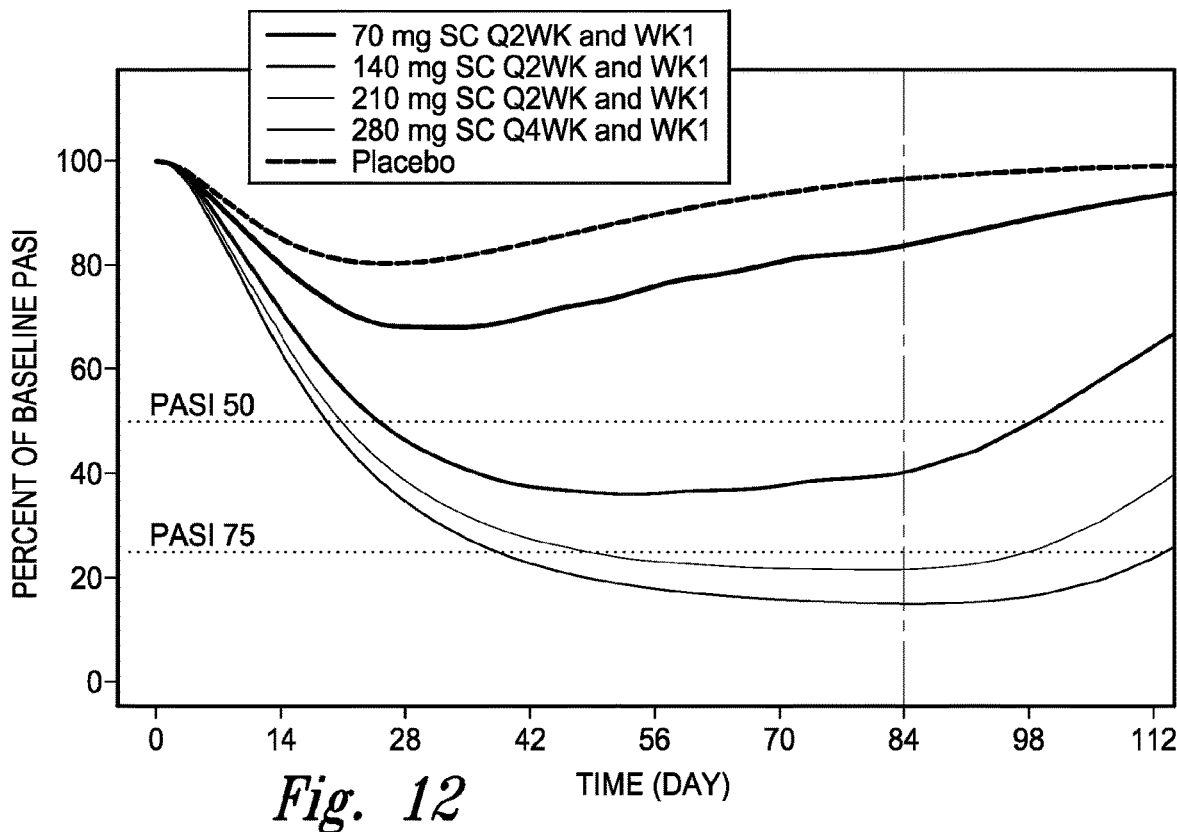
FIG. 12: A graphical depiction of the predicted mean PASI response time course for multiple dose scenarios (including placebo).
Figure 13:
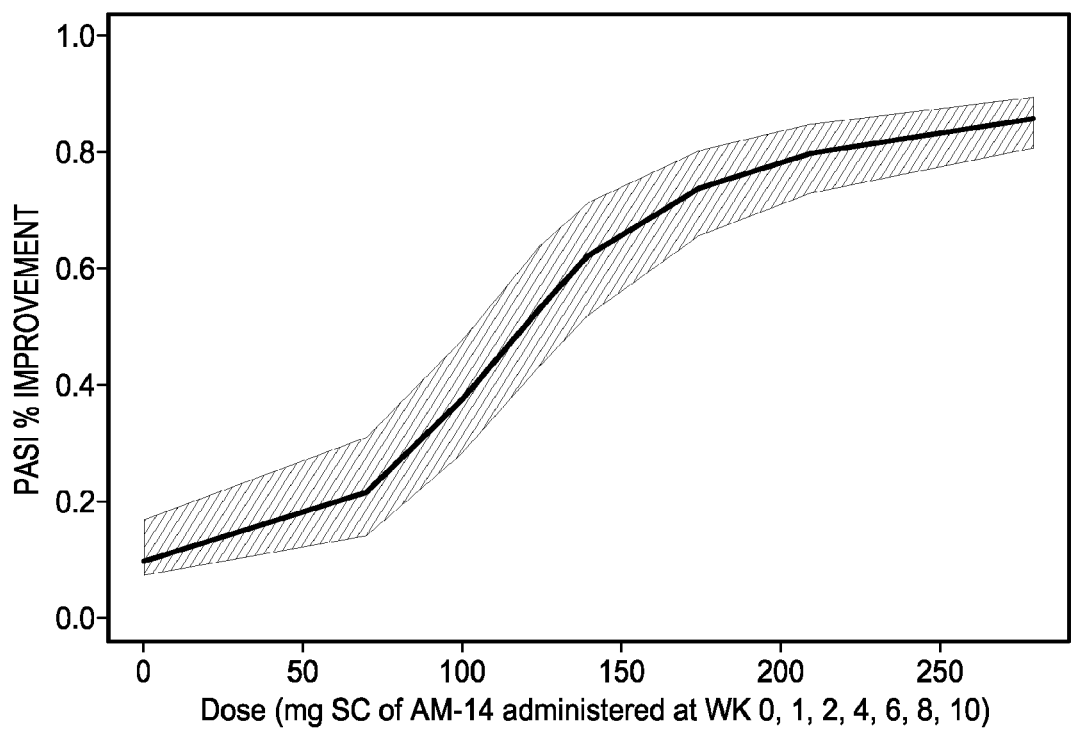
FIG. 13: A graphical depiction of the predicted week 12 median percent PASI improvement (dose-response curve) for AM-14, with 90% confidence interval shaded; for various dose levels each administered SC at week 0, 1, 2, 4, 6, 8, and 10.

Furthermore, sophisticated PK-PD modeling was performed based on the data from the Phase 1 psoriasis study (see Example 2). The predictive model correlated very closely to the actual PASI response data (see FIG. 11), which substantiates the validity of predicting efficacy for various doses. In addition, FIG. 12 shows the predicted time course of mean PASI response for four multiple dose scenarios (over 12 weeks) including placebo effect based on the model developed from single dose data. The modeled placebo response was assumed to act after only the first dose. The mean response for the 140 mg SC dose (at WK 0, 1, 2, 4, 6, 8, 10) was expected to exceed 50% PASI improvement for much of the study period including the 12 week (day 84) primary efficacy endpoint. The mean response for the 210 and 280 mg SC doses (at WK 0, 1, 2, 4, 6, 8, 10) was expected to exceed 75% PASI improvement for much of the study period including the 12 week (day 84) primary efficacy endpoint. And finally, FIG. 13 depicts the predicted week 12 median percent PASI improvement (dose-response curve) for AM-14, with 90% confidence interval shaded; for various dose levels each administered SC at week 0, 1, 2, 4, 6, 8, and 10.

Example 6 describes a Phase 2 study wherein AM-14 showed remarkable efficacy in treating psoriasis. Subjects received 70, 140, or 210 mg AM-14 at day 1 and weeks 1, 2, 4, 6, 8, and 10 or 280 mg at day 1 and weeks 4 and 8. AM-14 showed the following PASI responses at week 12: 70 mg dosing achieved a 33.3% PASI 75 response; 70 mg dosing achieved a 17.9% PASI 90 response; 70 mg dosing achieved a 10.3% PASI 100 response; 140 mg dosing achieved a 76.9% PASI 75 response; 140 mg dosing achieved a 71.8% PASI 90 response; 140 mg dosing achieved a 38.5% PASI 100 response; 210 mg dosing achieved a 82.5% PASI 75 response; 210 mg dosing achieved a 75.0% PASI 90 response; 210 mg dosing achieved a 62.5% PASI 100 response; 280 mg dosing achieved a 66.7% PASI 75 response; 280 mg dosing achieved a 57.1% PASI 90 response; and 280 mg dosing achieved a 28.6% PASI 100 response. Therefore, administration of AM-14 at the dosages and administration schedules described herein may be used to reduce the PASI score in a patient having psoriasis by at least 10, 15, 20, 25, 30, 35, 40, 45, 50, 55, 60, 65, 70, 75, 80, 85, 90, 95, or 100%.

Based on all these findings, AM-14 can be used to treat the various forms of psoriasis disclosed above, and in particular plaque psoriasis, in adult and/or juvenile patients at a dose range of 70 to 1,000 mg per dose, and in particular a dose range of 70 to 700 mg per dose. AM-14 can be used to treat psoriasis, and in particular plaque psoriasis, in adult and/or juvenile patients having psoriasis at a dose range of about 140 to about 300 mg per dose. AM-14 can be used to treat psoriasis, and in particular plaque psoriasis, in adult and/or juvenile patients having psoriasis at a dose of 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, and or 1,000 mg per dose.

AM-14 can be used to treat psoriasis in adult and/or juvenile patients having psoriasis, and in particular plaque psoriasis, with multiple dosing at a dose of 70 mg per dose. AM-14 can be used to treat psoriasis in adult and/or juvenile patients having psoriasis, and in particular plaque psoriasis, with multiple dosing at a dose of 140 mg per dose. AM-14 can be used to treat psoriasis in adult and/or juvenile patients having psoriasis, and in particular plaque psoriasis, with multiple dosing at a dose of 210 mg per dose. AM-14 can be used to treat psoriasis in adult and/or juvenile patients having psoriasis, and in particular plaque psoriasis, with multiple dosing at a dose of 280 mg per dose.

AM-14 can be used to treat psoriasis in adult and/or juvenile patients having psoriasis, and in particular plaque psoriasis, with multiple dosing at a dose of 70 mg per dose delivered by subcutaneous injection. AM-14 can be used to treat psoriasis in adult and/or juvenile patients having psoriasis, and in particular plaque psoriasis, with multiple dosing at a dose of 140 mg per dose delivered by subcutaneous injection. AM-14 can be used to treat psoriasis in adult and/or juvenile patients having psoriasis, and in particular plaque psoriasis, with multiple dosing at a dose of 210 mg per dose delivered by subcutaneous injection. AM-14 can be used to treat psoriasis in adult and/or juvenile patients having psoriasis, and in particular plaque psoriasis, with multiple dosing at a dose of 280 mg per dose delivered by subcutaneous injection.

AM-14 can be used to treat psoriasis in adult and/or juvenile patients having psoriasis, and in particular plaque psoriasis, at a dose of 70 mg per dose delivered by subcutaneous injection administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 140 mg per dose delivered by subcutaneous injection administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 210 mg per dose delivered by subcutaneous injection administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 280 mg per dose delivered by subcutaneous injection administered at time "0" (the first administration), at one week post time "0", and then administered every two weeks following the week one administration.

AM-14 can be used to treat psoriasis in adult and/or juvenile patients having psoriasis, and in particular plaque psoriasis, at a dose of 70 mg per dose delivered by subcutaneous injection administered at time "0" (the first administration), at one week post time "0", and then administered monthly following the week one administration. AM-14 can be used to treat psoriasis in adult and/or juvenile patients having psoriasis, and in particular plaque psoriasis, at a dose of 140 mg per dose delivered by subcutaneous injection administered at time "0" (the first administration), at one week post time "0", and then administered monthly following the week one administration. AM-14 can be used to treat psoriasis in adult and/or juvenile patients having psoriasis, and in particular plaque psoriasis, at a dose of 210 mg per dose delivered by subcutaneous injection administered at time "0" (the first administration), at one week post time "0", and then administered monthly following the week one administration. AM-14 can be used to treat psoriasis in adult and/or juvenile patients having psoriasis, and in particular plaque psoriasis, at a dose of 280 mg per dose delivered by subcutaneous injection administered at time "0" (the first administration), at one week post time "0", and then administered monthly following the week one administration.

AM-14 can be used to treat psoriasis in adult and/or juvenile patients having psoriasis, and in particular plaque psoriasis, with multiple dosing at a dose of 70 mg per dose delivered by subcutaneous injection by syringe. AM-14 can be used to treat psoriasis in adult and/or juvenile patients having psoriasis, and in particular plaque psoriasis, with multiple dosing at a dose of 140 mg per dose delivered by subcutaneous injection by syringe. AM-14 can be used to treat psoriasis in adult and/or juvenile patients having psoriasis, and in particular plaque psoriasis, with multiple dosing at a dose of 210 mg per dose delivered by subcutaneous injection by syringe. AM-14 can be used to treat psoriasis in adult and/or juvenile patients having psoriasis, and in particular plaque psoriasis, with multiple dosing at a dose of 280 mg per dose delivered by subcutaneous injection by syringe.

AM-14 can be used to treat psoriasis in adult and/or juvenile patients having psoriasis, and in particular plaque psoriasis, at a dose of 70 mg per dose delivered by subcutaneous injection by syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 140 mg per dose delivered by subcutaneous injection by syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 210 mg per dose delivered by subcutaneous injection by syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 280 mg per dose delivered by subcutaneous injection by syringe administered at time "0" (the first administration), at one week post time "0", and then administered every two weeks following the week one administration.

AM-14 can be used to treat psoriasis in adult and/or juvenile patients having psoriasis, and in particular plaque psoriasis, at a dose of 70 mg per dose delivered by subcutaneous injection by syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 140 mg per dose delivered by subcutaneous injection by syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 210 mg per dose delivered by subcutaneous injection by syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 280 mg per dose delivered by subcutaneous injection by syringe administered at time "0" (the first administration), at one week post time "0", and then administered monthly following the week one administration.

AM-14 can be used to treat psoriasis in adult and/or juvenile patients having psoriasis, and in particular plaque psoriasis, with multiple dosing at a dose of 70 mg per dose delivered by subcutaneous injection by autoinjector syringe. AM-14 can be used to treat psoriasis in adult and/or juvenile patients having psoriasis, and in particular plaque psoriasis, with multiple dosing at a dose of 140 mg per dose delivered by subcutaneous injection by autoinjector syringe. AM-14 can be used to treat psoriasis in adult and/or juvenile patients having psoriasis, and in particular plaque psoriasis, with multiple dosing at a dose of 210 mg per dose delivered by subcutaneous injection by autoinjector syringe. AM-14 can be used to treat psoriasis in adult and/or juvenile patients having psoriasis, and in particular plaque psoriasis, with multiple dosing at a dose of 280 mg per dose delivered by subcutaneous injection by autoinjector syringe.

AM-14 can be used to treat psoriasis in adult and/or juvenile patients having psoriasis, and in particular plaque psoriasis, at a dose of 70 mg per dose delivered by subcutaneous injection by autoinjector syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 140 mg per dose delivered by subcutaneous injection by autoinjector syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 210 mg per dose delivered by subcutaneous injection by autoinjector syringe administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 280 mg per dose delivered by subcutaneous injection by autoinjector syringe administered at time "0" (the first administration), at one week post time "0", and then administered every two weeks following the week one administration.

AM-14 can be used to treat psoriasis in adult and/or juvenile patients having psoriasis, and in particular plaque psoriasis, at a dose of 70 mg per dose delivered by subcutaneous injection by autoinjector syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 140 mg per dose delivered by subcutaneous injection by autoinjector syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 210 mg per dose delivered by subcutaneous injection by autoinjector syringe administered at time "0" (the first administration), at one week post time "0", and then administered monthly following the week one administration. AM-14 can be used to treat psoriasis in adult and/or juvenile patients having psoriasis, and in particular plaque psoriasis, at a dose of 280 mg per dose delivered by subcutaneous injection by autoinjector syringe administered at time "0" (the first administration), at one week post time "0", and then administered monthly following the week one administration.

AM-14 can be used to treat psoriasis in adult and/or juvenile patients having psoriasis, and in particular plaque psoriasis, with at least one dose at a dose of 70 mg per dose delivered by subcutaneous injection by microinfuser. AM-14 can be used to treat psoriasis in adult and/or juvenile patients having psoriasis, and in particular plaque psoriasis, with at least one dose at a dose of 140 mg per dose delivered by subcutaneous injection by microinfuser. AM-14 can be used to treat psoriasis in adult and/or juvenile patients having psoriasis, and in particular plaque psoriasis, with at least one dose at a dose of 210 mg per dose delivered by subcutaneous injection by microinfuser. AM-14 can be used to treat psoriasis in adult and/or juvenile patients having psoriasis, and in particular plaque psoriasis, with at least one dose at a dose of 280 mg per dose delivered by subcutaneous injection by microinfuser.

AM-14 can be used to treat psoriasis in adult and/or juvenile patients having psoriasis, and in particular plaque psoriasis, at a dose of 70 mg per dose delivered by subcutaneous injection by microinfuser administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 140 mg per dose delivered by subcutaneous injection by microinfuser administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 210 mg per dose delivered by subcutaneous injection by microinfuser administered at time "0" (the first administration), at one week post time "0", and then administered every two weeks following the week one administration. AM-14 can be used to treat psoriasis in adult and/or juvenile patients having psoriasis, and in particular plaque psoriasis, at a dose of 280 mg per dose delivered by subcutaneous injection by microinfuser administered at time "0" (the first administration), at one week post time "0", and then administered every two weeks following the week one administration.

AM-14 can be used to treat psoriasis in adult and/or juvenile patients having psoriasis, and in particular plaque psoriasis, at a dose of 70 mg per dose delivered by subcutaneous injection by microinfuser administered at time "0" (the first administration), at one week post time "0", and then administered monthly following the week one administration. AM-14 can be used to treat psoriasis in adult and/or juvenile patients having psoriasis, and in particular plaque psoriasis, at a dose of 140 mg per dose delivered by subcutaneous injection by microinfuser administered at time "0" (the first administration), at one week post time "0", and then administered monthly following the week one administration. AM-14 can be used to treat psoriasis in adult and/or juvenile patients having psoriasis, and in particular plaque psoriasis, at a dose of 210 mg per dose delivered by subcutaneous injection by microinfuser administered at time "0" (the first administration), at one week post time "0", and then administered monthly following the week one administration. AM-14 can be used to treat psoriasis in adult and/or juvenile patients having psoriasis, and in particular plaque psoriasis, at a dose of 280 mg per dose delivered by subcutaneous injection by microinfuser administered at time "0" (the first administration), at one week post time "0", and then administered monthly following the week one administration.

AM-14 can be used to treat adult and/or juvenile patients with chronic moderate to severe plaque psoriasis who are candidates for systemic therapy or phototherapy with multiple dosing at a dose of 70 mg per dose. AM-14 can be used to treat adult and/or juvenile patients with chronic moderate to severe plaque psoriasis who are candidates for systemic therapy or phototherapy with multiple dosing at a dose of 140 mg per dose. AM-14 can be used to treat adult and/or juvenile patients with chronic moderate to severe plaque psoriasis who are candidates for systemic therapy or phototherapy with multiple dosing at a dose of 210 mg per dose. AM-14 can be used to treat adult and/or juvenile patients with chronic moderate to severe plaque psoriasis who are candidates for systemic therapy or phototherapy with multiple dosing at a dose of 280 mg per dose. AM-14 can be used to treat adult and/or juvenile patients with chronic moderate to severe plaque psoriasis who are candidates for systemic therapy or phototherapy with multiple dosing at a dose of 70 mg per dose delivered by subcutaneous injection. AM-14 can be used to treat adult and/or juvenile patients with chronic moderate to severe plaque psoriasis who are candidates for systemic therapy or phototherapy with multiple dosing at a dose of 140 mg per dose delivered by subcutaneous injection. AM-14 can be used to treat adult and/or juvenile patients with chronic moderate to severe plaque psoriasis who are candidates for systemic therapy or phototherapy with multiple dosing at a dose of 210 mg per dose delivered by subcutaneous injection. AM-14 can be used to treat adult and/or juvenile patients with chronic moderate to severe plaque psoriasis who are candidates for systemic therapy or phototherapy with multiple dosing at a dose of 280 mg per dose delivered by subcutaneous injection.

AM-14 can be used to treat adult and/or juvenile patients with chronic moderate to severe plaque psoriasis who are candidates for systemic therapy or phototherapy at a dose of 70 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection administered at time "0" (the first administration), at one week post time "0", and then administered every two weeks following the week one administration.

AM-14 can be used to treat adult and/or juvenile patients with chronic moderate to severe plaque psoriasis who are candidates for systemic therapy or phototherapy at a dose of 70 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection administered at time "0" (the first administration), at one week post time "0", and then administered monthly following the week one administration.

AM-14 can be used to treat adult and/or juvenile patients with chronic moderate to severe plaque psoriasis who are candidates for systemic therapy or phototherapy with multiple dosing at a dose of 70 mg per dose delivered by subcutaneous injection by syringe. AM-14 can be used to treat adult and/or juvenile patients with chronic moderate to severe plaque psoriasis who are candidates for systemic therapy or phototherapy with multiple dosing at a dose of 140 mg per dose delivered by subcutaneous injection by syringe. AM-14 can be used to treat adult and/or juvenile patients with chronic moderate to severe plaque psoriasis who are candidates for systemic therapy or phototherapy with multiple dosing at a dose of 210 mg per dose delivered by subcutaneous injection by syringe. AM-14 can be used to treat adult and/or juvenile patients with chronic moderate to severe plaque psoriasis who are candidates for systemic therapy or phototherapy with multiple dosing at a dose of 280 mg per dose delivered by subcutaneous injection by syringe.

AM-14 can be used to treat adult and/or juvenile patients with chronic moderate to severe plaque psoriasis who are candidates for systemic therapy or phototherapy at a dose of 70 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by syringe administered at time "0" (the first administration), at one week post time "0", and then administered every two weeks following the week one administration.

AM-14 can be used to treat adult and/or juvenile patients with chronic moderate to severe plaque psoriasis who are candidates for systemic therapy or phototherapy at a dose of 70 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by syringe administered at time "0" (the first administration), at one week post time "0", and then administered monthly following the week one administration.

AM-14 can be used to treat adult and/or juvenile patients with chronic moderate to severe plaque psoriasis who are candidates for systemic therapy or phototherapy with multiple dosing at a dose of 70 mg per dose delivered by subcutaneous injection by autoinjector syringe. AM-14 can be used to treat adult and/or juvenile patients with chronic moderate to severe plaque psoriasis who are candidates for systemic therapy or phototherapy with multiple dosing at a dose of 140 mg per dose delivered by subcutaneous injection by autoinjector syringe. AM-14 can be used to treat adult and/or juvenile patients with chronic moderate to severe plaque psoriasis who are candidates for systemic therapy or phototherapy with multiple dosing at a dose of 210 mg per dose delivered by subcutaneous injection by autoinjector syringe. AM-14 can be used to treat adult and/or juvenile patients with chronic moderate to severe plaque psoriasis who are candidates for systemic therapy or phototherapy with multiple dosing at a dose of 280 mg per dose delivered by subcutaneous injection by autoinjector syringe.

AM-14 can be used to treat adult and/or juvenile patients with chronic moderate to severe plaque psoriasis who are candidates for systemic therapy or phototherapy at a dose of 70 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by autoinjector syringe administered at time "0" (the first administration), at one week post time "0", and then administered every two weeks following the week one administration.

AM-14 can be used to treat adult and/or juvenile patients with chronic moderate to severe plaque psoriasis who are candidates for systemic therapy or phototherapy at a dose of 70 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by autoinjector syringe administered at time "0" (the first administration), at one week post time "0", and then administered monthly following the week one administration.

AM-14 can be used to treat adult and/or juvenile patients with chronic moderate to severe plaque psoriasis who are candidates for systemic therapy or phototherapy with multiple dosing at a dose of 70 mg per dose delivered by subcutaneous injection by microinfuser. AM-14 can be used to treat adult and/or juvenile patients with chronic moderate to severe plaque psoriasis who are candidates for systemic therapy or phototherapy with multiple dosing at a dose of 140 mg per dose delivered by subcutaneous injection by microinfuser. AM-14 can be used to treat adult and/or juvenile patients with chronic moderate to severe plaque psoriasis who are candidates for systemic therapy or phototherapy with multiple dosing at a dose of 210 mg per dose delivered by subcutaneous injection by microinfuser. AM-14 can be used to treat adult and/or juvenile patients with chronic moderate to severe plaque psoriasis who are candidates for systemic therapy or phototherapy with multiple dosing at a dose of 280 mg per dose delivered by subcutaneous injection by microinfuser.

AM-14 can be used to treat adult and/or juvenile patients with chronic moderate to severe plaque psoriasis who are candidates for systemic therapy or phototherapy at a dose of 70 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by microinfuser administered at time "0" (the first administration), at one week post time "0", and then administered every two weeks following the week one administration.

AM-14 can be used to treat adult and/or juvenile patients with chronic moderate to severe plaque psoriasis who are candidates for systemic therapy or phototherapy at a dose of 70 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 140 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 210 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who are candidates for systemic therapy or phototherapy at a dose of 280 mg per dose delivered by subcutaneous injection by microinfuser administered at time "0" (the first administration), at one week post time "0", and then administered monthly following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose.

AM-14 can be used to adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection administered at time "0" (the first administration), at one week post time "0", and then administered every two weeks following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection administered at time "0" (the first administration), at one week post time "0", and then administered monthly following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection by syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection by syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection by syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection by syringe.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by syringe administered at time "0" (the first administration), at one week post time "0", and then administered every two weeks following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by syringe administered at time "0" (the first administration), at one week post time "0", and then administered monthly following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection by autoinjector syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection by autoinjector syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection by autoinjector syringe. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection by autoinjector syringe.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by autoinjector syringe administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by auto-injector syringe administered at time "0" (the first administration), at one week post time "0", and then administered every two weeks following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by autoinjector syringe administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by autoinjector syringe administered at time "0" (the first administration), at one week post time "0", and then administered monthly following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection by microinfuser. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection by microinfuser. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection by microinfuser. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection by microinfuser.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by microinfuser administered at time "0" (the first administration), at one week post time "0", and then administered every two weeks following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by microinfuser administered at time "0" (the first administration), at one week post time "0", and then administered every two weeks following the week one administration.

AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by microinfuser administered at time "0" (the first administration), at one week post time "0", and then administered monthly following the week one administration. AM-14 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by microinfuser administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 70 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 140 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 210 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 280 mg per dose.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 70 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 140 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 210 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 280 mg per dose delivered by subcutaneous injection.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile psoriasis in patients having psoriasis, and in particular plaque psoriasis, at a dose of 70 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 70 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 140 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 210 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 280 mg per dose delivered by subcutaneous injection by syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in patients having psoriasis, and in particular plaque psoriasis, at a dose of 210 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 70 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 140 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 210 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 280 mg per dose delivered by subcutaneous injection by autoinjector syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by autoinjector syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 70 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 140 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 210 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, with multiple dosing at a dose of 280 mg per dose delivered by subcutaneous injection by microinfuser.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 70 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 140 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 210 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, at a dose of 280 mg per dose delivered by subcutaneous injection by microinfuser administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 70 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 140 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 210 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 280 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 70 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 140 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 210 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 280 mg per dose delivered by subcutaneous injection.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 70 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 140 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 210 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 280 mg per dose delivered by subcutaneous injection by syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 70 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 140 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 210 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with multiple dosing at a dose of 280 mg per dose delivered by subcutaneous injection by autoinjector syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to therapy or phototherapy at a dose of 140 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by autoinjector syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with at least one dose at a dose of 70 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with at least one dose at a dose of 140 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with at least one dose at a dose of 210 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy with at least one dose at a dose of 280 mg per dose delivered by subcutaneous injection by microinfuser.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 70 mg per dose delivered by subcutaneous injection by microinfuser administered at time "0"

(the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 140 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 210 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy at a dose of 280 mg per dose delivered by subcutaneous injection by microinfuser administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection by syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection by syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 70 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 140 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 210 mg per dose delivered by subcutaneous injection by autoinjector syringe. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with multiple dosing at a dose of 280 mg per dose delivered by subcutaneous injection by autoinjector syringe.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by autoinjector syringe administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v)

polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by autoinjector syringe administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by autoinjector syringe administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with at least one dose at a dose of 70 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with at least one dose at a dose of 140 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with at least one dose at a dose of 210 mg per dose delivered by subcutaneous injection by microinfuser. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) with at least one dose at a dose of 280 mg per dose delivered by subcutaneous injection by microinfuser.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by microinfuser administered at time "0" (the first administration), at one week post time "0", and then administered every two weeks following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 70 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 140 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 210 mg per dose delivered by subcutaneous injection by microinfuser administered at time "0" (the first administration), at one week post time "0", and then administered monthly following the week one administration. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy) at a dose of 280 mg per dose delivered by subcutaneous injection by microinfuser administered at time "0" (the first administration), at one week post time "0", and then administered monthly following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg every two weeks and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose every two weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose every two weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose every two weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose every two weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose every two weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 90 kg and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose every four weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection to patients weighing less than or approximately equal to 90 kg every two weeks and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection every two weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection every two weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection every two weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection every two weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose by subcutaneous injection every two weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 90 kg and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose by subcutaneous injection every four weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe to patients weighing less than or approximately equal to 90 kg every two weeks and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe every two weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe every two weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe every two weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-praline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe every two weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by autoinjector syringe every two weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 90 kg and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by autoinjector syringe every four weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser to patients weighing less than or approximately equal to 90 kg every two weeks and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser every two weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser every two weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser every two weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser every two weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose delivered by subcutaneous injection by microinfuser every two weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 90 kg and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose delivered by subcutaneous injection by microinfuser every four weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 100 kg and patients weighing greater than 100 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in patients having psoriasis, and in particular plaque psoriasis, wherein said patients are administered a 140 mg dose to patients weighing less than or approximately equal to 100 kg and patients weighing greater than 100 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-praline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-praline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 210 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 100 kg and patients weighing greater than 100 kg are administered a 210 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 210 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 280 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 100 kg and patients weighing greater than 100 kg are administered a 280 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 280 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose to patients weighing less than or approximately equal to 90 kg and patients weighing greater than 90 kg are administered a 210 mg dose, wherein the AM-14 is administered by subcutaneous injection by auto-injector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by autoinjector syringe a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v)

polysorbate 20, pH 4.8±0.2 can be used to treat psoriasis in adult and/or juvenile patients having psoriasis, and in particular plaque psoriasis, wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 100 kg and patients weighing greater than 100 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 90 kg and patients weighing greater than 90 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 100 kg and patients weighing greater than 100 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 140 mg dose to patients weighing less than or approximately equal to 110 kg and patients weighing greater than 110 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered a 280 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by microinfuser a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks. AM-14 in a formulation comprising 140 mg/mL AM-14, 10 mM glutamic acid, 3% (w/v) L-proline, 0.01% (w/v) polysorbate 20, pH 4.8±0.2 can be used to treat psoriasis in adult and/or juvenile patients having psoriasis, and in particular plaque psoriasis, wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg every two weeks and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose every two weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose every two weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose every two weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose every two weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose every two weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 90 kg and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose every four weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection to patients weighing less than or approximately equal to 90 kg every two weeks and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection every two weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection every two weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection every two weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection every two weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose by subcutaneous injection every two weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 90 kg and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose by subcutaneous injection every four weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe to patients weighing less than or approximately equal to 90 kg every two weeks and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe every two weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe every two weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe every two weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe every two weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by autoinjector syringe every two weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 90 kg and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by autoinjector syringe every four weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser to patients weighing less than or approximately equal to 90 kg every two weeks and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser every two weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser every two weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser every two weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser every two weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose delivered by subcutaneous injection by microinfuser every two weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 90 kg and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose delivered by subcutaneous injection by microinfuser every four weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose to patients weighing less than or approximately equal to 90 kg and patients weighing greater than 90 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by autoinjector syringe a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 90 kg and patients weighing greater than 90 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 100 kg and patients weighing greater than 100 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 140 mg dose to patients weighing less than or approximately equal to 110 kg and patients weighing greater than 110 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered a 280 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by microinfuser a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who are candidates for systemic therapy or phototherapy, wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg every two weeks and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose every two weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose every two weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose every two weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose every two weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose every two weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 90 kg and patients weighing greater than 90 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 100 kg and patients weighing greater than 100 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 110 kg and patients weighing greater than 110 kg are administered a 210 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 90 kg and patients weighing greater than 90 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 100 kg and patients weighing greater than 100 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose every four weeks to patients weighing less than or approximately equal to 110 kg and patients weighing greater than 110 kg are administered a 280 mg dose every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection to patients weighing less than or approximately equal to 90 kg every two weeks and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection every two weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection every two weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection every two weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection every two weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose by subcutaneous injection every two weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 90 kg and patients weighing greater than 90 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 100 kg and patients weighing greater than 100 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 110 kg and patients weighing greater than 110 kg are administered a 210 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 90 kg and patients weighing greater than 90 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 100 kg and patients weighing greater than 100 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose by subcutaneous injection every four weeks to patients weighing less than or approximately equal to 110 kg and patients weighing greater than 110 kg are administered a 280 mg dose by subcutaneous injection every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe to patients weighing less than or approximately equal to 90 kg every two weeks and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe every two weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v)

polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe every two weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe every two weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe every two weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by autoinjector syringe every two weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 90 kg and patients weighing greater than 90 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 100 kg and patients weighing greater than 100 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 110 kg and patients weighing greater than 110 kg are administered a 210 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 90 kg and patients weighing greater than 90 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 100 kg and patients weighing greater than 100 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by autoinjector syringe every four weeks to patients weighing less than or approximately equal to 110 kg and patients weighing greater than 110 kg are administered a 280 mg dose delivered by subcutaneous injection by autoinjector syringe every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser to patients weighing less than or approximately equal to 90 kg every two weeks and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser every two weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser every two weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser every two weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser every two weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose delivered by subcutaneous injection by microinfuser every two weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 90 kg and patients weighing greater than 90 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 100 kg and patients weighing greater than 100 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 110 kg and patients weighing greater than 110 kg are administered a 210 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 90 kg and patients weighing greater than 90 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 100 kg and patients weighing greater than 100 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose delivered by subcutaneous injection by microinfuser every four weeks to patients weighing less than or approximately equal to 110 kg and patients weighing greater than 110 kg are administered a 280 mg dose delivered by subcutaneous injection by microinfuser every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 280 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose to patients weighing less than or approximately equal to 90 kg and patients weighing greater than 90 kg are administered a 210 mg dose, wherein the AM-14 is administered by subcutaneous injection administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 280 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose to patients weighing less than or approximately equal to 90 kg and patients weighing greater than 90 kg are administered a 210 mg dose, wherein the AM-14 is administered by subcutaneous injection by autoinjector syringe administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by autoinjector syringe a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by autoinjector syringe a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by autoinjector syringe a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 90 kg and patients weighing greater than 90 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 100 kg and patients weighing greater than 100 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 140 mg dose to patients weighing less than or approximately equal to 110 kg and patients weighing greater than 110 kg are administered a 280 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered a 280 mg dose to patients weighing less than or approximately equal to 90 kg and patients weighing greater than 90 kg are administered a 210 mg dose, wherein the AM-14 is administered by subcutaneous injection by microinfuser administered at time "0" (the first administration), at one week post time "0", and then administered every two weeks following the week one administration.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 210 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by microinfuser a 280 mg dose at time "0" (the first administration), at one week post time "0", and every four weeks to patients weighing less than or approximately equal to 90 kg, and patients weighing greater than 90 kg are administered a 280 mg dose at time "0" (the first administration), at one week post time "0", and every two weeks.

AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by microinfuser a 280 mg dose at time "0" (the first administration), at one week post time "0", and every four weeks to patients weighing less than or approximately equal to 100 kg, and patients weighing greater than 100 kg are administered a 280 mg dose at time "0" (the first administration), at one week post time "0", and every two weeks. AM-14 in a formulation comprising 140 mg/mL AM-14, 10 mM glutamic acid, 3% (w/v) L-proline, 0.01% (w/v) polysorbate 20, pH 4.8±0.2 can be used to treat adult and/or juvenile patients with chronic moderate to severe plaque psoriasis who fail to respond to, have a contraindication to, or are intolerant to other systemic therapies including cyclosporin, methotrexate, and PUVA (psoralen plus ultraviolet-A phototherapy), wherein said patients are administered by subcutaneous injection by microinfuser a 280 mg dose at time "0" (the first administration), at one week post time "0", and every four weeks to patients weighing less than or approximately equal to 110 kg, and patients weighing greater than 110 kg are administered a 280 mg dose at time "0" (the first administration), at one week post time "0", and every two weeks.

Administration and dosage regimens of AM-14 formulations can be adjusted to provide an effective amount for an optimum therapeutic response. For example, a single bolus can be administered, several divided doses can be administered over time or the dose can be proportionally reduced or increased as indicated by the exigencies of the therapeutic situation. AM-14 may be formulated for subcutaneous, intravenous, parenteral, intradermal, intramuscular, and/or intraperitoneal administration in a unit dosage form for ease of administration and uniformity of dosage. AM-14 formulated in 10 mM glutamic acid, 3% (w/v) L-proline, 0.01% (w/v) polysorbate 20, pH 4.8±0.2 may be formulated for subcutaneous, intravenous, parenteral, intradermal, intramuscular, and/or intraperitoneal administration in a unit dosage form for ease of administration and uniformity of dosage. Unit dosing refers to a physically discrete amount of AM-14 suited as unitary dosages for the subjects to be treated; each unit contains a predetermined quantity of active biopharmaceutical calculated to produce a desired therapeutic effect.

AM-14 formulations may be administered subcutaneously, intravenously, parenterally, intradermally, intramuscularly, and/or intraperitoneally using standard techniques. AM-14 may be administered subcutaneously, intravenously, parenterally, intradermally, intramuscularly, and/or intraperitoneally at the dosages described above and in the formulations described herein for the treatment of the diseases listed above. AM-14 formulated in 10 mM glutamic acid, 3% (w/v) L-proline, 0.01% (w/v) polysorbate 20, pH 4.8±0.2 may be administered subcutaneously, intravenously, parenterally, intradermally, intramuscularly, and/or intraperitoneally using standard techniques at the dosages and dosing regimens described above for the treatment of the psoriasis listed above. AM-14 formulated in 10 mM glutamic acid, 3% (w/v) L-proline, 0.01% (w/v) polysorbate 20, pH 4.8±0.2 may be administered subcutaneously, intravenously, intradermally, and/or intramuscularly using standard techniques at the dosages and dosing regimens described above for the treatment of the psoriasis listed above. AM-14 may be formulated at about 140 mg/ml formulated in 10 mM glutamic acid, 3% (w/v) L-proline, 0.01% (w/v) polysorbate 20, pH 4.8±0.2 may be administered subcutaneously, intravenously, intradermally, and/or intramuscularly using standard techniques at the dosages and dosing regimens described above for the treatment of the psoriasis listed above. AM-14 formulations, such as AM-14 formulated in 10 mM glutamic acid, 3% (w/v) L-proline, 0.01% (w/v) polysorbate 20, pH 4.8±0.2, may be administered more than once at scheduled intervals over a period of time. In certain embodiments, AM-14 formulations, such as AM-14 formulated in 10 mM glutamic acid, 3% (w/v) L-proline, 0.01% (w/v) polysorbate 20, pH 4.8±0.2, are administered over a period of at least a month or more. Embodiments include long-term treatment of the chronic conditions described above. Shorter periods of administration can be sufficient when treating acute conditions including, for example, from one to twenty four weeks. In general, AM-14 formulations are administered until the patient manifests a medically relevant degree of improvement over baseline for the chosen indicator or indicators as adjudged by a medical professional. Specifically, AM-14 formulations, such as AM-14 formulated in 10 mM glutamic acid, 3% (w/v) L-proline, 0.01% (w/v) polysorbate 20, pH 4.8±0.2, may be administered once every week or 6 to 8 days, or every two weeks or 12 to 16 days, or every three weeks or 19 to 23 days, or every month or 26 to 30 days, or every five weeks or 33 to 34 days, or every six weeks or 40 to 44 days, or every seven weeks or 47 to 51 days, or every two months or 54 to 58 days subcutaneously, intravenously, parenterally, intradermally, intramuscularly, and/or intraperitoneally at the dosages described above and in the formulations described herein for an indefinite period of time for the treatment of the diseases and conditions described above, and in particular psoriasis.

Aspects of the invention include dosing regimens that further comprise a loading step. A "loading dose" refers to the step of initially administering at least one dose of an AM-14 formulation to the patient by any of the routes described above and prior to the administration of the same or lower dose at any of the intervals and routes described above. The initial dose or doses rapidly increase the serum drug concentration to an efficacious target serum concentration. The loading dose or series of loading doses is/are administered 1, 2, 3, 4, 5, 6, 7, 8, 9, 10, 11, 12, 13, and/or 14 days prior to the normal course of dosing. It is understood that a "day" also includes any time interval between 1 and 24 hours. For example, as described above in more detail, AM-14 formulated in 10 mM glutamic acid, 3% (w/v) L-proline, 0.01% (w/v) polysorbate 20, pH 4.8±0.2, is administered at time "0" (the first administration), at one week post time "0", and then administered every two weeks following the week one administration.

It is understood that the methods of treating the diseases described herein would administer an effective amount of an AM-14 formulation, such as AM-14 formulated in 10 mM glutamic acid, 3% (w/v) L-proline, 0.01% (w/v) polysorbate 20, pH 4.8±0.2. Depending on the indication to be treated, a therapeutically effective amount is sufficient to cause a reduction in at least one symptom of the targeted pathological condition by at least about 5%, 10%, 15%, 20%, 25%, 30%, 35%, 40%, 45%, 50%, 55%, 60%, 65%, 70%, 75%, 80%, 85%, 90%, 95%, or more, relative to untreated subjects.

Aspects of the invention also include methods of regulating gene expression in psoriasis patients using AM-14. Example 3 describes in detail the genes that are regulated by AM-14. Thus, aspects of the invention include methods of regulating the genes in tables 3.1, 3.2, and/or 3.3 in psoriasis patients by administering AM-14. Aspects of the invention include the use of AM-14 for the preparation of a medicament for regulating the genes in tables 3.1, 3.2, and/or 3.3 in psoriasis patients. Further aspects described in Example 3 are also envisioned in methods of use, such as the temporal relationship between administration of AM-14 and gene regulation as well as the extent (e.g., fold change) of gene regulation and administration of AM-14.

Aspects of the invention also include methods of regulating gene expression in psoriasis patients using AM-14 and concomitantly reducing the PASI score in a patient having psoriasis by at least 10, 15, 20, 25, 30, 35, 40, 45, 50, 55, 60, 65, 70, 75, 80, 85, 90, 95, or 100%. Example 3 describes in detail the genes that are regulated by AM-14. Thus, aspects of the invention include methods of regulating the genes in tables 3.1, 3.2, and/or 3.3 and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients by administering AM-14. Aspects of the invention include the use of AM-14 for the preparation of a medicament for regulating the genes in tables 3.1, 3.2, and/or 3.3 and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients. Further aspects described in Example 3 are also envisioned in methods of use, such as the temporal relationship between administration of AM-14 and gene regulation as well as the extent (e.g., fold change) of gene regulation and administration of AM-14.

Aspects of the invention also include methods of regulating gene expression in 15 days or less in psoriasis patients using AM-14 and concomitantly reducing the PASI score in a patient having psoriasis by at least 10, 15, 20, 25, 30, 35, 40, 45, 50, 55, 60, 65, 70, 75, 80, 85, 90, 95, or 100%. Example 3 describes in detail the genes that are regulated by AM-14. Thus, aspects of the invention include methods of regulating the genes in tables 3.1, 3.2, and/or 3.3 in 15 days or less and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients by administering AM-14. Aspects of the invention include the use of AM-14 for the preparation of a medicament for regulating the genes in tables 3.1, 3.2, and/or 3.3 in 15 days or less and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients. Further aspects described in Example 3 are also envisioned in methods of use, such as the temporal relationship between administration of AM-14 and gene regulation as well as the extent (e.g., fold change) of gene regulation and administration of AM-14.

Aspects of the invention also include methods of regulating gene expression in psoriasis patients using IL-17 antagonistic antibodies. An "IL-17 antagonistic antibody" is an antibody that inhibits IL-17A or IL-17A/F from activating its cognate receptor(s) including IL-17RA, IL-17RC, and IL-17RA/RC. IL-17 antagonistic antibodies includes antibodies against IL-17RA or antibodies against IL-17A and/or IL-17A/F. Example 3 describes in detail the genes that are regulated by an exemplary antibody, AM-14. Thus, aspects of the invention include methods of regulating the genes in tables 3.1, 3.2, and/or 3.3 in psoriasis patients by administering an IL-17 antagonistic antibody. Aspects of the invention include the use of an IL-17 antagonistic antibody for the preparation of a medicament for regulating the genes in tables 3.1, 3.2, and/or 3.3 in psoriasis patients. Further aspects described in Example 3 are also envisioned in methods of use, such as the temporal relationship between administration of an IL-17 antagonistic antibody and gene regulation as well as the extent (e.g., fold change) of gene regulation and administration of an IL-17 antagonistic antibody.

Aspects of the invention also include methods of regulating gene expression and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients using IL-17 antagonistic antibodies. An "IL-17 antagonistic antibody" is an antibody that inhibits IL-17A or IL-17A/F from activating its cognate receptor(s) including IL-17RA, IL-17RC, and IL-17RA/RC. IL-17 antagonistic antibodies includes antibodies against IL-17RA or antibodies against IL-17A and/or IL-17A/F. Example 3 describes in detail the genes that are regulated by an exemplary antibody, AM-14. Thus, aspects of the invention include methods of regulating the genes in tables 3.1, 3.2, and/or 3.3 and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients by administering an IL-17 antagonistic antibody. Aspects of the invention include the use of an IL-17 antagonistic antibody for the preparation of a medicament for regulating the genes in tables 3.1, 3.2, and/or 3.3 and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients. Further aspects described in Example 3 are also envisioned in methods of use, such as the temporal relationship between administration of an IL-17 antagonistic antibody and gene regulation as well as the extent (e.g., fold change) of gene regulation and administration of an IL-17 antagonistic antibody.

Aspects of the invention also include methods of regulating gene expression in 15 days or less and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients using IL-17 antagonistic antibodies. An "IL-17 antagonistic antibody" is an antibody that inhibits IL-17A or IL-17A/F from activating its cognate receptor(s) including IL-17RA, IL-17RC, and IL-17RA/RC. IL-17 antagonistic antibodies includes antibodies against IL-17RA or antibodies against IL-17A and/or IL-17A/F. Example 3 describes in detail the genes that are regulated by an exemplary antibody, AM-14. Thus, aspects of the invention include methods of regulating the genes in tables 3.1, 3.2, and/or 3.3 in 15 days or less and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients by administering an IL-17 antagonistic antibody. Aspects of the invention include the use of an IL-17 antagonistic antibody for the preparation of a medicament for regulating the genes in tables 3.1, 3.2, and/or 3.3 in 15 days or less and concomitantly reducing the PASI score in a patient having psoriasis by at least 10, 15, 20, 25, 30, 35, 40, 45, 50, 55, 60, 65, 70, 75, 80, 85, 90, 95, or 100% in psoriasis patients. Further aspects described in Example 3 are also envisioned in methods of use, such as the temporal relationship between administration of an IL-17 antagonistic antibody and gene regulation as well as the extent (e.g., fold change) of gene regulation and administration of an IL-17 antagonistic antibody.

Embodiments of the invention include those described above and throughout the specification, including:

1. A method of treating psoriasis in adult and/or juvenile patients having psoriasis, comprising administering to said patient a pharmaceutical composition comprising an isolated antibody in a single or divided dose of about 70 to about 300 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

2. The method of embodiment 1, wherein the psoriasis is plaque psoriasis.

3. The method of embodiment 2, wherein the plaque psoriasis is moderate to severe plaque psoriasis.

4. The method of embodiment 3, wherein the moderate to severe plaque psoriasis is chronic moderate to severe plaque psoriasis and said patients are candidates for systemic therapy or phototherapy.

5. The method of embodiment 3, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

6. A method of treating psoriasis in adult and/or juvenile patients having psoriasis, comprising administering to said patient a pharmaceutical composition comprising an isolated antibody in a single or divided dose of about 70 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

7. The method of embodiment 6, wherein the psoriasis is plaque psoriasis.

8. The method of embodiment 6, wherein the plaque psoriasis is moderate to severe plaque psoriasis.

9. The method of embodiment 8, wherein the moderate to severe plaque psoriasis is chronic moderate to severe plaque psoriasis and said patients are candidates for systemic therapy or phototherapy.

10. The method of embodiment 8, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

11. A method of treating psoriasis in adult and/or juvenile patients having psoriasis, comprising administering to said patient a pharmaceutical composition comprising an isolated antibody in a single or divided dose of about 140 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

12. The method of embodiment 11, wherein the psoriasis is plaque psoriasis.

13. The method of embodiment 12, wherein the plaque psoriasis is moderate to severe plaque psoriasis.

14. The method of embodiment 13, wherein the moderate to severe plaque psoriasis is chronic moderate to severe plaque psoriasis and said patients are candidates for systemic therapy or phototherapy.

15. The method of embodiment 13, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

16. A method of treating psoriasis in adult and/or juvenile patients having psoriasis, comprising administering to said patient a pharmaceutical composition comprising an isolated antibody in a single or divided dose of about 210 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

17. The method of embodiment 16, wherein the psoriasis is plaque psoriasis.

18. The method of embodiment 17, wherein the plaque psoriasis is moderate to severe plaque psoriasis.

19. The method of embodiment 18, wherein the moderate to severe plaque psoriasis is chronic moderate to severe plaque psoriasis and said patients are candidates for systemic therapy or phototherapy.

20. The method of embodiment 18, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

21. A method of treating psoriasis in adult and/or juvenile patients having psoriasis, comprising administering to said patient a pharmaceutical composition comprising an isolated antibody in a single or divided dose of about 280 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

22. The method of embodiment 21, wherein the psoriasis is plaque psoriasis.

23. The method of embodiment 22, wherein the plaque psoriasis is moderate to severe plaque psoriasis.

24. The method of embodiment 23, wherein the moderate to severe plaque psoriasis is chronic moderate to severe plaque psoriasis and said patients are candidates for systemic therapy or phototherapy.

25. The method of embodiment 23, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

26. A method of treating psoriasis in adult and/or juvenile patients having psoriasis, comprising administering to said patient a pharmaceutical composition comprising an isolated antibody in a single or divided dose of about 70 to about 300 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

27. The method of embodiment 26, wherein the psoriasis is plaque psoriasis.

28. The method of embodiment 27, wherein the plaque psoriasis is moderate to severe plaque psoriasis.

29. The method of embodiment 28, wherein the moderate to severe plaque psoriasis is chronic moderate to severe plaque psoriasis and said patients are candidates for systemic therapy or phototherapy.

30. The method of embodiment 28, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

31. A method of treating psoriasis in adult and/or juvenile patients having psoriasis, comprising administering to said patient a pharmaceutical composition comprising an isolated antibody in a single or divided dose of about 70 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

32. The method of embodiment 31, wherein the psoriasis is plaque psoriasis.

33. The method of embodiment 32, wherein the plaque psoriasis is moderate to severe plaque psoriasis.

34. The method of embodiment 33, wherein the moderate to severe plaque psoriasis is chronic moderate to severe plaque psoriasis and said patients are candidates for systemic therapy or phototherapy.

35. The method of embodiment 33, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

36. A method of treating psoriasis in adult and/or juvenile patients having psoriasis, comprising administering to said patient a pharmaceutical composition comprising an isolated antibody in a single or divided dose of about 140 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

37. The method of embodiment 36, wherein the psoriasis is plaque psoriasis.

38. The method of embodiment 36, wherein the plaque psoriasis is moderate to severe plaque psoriasis.

39. The method of embodiment 38, wherein the moderate to severe plaque psoriasis is chronic moderate to severe plaque psoriasis and said patients are candidates for systemic therapy or phototherapy.

40. The method of embodiment 38, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

41. A method of treating psoriasis in adult and/or juvenile patients having psoriasis, comprising administering to said patient a pharmaceutical composition comprising an isolated antibody in a single or divided dose of about 210 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

42. The method of embodiment 41, wherein the psoriasis is plaque psoriasis.

43. The method of embodiment 42, wherein the plaque psoriasis is moderate to severe plaque psoriasis.

44. The method of embodiment 43, wherein the moderate to severe plaque psoriasis is chronic moderate to severe plaque psoriasis and said patients are candidates for systemic therapy or phototherapy.

45. The method of embodiment 43, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

46. A method of treating psoriasis in adult and/or juvenile patients having psoriasis, comprising administering to said patient a pharmaceutical composition comprising an isolated antibody in a single or divided dose of about 280 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

47. The method of embodiment 46, wherein the psoriasis is plaque psoriasis.

48. The method of embodiment 47, wherein the plaque psoriasis is moderate to severe plaque psoriasis.

49. The method of embodiment 48, wherein the moderate to severe plaque psoriasis is chronic moderate to severe plaque psoriasis and said patients are candidates for systemic therapy or phototherapy.

50. The method of embodiment 48, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

51. A method of treating psoriasis in adult and/or juvenile patients having psoriasis, comprising administering to said patient a pharmaceutical composition comprising an isolated antibody in a single or divided dose of about 70 to about 300 mg antibody per dose, wherein said antibody, or IL-17RA-binding fragment thereof, comprises a heavy chain sequence comprising SEQ ID NO:1 and a light chain sequence comprising SEQ ID NO:2.

52. The method of embodiment 51, wherein the psoriasis is plaque psoriasis.

53. The method of embodiment 52, wherein the plaque psoriasis is moderate to severe plaque psoriasis.

54. The method of embodiment 53, wherein the moderate to severe plaque psoriasis is chronic moderate to severe plaque psoriasis and said patients are candidates for systemic therapy or phototherapy.

55. The method of embodiment 53, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

56. A method of treating psoriasis in adult and/or juvenile patients having psoriasis, comprising administering to said patient a pharmaceutical composition comprising an isolated antibody in a single or divided dose of about 70 mg antibody per dose, wherein said antibody, or IL-17RA-binding fragment thereof, comprises a heavy chain sequence comprising SEQ ID NO:1 and a light chain sequence comprising SEQ ID NO:2.

57. The method of embodiment 56, wherein the psoriasis is plaque psoriasis.

58. The method of embodiment 57, wherein the plaque psoriasis is moderate to severe plaque psoriasis.

59. The method of embodiment 58, wherein the moderate to severe plaque psoriasis is chronic moderate to severe plaque psoriasis and said patients are candidates for systemic therapy or phototherapy.

60. The method of embodiment 58, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

61. A method of treating psoriasis in adult and/or juvenile patients having psoriasis, comprising administering to said patient a pharmaceutical composition comprising an isolated antibody in a single or divided dose of about 140 mg antibody per dose, wherein said antibody, or IL-17RA-binding fragment thereof, comprises a heavy chain sequence comprising SEQ ID NO:1 and a light chain sequence comprising SEQ ID NO:2.

62. The method of embodiment 61, wherein the psoriasis is plaque psoriasis.

63. The method of embodiment 62, wherein the plaque psoriasis is moderate to severe plaque psoriasis.

64. The method of embodiment 63, wherein the moderate to severe plaque psoriasis is chronic moderate to severe plaque psoriasis and said patients are candidates for systemic therapy or phototherapy.

65. The method of embodiment 63, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

66. A method of treating psoriasis in adult and/or juvenile patients having psoriasis, comprising administering to said patient a pharmaceutical composition comprising an isolated antibody in a single or divided dose of about 210 mg antibody per dose, wherein said antibody, or IL-17RA-binding fragment thereof, comprises a heavy chain sequence comprising SEQ ID NO:1 and a light chain sequence comprising SEQ ID NO:2.

67. The method of embodiment 66, wherein the psoriasis is plaque psoriasis.

68. The method of embodiment 67, wherein the plaque psoriasis is moderate to severe plaque psoriasis.

69. The method of embodiment 68, wherein the moderate to severe plaque psoriasis is chronic moderate to severe plaque psoriasis and said patients are candidates for systemic therapy or phototherapy.

70. The method of embodiment 68, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

71. A method of treating psoriasis in adult and/or juvenile patients having psoriasis, comprising administering to said patient a pharmaceutical composition comprising an isolated antibody in a single or divided dose of about 280 mg antibody per dose, wherein said antibody, or IL-17RA-binding fragment thereof, comprises a heavy chain sequence comprising SEQ ID NO:1 and a light chain sequence comprising SEQ ID NO:2.

72. The method of embodiment 71, wherein the psoriasis is plaque psoriasis.

73. The method of embodiment 72, wherein the plaque psoriasis is moderate to severe plaque psoriasis.

74. The method of embodiment 73, wherein the moderate to severe plaque psoriasis is chronic moderate to severe plaque psoriasis and said patients are candidates for systemic therapy or phototherapy.

75. The method of embodiment 73, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

76. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 to about 300 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

77. The method of embodiment 76, wherein the psoriasis is plaque psoriasis.

78. The method of embodiment 77, wherein the plaque psoriasis is moderate to severe plaque psoriasis.

79. The method of embodiment 78, wherein the moderate to severe plaque psoriasis is chronic moderate to severe plaque psoriasis and said patients are candidates for systemic therapy or phototherapy.

80. The method of embodiment 78, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

81. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

82. The method of embodiment 81, wherein the psoriasis is plaque psoriasis.

83. The method of embodiment 82, wherein the plaque psoriasis is moderate to severe plaque psoriasis.

84. The method of embodiment 83, wherein the moderate to severe plaque psoriasis is chronic moderate to severe plaque psoriasis and said patients are candidates for systemic therapy or phototherapy.

85. The method of embodiment 83, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

86. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 140 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

87. The method of embodiment 86, wherein the psoriasis is plaque psoriasis.

88. The method of embodiment 87, wherein the plaque psoriasis is moderate to severe plaque psoriasis.

89. The method of embodiment 88, wherein the moderate to severe plaque psoriasis is chronic moderate to severe plaque psoriasis and said patients are candidates for systemic therapy or phototherapy.

90. The method of embodiment 88, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

91. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 210 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

92. The method of embodiment 91, wherein the psoriasis is plaque psoriasis.

93. The method of embodiment 92, wherein the plaque psoriasis is moderate to severe plaque psoriasis.

94. The method of embodiment 93, wherein the moderate to severe plaque psoriasis is chronic moderate to severe plaque psoriasis and said patients are candidates for systemic therapy or phototherapy.

95. The method of embodiment 93, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

96. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 280 mg antibody per dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

97. The method of embodiment 96, wherein the psoriasis is plaque psoriasis.

98. The method of embodiment 97, wherein the plaque psoriasis is moderate to severe plaque psoriasis.

99. The method of embodiment 98, wherein the moderate to severe plaque psoriasis is chronic moderate to severe plaque psoriasis and said patients are candidates for systemic therapy or phototherapy.

100. The method of embodiment 99, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

101. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 to about 300 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

102. The method of embodiment 101, wherein the psoriasis is plaque psoriasis.

103. The method of embodiment 102, wherein the plaque psoriasis is moderate to severe plaque psoriasis.

104. The method of embodiment 103, wherein the moderate to severe plaque psoriasis is chronic moderate to severe plaque psoriasis and said patients are candidates for systemic therapy or phototherapy.

105. The method of embodiment 103, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

106. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

107. The method of embodiment 106, wherein the psoriasis is plaque psoriasis.

108. The method of embodiment 107, wherein the plaque psoriasis is moderate to severe plaque psoriasis.

109. The method of embodiment 108, wherein the moderate to severe plaque psoriasis is chronic moderate to severe plaque psoriasis and said patients are candidates for systemic therapy or phototherapy.

110. The method of embodiment 108, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

111. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 140 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

112. The method of embodiment 111, wherein the psoriasis is plaque psoriasis.

113. The method of embodiment 112, wherein the plaque psoriasis is moderate to severe plaque psoriasis.

114. The method of embodiment 113, wherein the moderate to severe plaque psoriasis is chronic moderate to severe plaque psoriasis and said patients are candidates for systemic therapy or phototherapy.

115. The method of embodiment 113, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

116. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 210 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

117. The method of embodiment 116, wherein the psoriasis is plaque psoriasis.

118. The method of embodiment 117, wherein the plaque psoriasis is moderate to severe plaque psoriasis.

119. The method of embodiment 118, wherein the moderate to severe plaque psoriasis is chronic moderate to severe plaque psoriasis and said patients are candidates for systemic therapy or phototherapy.

120. The method of embodiment 118, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

121. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 280 mg antibody per dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

122. The method of embodiment 121, wherein the psoriasis is plaque psoriasis.

123. The method of embodiment 122, wherein the plaque psoriasis is moderate to severe plaque psoriasis.

124. The method of embodiment 123, wherein the moderate to severe plaque psoriasis is chronic moderate to severe plaque psoriasis and said patients are candidates for systemic therapy or phototherapy.

125. The method of embodiment 123, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

126. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 to about 300 mg antibody per dose, wherein said antibody, or IL-17RA-binding fragment thereof, comprises a heavy chain sequence comprising SEQ ID NO:1 and a light chain sequence comprising SEQ ID NO:2.

127. The method of embodiment 126, wherein the psoriasis is plaque psoriasis.

128. The method of embodiment 127, wherein the plaque psoriasis is moderate to severe plaque psoriasis.

129. The method of embodiment 128, wherein the moderate to severe plaque psoriasis is chronic moderate to severe plaque psoriasis and said patients are candidates for systemic therapy or phototherapy.

130. The method of embodiment 128, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

131. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 70 mg antibody per dose, wherein said antibody, or IL-17RA-binding fragment thereof, comprises a heavy chain sequence comprising SEQ ID NO:1 and a light chain sequence comprising SEQ ID NO:2.

132. The method of embodiment 131, wherein the psoriasis is plaque psoriasis.

133. The method of embodiment 132, wherein the plaque psoriasis is moderate to severe plaque psoriasis.

134. The method of embodiment 133, wherein the moderate to severe plaque psoriasis is chronic moderate to severe plaque psoriasis and said patients are candidates for systemic therapy or phototherapy.

135. The method of embodiment 133, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

136. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 140 mg antibody per dose, wherein said antibody, or IL-17RA-binding fragment thereof, comprises a heavy chain sequence comprising SEQ ID NO:1 and a light chain sequence comprising SEQ ID NO:2.

137. The method of embodiment 136, wherein the psoriasis is plaque psoriasis.

138. The method of embodiment 137, wherein the plaque psoriasis is moderate to severe plaque psoriasis.

139. The method of embodiment 138, wherein the moderate to severe plaque psoriasis is chronic moderate to severe plaque psoriasis and said patients are candidates for systemic therapy or phototherapy.

140. The method of embodiment 138, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

141. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 210 mg antibody per dose, wherein said antibody, or IL-17RA-binding fragment thereof, comprises a heavy chain sequence comprising SEQ ID NO:1 and a light chain sequence comprising SEQ ID NO:2.

142. The method of embodiment 141, wherein the psoriasis is plaque psoriasis.

143. The method of embodiment 142, wherein the plaque psoriasis is moderate to severe plaque psoriasis.

144. The method of embodiment 143, wherein the moderate to severe plaque psoriasis is chronic moderate to severe plaque psoriasis and said patients are candidates for systemic therapy or phototherapy.

145. The method of embodiment 143, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

146. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an isolated antibody in a single or divided dose of about 280 mg antibody per dose, wherein said antibody, or IL-17RA-binding fragment thereof, comprises a heavy chain sequence comprising SEQ ID NO:1 and a light chain sequence comprising SEQ ID NO:2.

147. The method of embodiment 146, wherein the psoriasis is plaque psoriasis.

148. The method of embodiment 147, wherein the plaque psoriasis is moderate to severe plaque psoriasis.

149. The method of embodiment 148, wherein the moderate to severe plaque psoriasis is chronic moderate to severe plaque psoriasis and said patients are candidates for systemic therapy or phototherapy.

150. The method of embodiment 148, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

151. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

152. The method of embodiment 151, wherein the psoriasis is plaque psoriasis.

153. The method of embodiment 152, wherein the plaque psoriasis is moderate to severe plaque psoriasis.

154. The method of embodiment 153, wherein the moderate to severe plaque psoriasis is chronic moderate to severe plaque psoriasis and said patients are candidates for systemic therapy or phototherapy.

155. The method of embodiment 153, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

156. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

157. The method of embodiment 156, wherein the psoriasis is plaque psoriasis.

158. The method of embodiment 157, wherein the plaque psoriasis is moderate to severe plaque psoriasis.

159. The method of embodiment 158, wherein the moderate to severe plaque psoriasis is chronic moderate to severe plaque psoriasis and said patients are candidates for systemic therapy or phototherapy.

160. The method of embodiment 158, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

161. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

162. The method of embodiment 161, wherein the psoriasis is plaque psoriasis.

163. The method of embodiment 162, wherein the plaque psoriasis is moderate to severe plaque psoriasis.

164. The method of embodiment 163, wherein the moderate to severe plaque psoriasis is chronic moderate to severe plaque psoriasis and said patients are candidates for systemic therapy or phototherapy.

165. The method of embodiment 163, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

166. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

167. The method of embodiment 166, wherein the psoriasis is plaque psoriasis.

168. The method of embodiment 167, wherein the plaque psoriasis is moderate to severe plaque psoriasis.

169. The method of embodiment 168, wherein the moderate to severe plaque psoriasis is chronic moderate to severe plaque psoriasis and said patients are candidates for systemic therapy or phototherapy.

170. The method of embodiment 168, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

171. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

172. The method of embodiment 171, wherein the psoriasis is plaque psoriasis.

173. The method of embodiment 172, wherein the plaque psoriasis is moderate to severe plaque psoriasis.

174. The method of embodiment 173, wherein the moderate to severe plaque psoriasis is chronic moderate to severe plaque psoriasis and said patients are candidates for systemic therapy or phototherapy.

175. The method of embodiment 173, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

176. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

177. The method of embodiment 176, wherein the psoriasis is plaque psoriasis.

178. The method of embodiment 177, wherein the plaque psoriasis is moderate to severe plaque psoriasis.

179. The method of embodiment 178, wherein the moderate to severe plaque psoriasis is chronic moderate to severe plaque psoriasis and said patients are candidates for systemic therapy or phototherapy.

180. The method of embodiment 178, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

181. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

182. The method of embodiment 181, wherein the psoriasis is plaque psoriasis.

183. The method of embodiment 182, wherein the plaque psoriasis is moderate to severe plaque psoriasis.

184. The method of embodiment 183, wherein the moderate to severe plaque psoriasis is chronic moderate to severe plaque psoriasis and said patients are candidates for systemic therapy or phototherapy.

185. The method of embodiment 183, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

186. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

187. The method of embodiment 186, wherein the psoriasis is plaque psoriasis.

188. The method of embodiment 187, wherein the plaque psoriasis is moderate to severe plaque psoriasis.

189. The method of embodiment 188, wherein the moderate to severe plaque psoriasis is chronic moderate to severe plaque psoriasis and said patients are candidates for systemic therapy or phototherapy.

190. The method of embodiment 188, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

191. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

192. The method of embodiment 191, wherein the psoriasis is plaque psoriasis.

193. The method of embodiment 192, wherein the plaque psoriasis is moderate to severe plaque psoriasis.

194. The method of embodiment 193, wherein the moderate to severe plaque psoriasis is chronic moderate to severe plaque psoriasis and said patients are candidates for systemic therapy or phototherapy.

195. The method of embodiment 193, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

196. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

197. The method of embodiment 196, wherein the psoriasis is plaque psoriasis.

198. The method of embodiment 197, wherein the plaque psoriasis is moderate to severe plaque psoriasis.

199. The method of embodiment 198, wherein the moderate to severe plaque psoriasis is chronic moderate to severe plaque psoriasis and said patients are candidates for systemic therapy or phototherapy.

200. The method of embodiment 198, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

201. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

202. The method of embodiment 201, wherein the psoriasis is plaque psoriasis.

203. The method of embodiment 202, wherein the plaque psoriasis is moderate to severe plaque psoriasis.

204. The method of embodiment 203, wherein the moderate to severe plaque psoriasis is chronic moderate to severe plaque psoriasis and said patients are candidates for systemic therapy or phototherapy.

205. The method of embodiment 203, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

206. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

207. The method of embodiment 206, wherein the psoriasis is plaque psoriasis.

208. The method of embodiment 207, wherein the plaque psoriasis is moderate to severe plaque psoriasis.

209. The method of embodiment 208, wherein the moderate to severe plaque psoriasis is chronic moderate to severe plaque psoriasis and said patients are candidates for systemic therapy or phototherapy.

210. The method of embodiment 208, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

211. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

212. The method of embodiment 211, wherein the psoriasis is plaque psoriasis.

213. The method of embodiment 212, wherein the plaque psoriasis is moderate to severe plaque psoriasis.

214. The method of embodiment 213, wherein the moderate to severe plaque psoriasis is chronic moderate to severe plaque psoriasis and said patients are candidates for systemic therapy or phototherapy.

215. The method of embodiment 213, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

216. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

217. The method of embodiment 216, wherein the psoriasis is plaque psoriasis.

218. The method of embodiment 217, wherein the plaque psoriasis is moderate to severe plaque psoriasis.

219. The method of embodiment 218, wherein the moderate to severe plaque psoriasis is chronic moderate to severe plaque psoriasis and said patients are candidates for systemic therapy or phototherapy.

220. The method of embodiment 218, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

221. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

222. The method of embodiment 221, wherein the psoriasis is plaque psoriasis.

223. The method of embodiment 222, wherein the plaque psoriasis is moderate to severe plaque psoriasis.

224. The method of embodiment 223, wherein the moderate to severe plaque psoriasis is chronic moderate to severe plaque psoriasis and said patients are candidates for systemic therapy or phototherapy.

225. The method of embodiment 223, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

226. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

227. The method of embodiment 226, wherein the psoriasis is plaque psoriasis.

228. The method of embodiment 227, wherein the plaque psoriasis is moderate to severe plaque psoriasis.

229. The method of embodiment 228, wherein the moderate to severe plaque psoriasis is chronic moderate to severe plaque psoriasis and said patients are candidates for systemic therapy or phototherapy.

230. The method of embodiment 228, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

231. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

232. The method of embodiment 231, wherein the psoriasis is plaque psoriasis.

233. The method of embodiment 232, wherein the plaque psoriasis is moderate to severe plaque psoriasis.

234. The method of embodiment 233, wherein the moderate to severe plaque psoriasis is chronic moderate to severe plaque psoriasis and said patients are candidates for systemic therapy or phototherapy.

235. The method of embodiment 233, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

236. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

237. The method of embodiment 236, wherein the psoriasis is plaque psoriasis.

238. The method of embodiment 237, wherein the plaque psoriasis is moderate to severe plaque psoriasis.

239. The method of embodiment 238, wherein the moderate to severe plaque psoriasis is chronic moderate to severe plaque psoriasis and said patients are candidates for systemic therapy or phototherapy.

240. The method of embodiment 238, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

241. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

242. The method of embodiment 241, wherein the psoriasis is plaque psoriasis.

243. The method of embodiment 242, wherein the plaque psoriasis is moderate to severe plaque psoriasis.

244. The method of embodiment 243, wherein the moderate to severe plaque psoriasis is chronic moderate to severe plaque psoriasis and said patients are candidates for systemic therapy or phototherapy.

245. The method of embodiment 243, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

246. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

247. The method of embodiment 246, wherein the psoriasis is plaque psoriasis.

248. The method of embodiment 247, wherein the plaque psoriasis is moderate to severe plaque psoriasis.

249. The method of embodiment 248, wherein the moderate to severe plaque psoriasis is chronic moderate to severe plaque psoriasis and said patients are candidates for systemic therapy or phototherapy.

250. The method of embodiment 248, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

251. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

252. The method of embodiment 251, wherein the psoriasis is plaque psoriasis.

253. The method of embodiment 252, wherein the plaque psoriasis is moderate to severe plaque psoriasis.

254. The method of embodiment 253, wherein the moderate to severe plaque psoriasis is chronic moderate to severe plaque psoriasis and said patients are candidates for systemic therapy or phototherapy.

255. The method of embodiment 253, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

256. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

257. The method of embodiment 256, wherein the psoriasis is plaque psoriasis.

258. The method of embodiment 257, wherein the plaque psoriasis is moderate to severe plaque psoriasis.

259. The method of embodiment 258, wherein the moderate to severe plaque psoriasis is chronic moderate to severe plaque psoriasis and said patients are candidates for systemic therapy or phototherapy.

260. The method of embodiment 258, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

261. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

262. The method of embodiment 261, wherein the psoriasis is plaque psoriasis.

263. The method of embodiment 262, wherein the plaque psoriasis is moderate to severe plaque psoriasis.

264. The method of embodiment 263, wherein the moderate to severe plaque psoriasis is chronic moderate to severe plaque psoriasis and said patients are candidates for systemic therapy or phototherapy.

265. The method of embodiment 263, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

266. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

267. The method of embodiment 266, wherein the psoriasis is plaque psoriasis.

268. The method of embodiment 267, wherein the plaque psoriasis is moderate to severe plaque psoriasis.

269. The method of embodiment 268, wherein the moderate to severe plaque psoriasis is chronic moderate to severe plaque psoriasis and said patients are candidates for systemic therapy or phototherapy.

270. The method of embodiment 268, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

271. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

272. The method of embodiment 271, wherein the psoriasis is plaque psoriasis.

273. The method of embodiment 272, wherein the plaque psoriasis is moderate to severe plaque psoriasis.

274. The method of embodiment 273, wherein the moderate to severe plaque psoriasis is chronic moderate to severe plaque psoriasis and said patients are candidates for systemic therapy or phototherapy.

275. The method of embodiment 273, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

276. A method of treating psoriasis in adult and/or juvenile patients having psoriasis, comprising administering to said patient a pharmaceutical composition comprising an isolated antibody in a single or divided dose of about 70 to about 300 mg antibody per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

277. The method of embodiment 276, wherein the psoriasis is plaque psoriasis.

278. The method of embodiment 277, wherein the plaque psoriasis is moderate to severe plaque psoriasis.

279. The method of embodiment 278, wherein the moderate to severe plaque psoriasis is chronic moderate to severe plaque psoriasis and said patients are candidates for systemic therapy or phototherapy.

280. The method of embodiment 278, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

281. A method of treating psoriasis in adult and/or juvenile patients having psoriasis, comprising administering to said patient a pharmaceutical composition comprising an isolated antibody in a single or divided dose of 70 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

282. The method of embodiment 281, wherein the psoriasis is plaque psoriasis.

283. The method of embodiment 282, wherein the plaque psoriasis is moderate to severe plaque psoriasis.

284. The method of embodiment 283, wherein the moderate to severe plaque psoriasis is chronic moderate to severe plaque psoriasis and said patients are candidates for systemic therapy or phototherapy.

285. The method of embodiment 283, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

286. A method of treating psoriasis in adult and/or juvenile patients having psoriasis, comprising administering to said patient a pharmaceutical composition comprising an isolated antibody in a single or divided dose of 140 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

287. The method of embodiment 286, wherein the psoriasis is plaque psoriasis.

288. The method of embodiment 287, wherein the plaque psoriasis is moderate to severe plaque psoriasis.

289. The method of embodiment 288, wherein the moderate to severe plaque psoriasis is chronic moderate to severe plaque psoriasis and said patients are candidates for systemic therapy or phototherapy.

290. The method of embodiment 288, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

291. A method of treating psoriasis in adult and/or juvenile patients having psoriasis, comprising administering to said patient a pharmaceutical composition comprising an isolated antibody in a single or divided dose of 210 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

292. The method of embodiment 291, wherein the psoriasis is plaque psoriasis.

293. The method of embodiment 292, wherein the plaque psoriasis is moderate to severe plaque psoriasis.

294. The method of embodiment 293, wherein the moderate to severe plaque psoriasis is chronic moderate to severe plaque psoriasis and said patients are candidates for systemic therapy or phototherapy.

295. The method of embodiment 293, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

296. A method of treating psoriasis in adult and/or juvenile patients having psoriasis, comprising administering to said patient a pharmaceutical composition comprising an isolated antibody in a single or divided dose of 280 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

297. The method of embodiment 296, wherein the psoriasis is plaque psoriasis.

298. The method of embodiment 297, wherein the plaque psoriasis is moderate to severe plaque psoriasis.

299. The method of embodiment 298, wherein the moderate to severe plaque psoriasis is chronic moderate to severe plaque psoriasis and said patients are candidates for systemic therapy or phototherapy.

300. The method of embodiment 298, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

301. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 210 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

302. The method of embodiment 301, wherein the psoriasis is plaque psoriasis.

303. The method of embodiment 302, wherein the plaque psoriasis is moderate to severe plaque psoriasis.

304. The method of embodiment 303, wherein the moderate to severe plaque psoriasis is chronic moderate to severe plaque psoriasis and said patients are candidates for systemic therapy or phototherapy.

305. The method of embodiment 303, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

306. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 210 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

307. The method of embodiment 306, wherein the psoriasis is plaque psoriasis.

308. The method of embodiment 307, wherein the plaque psoriasis is moderate to severe plaque psoriasis.

309. The method of embodiment 308, wherein the moderate to severe plaque psoriasis is chronic moderate to severe plaque psoriasis and said patients are candidates for systemic therapy or phototherapy.

310. The method of embodiment 308, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

311. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 210 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

312. The method of embodiment 311, wherein the psoriasis is plaque psoriasis.

313. The method of embodiment 312, wherein the plaque psoriasis is moderate to severe plaque psoriasis.

314. The method of embodiment 313, wherein the moderate to severe plaque psoriasis is chronic moderate to severe plaque psoriasis and said patients are candidates for systemic therapy or phototherapy.

315. The method of embodiment 313, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

316. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 280 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

317. The method of embodiment 316, wherein the psoriasis is plaque psoriasis.

318. The method of embodiment 317, wherein the plaque psoriasis is moderate to severe plaque psoriasis.

319. The method of embodiment 318, wherein the moderate to severe plaque psoriasis is chronic moderate to severe plaque psoriasis and said patients are candidates for systemic therapy or phototherapy.

320. The method of embodiment 318, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

321. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 280 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

322. The method of embodiment 321, wherein the psoriasis is plaque psoriasis.

323. The method of embodiment 322, wherein the plaque psoriasis is moderate to severe plaque psoriasis.

324. The method of embodiment 323, wherein the moderate to severe plaque psoriasis is chronic moderate to severe plaque psoriasis and said patients are candidates for systemic therapy or phototherapy.

325. The method of embodiment 323, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

326. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 280 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

327. The method of embodiment 326, wherein the psoriasis is plaque psoriasis.

328. The method of embodiment 327, wherein the plaque psoriasis is moderate to severe plaque psoriasis.

329. The method of embodiment 328, wherein the moderate to severe plaque psoriasis is chronic moderate to severe plaque psoriasis and said patients are candidates for systemic therapy or phototherapy.

330. The method of embodiment 328, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

331. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 210 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

332. The method of embodiment 331, wherein the psoriasis is plaque psoriasis.

333. The method of embodiment 332, wherein the plaque psoriasis is moderate to severe plaque psoriasis.

334. The method of embodiment 333, wherein the moderate to severe plaque psoriasis is chronic moderate to severe plaque psoriasis and said patients are candidates for systemic therapy or phototherapy.

335. The method of embodiment 333, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

336. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 210 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

337. The method of embodiment 336, wherein the psoriasis is plaque psoriasis.

338. The method of embodiment 337, wherein the plaque psoriasis is moderate to severe plaque psoriasis.

339. The method of embodiment 338, wherein the moderate to severe plaque psoriasis is chronic moderate to severe plaque psoriasis and said patients are candidates for systemic therapy or phototherapy.

340. The method of embodiment 338, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

341. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 210 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

342. The method of embodiment 341, wherein the psoriasis is plaque psoriasis.

343. The method of embodiment 342, wherein the plaque psoriasis is moderate to severe plaque psoriasis.

344. The method of embodiment 343, wherein the moderate to severe plaque psoriasis is chronic moderate to severe plaque psoriasis and said patients are candidates for systemic therapy or phototherapy.

345. The method of embodiment 343, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

346. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 280 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

347. The method of embodiment 346, wherein the psoriasis is plaque psoriasis.

348. The method of embodiment 347, wherein the plaque psoriasis is moderate to severe plaque psoriasis.

349. The method of embodiment 348, wherein the moderate to severe plaque psoriasis is chronic moderate to severe plaque psoriasis and said patients are candidates for systemic therapy or phototherapy.

350. The method of embodiment 348, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

351. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 280 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

352. The method of embodiment 351, wherein the psoriasis is plaque psoriasis.

353. The method of embodiment 352, wherein the plaque psoriasis is moderate to severe plaque psoriasis.

354. The method of embodiment 353, wherein the moderate to severe plaque psoriasis is chronic moderate to severe plaque psoriasis and said patients are candidates for systemic therapy or phototherapy.

355. The method of embodiment 323, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

356. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 280 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

357. The method of embodiment 356, wherein the psoriasis is plaque psoriasis.

358. The method of embodiment 357, wherein the plaque psoriasis is moderate to severe plaque psoriasis.

359. The method of embodiment 358, wherein the moderate to severe plaque psoriasis is chronic moderate to severe plaque psoriasis and said patients are candidates for systemic therapy or phototherapy.

360. The method of embodiment 358, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

361. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

362. The method of embodiment 361, wherein the psoriasis is plaque psoriasis.

363. The method of embodiment 362, wherein the plaque psoriasis is moderate to severe plaque psoriasis.

364. The method of embodiment 363, wherein the moderate to severe plaque psoriasis is chronic moderate to severe plaque psoriasis and said patients are candidates for systemic therapy or phototherapy.

365. The method of embodiment 363, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

366. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

367. The method of embodiment 366, wherein the psoriasis is plaque psoriasis.

368. The method of embodiment 367, wherein the plaque psoriasis is moderate to severe plaque psoriasis.

369. The method of embodiment 368, wherein the moderate to severe plaque psoriasis is chronic moderate to severe plaque psoriasis and said patients are candidates for systemic therapy or phototherapy.

370. The method of embodiment 368, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

371. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

372. The method of embodiment 371, wherein the psoriasis is plaque psoriasis.

373. The method of embodiment 372, wherein the plaque psoriasis is moderate to severe plaque psoriasis.

374. The method of embodiment 373, wherein the moderate to severe plaque psoriasis is chronic moderate to severe plaque psoriasis and said patients are candidates for systemic therapy or phototherapy.

375. The method of embodiment 373, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

376. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

377. The method of embodiment 376, wherein the psoriasis is plaque psoriasis.

378. The method of embodiment 377, wherein the plaque psoriasis is moderate to severe plaque psoriasis.

379. The method of embodiment 378, wherein the moderate to severe plaque psoriasis is chronic moderate to severe plaque psoriasis and said patients are candidates for systemic therapy or phototherapy.

380. The method of embodiment 378, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

381. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

382. The method of embodiment 381, wherein the psoriasis is plaque psoriasis.

383. The method of embodiment 382, wherein the plaque psoriasis is moderate to severe plaque psoriasis.

384. The method of embodiment 383, wherein the moderate to severe plaque psoriasis is chronic moderate to severe plaque psoriasis and said patients are candidates for systemic therapy or phototherapy.

385. The method of embodiment 383, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

386. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

387. The method of embodiment 386, wherein the psoriasis is plaque psoriasis.

388. The method of embodiment 387, wherein the plaque psoriasis is moderate to severe plaque psoriasis.

389. The method of embodiment 388, wherein the moderate to severe plaque psoriasis is chronic moderate to severe plaque psoriasis and said patients are candidates for systemic therapy or phototherapy.

390. The method of embodiment 388, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

391. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

392. The method of embodiment 391, wherein the psoriasis is plaque psoriasis.

393. The method of embodiment 392, wherein the plaque psoriasis is moderate to severe plaque psoriasis.

394. The method of embodiment 393, wherein the moderate to severe plaque psoriasis is chronic moderate to severe plaque psoriasis and said patients are candidates for systemic therapy or phototherapy.

395. The method of embodiment 393, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

396. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

397. The method of embodiment 396, wherein the psoriasis is plaque psoriasis.

398. The method of embodiment 397, wherein the plaque psoriasis is moderate to severe plaque psoriasis.

399. The method of embodiment 398, wherein the moderate to severe plaque psoriasis is chronic moderate to severe plaque psoriasis and said patients are candidates for systemic therapy or phototherapy.

400. The method of embodiment 398, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

401. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

402. The method of embodiment 401, wherein the psoriasis is plaque psoriasis.

403. The method of embodiment 402, wherein the plaque psoriasis is moderate to severe plaque psoriasis.

404. The method of embodiment 403, wherein the moderate to severe plaque psoriasis is chronic moderate to severe plaque psoriasis and said patients are candidates for systemic therapy or phototherapy.

405. The method of embodiment 403, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

406. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

407. The method of embodiment 406, wherein the psoriasis is plaque psoriasis.

408. The method of embodiment 407, wherein the plaque psoriasis is moderate to severe plaque psoriasis.

409. The method of embodiment 408, wherein the moderate to severe plaque psoriasis is chronic moderate to severe plaque psoriasis and said patients are candidates for systemic therapy or phototherapy.

410. The method of embodiment 408, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

411. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

412. The method of embodiment 411, wherein the psoriasis is plaque psoriasis.

413. The method of embodiment 412, wherein the plaque psoriasis is moderate to severe plaque psoriasis.

414. The method of embodiment 413, wherein the moderate to severe plaque psoriasis is chronic moderate to severe plaque psoriasis and said patients are candidates for systemic therapy or phototherapy.

415. The method of embodiment 413, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

416. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

417. The method of embodiment 416, wherein the psoriasis is plaque psoriasis.

418. The method of embodiment 417, wherein the plaque psoriasis is moderate to severe plaque psoriasis.

419. The method of embodiment 418, wherein the moderate to severe plaque psoriasis is chronic moderate to severe plaque psoriasis and said patients are candidates for systemic therapy or phototherapy.

420. The method of embodiment 418, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

421. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

422. The method of embodiment 421, wherein the psoriasis is plaque psoriasis.

423. The method of embodiment 422, wherein the plaque psoriasis is moderate to severe plaque psoriasis.

424. The method of embodiment 423, wherein the moderate to severe plaque psoriasis is chronic moderate to severe plaque psoriasis and said patients are candidates for systemic therapy or phototherapy.

425. The method of embodiment 423, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

426. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

427. The method of embodiment 426, wherein the psoriasis is plaque psoriasis.

428. The method of embodiment 427, wherein the plaque psoriasis is moderate to severe plaque psoriasis.

429. The method of embodiment 428, wherein the moderate to severe plaque psoriasis is chronic moderate to severe plaque psoriasis and said patients are candidates for systemic therapy or phototherapy.

430. The method of embodiment 428, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

431. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

432. The method of embodiment 431, wherein the psoriasis is plaque psoriasis.

433. The method of embodiment 432, wherein the plaque psoriasis is moderate to severe plaque psoriasis.

434. The method of embodiment 433, wherein the moderate to severe plaque psoriasis is chronic moderate to severe plaque psoriasis and said patients are candidates for systemic therapy or phototherapy.

435. The method of embodiment 433, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

436. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

437. The method of embodiment 436, wherein the psoriasis is plaque psoriasis.

438. The method of embodiment 437, wherein the plaque psoriasis is moderate to severe plaque psoriasis.

439. The method of embodiment 438, wherein the moderate to severe plaque psoriasis is chronic moderate to severe plaque psoriasis and said patients are candidates for systemic therapy or phototherapy.

440. The method of embodiment 438, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

441. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

442. The method of embodiment 441, wherein the psoriasis is plaque psoriasis.

443. The method of embodiment 442, wherein the plaque psoriasis is moderate to severe plaque psoriasis.

444. The method of embodiment 443, wherein the moderate to severe plaque psoriasis is chronic moderate to severe plaque psoriasis and said patients are candidates for systemic therapy or phototherapy.

445. The method of embodiment 443, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

446. A method of treating psoriasis in adult and/or juvenile patients having psoriasis, comprising administering to said patient a pharmaceutical composition comprising an isolated antibody in a single or divided dose of 140 mg every two weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

447. The method of embodiment 446, wherein the psoriasis is plaque psoriasis.

448. The method of embodiment 447, wherein the plaque psoriasis is moderate to severe plaque psoriasis.

449. The method of embodiment 448, wherein the moderate to severe plaque psoriasis is chronic moderate to severe plaque psoriasis and said patients are candidates for systemic therapy or phototherapy.

450. The method of embodiment 448, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

451. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

452. The method of embodiment 451, wherein the psoriasis is plaque psoriasis.

453. The method of embodiment 452, wherein the plaque psoriasis is moderate to severe plaque psoriasis.

454. The method of embodiment 453, wherein the moderate to severe plaque psoriasis is chronic moderate to severe plaque psoriasis and said patients are candidates for systemic therapy or phototherapy.

455. The method of embodiment 453, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

456. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

457. The method of embodiment 456, wherein the psoriasis is plaque psoriasis.

458. The method of embodiment 457, wherein the plaque psoriasis is moderate to severe plaque psoriasis.

459. The method of embodiment 458, wherein the moderate to severe plaque psoriasis is chronic moderate to severe plaque psoriasis and said patients are candidates for systemic therapy or phototherapy.

460. The method of embodiment 458, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

461. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

462. The method of embodiment 461, wherein the psoriasis is plaque psoriasis.

463. The method of embodiment 462, wherein the plaque psoriasis is moderate to severe plaque psoriasis.

464. The method of embodiment 463, wherein the moderate to severe plaque psoriasis is chronic moderate to severe plaque psoriasis and said patients are candidates for systemic therapy or phototherapy.

465. The method of embodiment 463, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

466. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

467. The method of embodiment 466, wherein the psoriasis is plaque psoriasis.

468. The method of embodiment 467, wherein the plaque psoriasis is moderate to severe plaque psoriasis.

469. The method of embodiment 468, wherein the moderate to severe plaque psoriasis is chronic moderate to severe plaque psoriasis and said patients are candidates for systemic therapy or phototherapy.

470. The method of embodiment 468, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

471. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

472. The method of embodiment 471, wherein the psoriasis is plaque psoriasis.

473. The method of embodiment 472, wherein the plaque psoriasis is moderate to severe plaque psoriasis.

474. The method of embodiment 473, wherein the moderate to severe plaque psoriasis is chronic moderate to severe plaque psoriasis and said patients are candidates for systemic therapy or phototherapy.

475. The method of embodiment 473, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

476. A method of treating psoriasis in adult and/or juvenile patients having psoriasis, comprising administering to said patient a pharmaceutical composition comprising an isolated antibody in a single or divided dose of 280 mg every four weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

477. The method of embodiment 476, wherein the psoriasis is plaque psoriasis.

478. The method of embodiment 477, wherein the plaque psoriasis is moderate to severe plaque psoriasis.

479. The method of embodiment 478, wherein the moderate to severe plaque psoriasis is chronic moderate to severe plaque psoriasis and said patients are candidates for systemic therapy or phototherapy.

480. The method of embodiment 478, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

481. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

482. The method of embodiment 481, wherein the psoriasis is plaque psoriasis.

483. The method of embodiment 482, wherein the plaque psoriasis is moderate to severe plaque psoriasis.

484. The method of embodiment 483, wherein the moderate to severe plaque psoriasis is chronic moderate to severe plaque psoriasis and said patients are candidates for systemic therapy or phototherapy.

485. The method of embodiment 483, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

486. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

487. The method of embodiment 486, wherein the psoriasis is plaque psoriasis.

488. The method of embodiment 487, wherein the plaque psoriasis is moderate to severe plaque psoriasis.

489. The method of embodiment 488, wherein the moderate to severe plaque psoriasis is chronic moderate to severe plaque psoriasis and said patients are candidates for systemic therapy or phototherapy.

490. The method of embodiment 488, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

491. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

492. The method of embodiment 491, wherein the psoriasis is plaque psoriasis.

493. The method of embodiment 492, wherein the plaque psoriasis is moderate to severe plaque psoriasis.

494. The method of embodiment 493, wherein the moderate to severe plaque psoriasis is chronic moderate to severe plaque psoriasis and said patients are candidates for systemic therapy or phototherapy.

495. The method of embodiment 493, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

496. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

497. The method of embodiment 496, wherein the psoriasis is plaque psoriasis.

498. The method of embodiment 497, wherein the plaque psoriasis is moderate to severe plaque psoriasis.

499. The method of embodiment 498, wherein the moderate to severe plaque psoriasis is chronic moderate to severe plaque psoriasis and said patients are candidates for systemic therapy or phototherapy.

500. The method of embodiment 498, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

501. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered every two weeks following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

502. The method of embodiment 501, wherein the psoriasis is plaque psoriasis.

503. The method of embodiment 502, wherein the plaque psoriasis is moderate to severe plaque psoriasis.

504. The method of embodiment 503, wherein the moderate to severe plaque psoriasis is chronic moderate to severe plaque psoriasis and said patients are candidates for systemic therapy or phototherapy.

505. The method of embodiment 503, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

506. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

507. The method of embodiment 506, wherein the psoriasis is plaque psoriasis.

508. The method of embodiment 507, wherein the plaque psoriasis is moderate to severe plaque psoriasis.

509. The method of embodiment 508, wherein the moderate to severe plaque psoriasis is chronic moderate to severe plaque psoriasis and said patients are candidates for systemic therapy or phototherapy.

510. The method of embodiment 508, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

511. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

512. The method of embodiment 511, wherein the psoriasis is plaque psoriasis.

513. The method of embodiment 512, wherein the plaque psoriasis is moderate to severe plaque psoriasis.

514. The method of embodiment 513, wherein the moderate to severe plaque psoriasis is chronic moderate to severe plaque psoriasis and said patients are candidates for systemic therapy or phototherapy.

515. The method of embodiment 513, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

516. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

517. The method of embodiment 516, wherein the psoriasis is plaque psoriasis.

518. The method of embodiment 517, wherein the plaque psoriasis is moderate to severe plaque psoriasis.

519. The method of embodiment 518, wherein the moderate to severe plaque psoriasis is chronic moderate to severe plaque psoriasis and said patients are candidates for systemic therapy or phototherapy.

520. The method of embodiment 518, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

521. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

522. The method of embodiment 521, wherein the psoriasis is plaque psoriasis.

523. The method of embodiment 522, wherein the plaque psoriasis is moderate to severe plaque psoriasis.

524. The method of embodiment 523, wherein the moderate to severe plaque psoriasis is chronic moderate to severe plaque psoriasis and said patients are candidates for systemic therapy or phototherapy.

525. The method of embodiment 523, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

526. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered every two weeks following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

527. The method of embodiment 526, wherein the psoriasis is plaque psoriasis.

528. The method of embodiment 527, wherein the plaque psoriasis is moderate to severe plaque psoriasis.

529. The method of embodiment 528, wherein the moderate to severe plaque psoriasis is chronic moderate to severe plaque psoriasis and said patients are candidates for systemic therapy or phototherapy.

530. The method of embodiment 528, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

531. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

532. The method of embodiment 531, wherein the psoriasis is plaque psoriasis.

533. The method of embodiment 532, wherein the plaque psoriasis is moderate to severe plaque psoriasis.

534. The method of embodiment 533, wherein the moderate to severe plaque psoriasis is chronic moderate to severe plaque psoriasis and said patients are candidates for systemic therapy or phototherapy.

535. The method of embodiment 533, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

536. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

537. The method of embodiment 536, wherein the psoriasis is plaque psoriasis.

538. The method of embodiment 537, wherein the plaque psoriasis is moderate to severe plaque psoriasis.

539. The method of embodiment 538, wherein the moderate to severe plaque psoriasis is chronic moderate to severe plaque psoriasis and said patients are candidates for systemic therapy or phototherapy.

540. The method of embodiment 538, wherein the moderate to severe plaque psoriasis is chronic moderate to severe plaque psoriasis and wherein said patients have failed to respond to, have a contraindication to, or are intolerant to 541. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

542. The method of embodiment 541, wherein the psoriasis is plaque psoriasis.

543. The method of embodiment 542, wherein the plaque psoriasis is moderate to severe plaque psoriasis.

544. The method of embodiment 543, wherein the moderate to severe plaque psoriasis is chronic moderate to severe plaque psoriasis and said patients are candidates for systemic therapy or phototherapy.

545. The method of embodiment 543, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

546. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

547. The method of embodiment 546, wherein the psoriasis is plaque psoriasis.

548. The method of embodiment 547, wherein the plaque psoriasis is moderate to severe plaque psoriasis.

549. The method of embodiment 548, wherein the moderate to severe plaque psoriasis is chronic moderate to severe plaque psoriasis and said patients are candidates for systemic therapy or phototherapy.

550. The method of embodiment 548, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

551. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered every two weeks following the week one administration, wherein said antibody, or IL-17RA-binding fragment thereof, comprises a heavy chain sequence comprising SEQ ID NO:1 and a light chain sequence comprising SEQ ID NO:2.

552. The method of embodiment 551, wherein the psoriasis is plaque psoriasis.

553. The method of embodiment 552, wherein the plaque psoriasis is moderate to severe plaque psoriasis.

554. The method of embodiment 553, wherein the moderate to severe plaque psoriasis is chronic moderate to severe plaque psoriasis and said patients are candidates for systemic therapy or phototherapy.

555. The method of embodiment 553, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

556. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

557. The method of embodiment 556, wherein the psoriasis is plaque psoriasis.

558. The method of embodiment 557, wherein the plaque psoriasis is moderate to severe plaque psoriasis.

559. The method of embodiment 558, wherein the moderate to severe plaque psoriasis is chronic moderate to severe plaque psoriasis and said patients are candidates for systemic therapy or phototherapy.

560. The method of embodiment 558, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

561. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

562. The method of embodiment 561, wherein the psoriasis is plaque psoriasis.

563. The method of embodiment 562, wherein the plaque psoriasis is moderate to severe plaque psoriasis.

564. The method of embodiment 563, wherein the moderate to severe plaque psoriasis is chronic moderate to severe plaque psoriasis and said patients are candidates for systemic therapy or phototherapy.

565. The method of embodiment 563, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

566. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

567. The method of embodiment 566, wherein the psoriasis is plaque psoriasis.

568. The method of embodiment 567, wherein the plaque psoriasis is moderate to severe plaque psoriasis.

569. The method of embodiment 568, wherein the moderate to severe plaque psoriasis is chronic moderate to severe plaque psoriasis and said patients are candidates for systemic therapy or phototherapy.

570. The method of embodiment 568, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

571. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

572. The method of embodiment 571, wherein the psoriasis is plaque psoriasis.

573. The method of embodiment 572, wherein the plaque psoriasis is moderate to severe plaque psoriasis.

574. The method of embodiment 573, wherein the moderate to severe plaque psoriasis is chronic moderate to severe plaque psoriasis and said patients are candidates for systemic therapy or phototherapy.

575. The method of embodiment 573, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

576. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered monthly following the week one administration, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

577. The method of embodiment 576, wherein the psoriasis is plaque psoriasis.

578. The method of embodiment 577, wherein the plaque psoriasis is moderate to severe plaque psoriasis.

579. The method of embodiment 578, wherein the moderate to severe plaque psoriasis is chronic moderate to severe plaque psoriasis and said patients are candidates for systemic therapy or phototherapy.

580. The method of embodiment 578, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

581. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

582. The method of embodiment 581, wherein the psoriasis is plaque psoriasis.

583. The method of embodiment 582, wherein the plaque psoriasis is moderate to severe plaque psoriasis.

584. The method of embodiment 583, wherein the moderate to severe plaque psoriasis is chronic moderate to severe plaque psoriasis and said patients are candidates for systemic therapy or phototherapy.

585. The method of embodiment 583, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

586. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

587. The method of embodiment 586, wherein the psoriasis is plaque psoriasis.

588. The method of embodiment 587, wherein the plaque psoriasis is moderate to severe plaque psoriasis.

589. The method of embodiment 588, wherein the moderate to severe plaque psoriasis is chronic moderate to severe plaque psoriasis and said patients are candidates for systemic therapy or phototherapy.

590. The method of embodiment 588, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

591. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

592. The method of embodiment 591, wherein the psoriasis is plaque psoriasis.

593. The method of embodiment 592, wherein the plaque psoriasis is moderate to severe plaque psoriasis.

594. The method of embodiment 593, wherein the moderate to severe plaque psoriasis is chronic moderate to severe plaque psoriasis and said patients are candidates for systemic therapy or phototherapy.

595. The method of embodiment 593, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

596. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

597. The method of embodiment 596, wherein the psoriasis is plaque psoriasis.

598. The method of embodiment 597, wherein the plaque psoriasis is moderate to severe plaque psoriasis.

599. The method of embodiment 598, wherein the moderate to severe plaque psoriasis is chronic moderate to severe plaque psoriasis and said patients are candidates for systemic therapy or phototherapy.

600. The method of embodiment 598, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

601. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered monthly following the week one administration, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

602. The method of embodiment 601, wherein the psoriasis is plaque psoriasis.

603. The method of embodiment 602, wherein the plaque psoriasis is moderate to severe plaque psoriasis.

604. The method of embodiment 603, wherein the moderate to severe plaque psoriasis is chronic moderate to severe plaque psoriasis and said patients are candidates for systemic therapy or phototherapy.

605. The method of embodiment 603, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

606. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of about 70 to about 300 mg antibody per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

607. The method of embodiment 606, wherein the psoriasis is plaque psoriasis.

608. The method of embodiment 607, wherein the plaque psoriasis is moderate to severe plaque psoriasis.

609. The method of embodiment 608, wherein the moderate to severe plaque psoriasis is chronic moderate to severe plaque psoriasis and said patients are candidates for systemic therapy or phototherapy.

610. The method of embodiment 608, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

611. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 70 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

612. The method of embodiment 611, wherein the psoriasis is plaque psoriasis.

613. The method of embodiment 612, wherein the plaque psoriasis is moderate to severe plaque psoriasis.

614. The method of embodiment 613, wherein the moderate to severe plaque psoriasis is chronic moderate to severe plaque psoriasis and said patients are candidates for systemic therapy or phototherapy.

615. The method of embodiment 613, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

616. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

617. The method of embodiment 616, wherein the psoriasis is plaque psoriasis.

618. The method of embodiment 617, wherein the plaque psoriasis is moderate to severe plaque psoriasis.

619. The method of embodiment 618, wherein the moderate to severe plaque psoriasis is chronic moderate to severe plaque psoriasis and said patients are candidates for systemic therapy or phototherapy.

620. The method of embodiment 618, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

621. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 210 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

622. The method of embodiment 621, wherein the psoriasis is plaque psoriasis.

623. The method of embodiment 622, wherein the plaque psoriasis is moderate to severe plaque psoriasis.

624. The method of embodiment 623, wherein the moderate to severe plaque psoriasis is chronic moderate to severe plaque psoriasis and said patients are candidates for systemic therapy or phototherapy.

625. The method of embodiment 623, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

626. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg per dose administered at time "0" (the first administration), at one week post time "0", and then administered monthly following the week one administration, wherein said antibody, or IL-17RA-binding fragment thereof, comprises a heavy chain sequence comprising SEQ ID NO:1 and a light chain sequence comprising SEQ ID NO:2.

627. The method of embodiment 626, wherein the psoriasis is plaque psoriasis.

628. The method of embodiment 627, wherein the plaque psoriasis is moderate to severe plaque psoriasis.

629. The method of embodiment 628, wherein the moderate to severe plaque psoriasis is chronic moderate to severe plaque psoriasis and said patients are candidates for systemic therapy or phototherapy.

630. The method of embodiment 628, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

631. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 210 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

632. The method of embodiment 631, wherein the psoriasis is plaque psoriasis.

633. The method of embodiment 632, wherein the plaque psoriasis is moderate to severe plaque psoriasis.

634. The method of embodiment 633, wherein the moderate to severe plaque psoriasis is chronic moderate to severe plaque psoriasis and said patients are candidates for systemic therapy or phototherapy.

635. The method of embodiment 633, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

636. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 210 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

637. The method of embodiment 636, wherein the psoriasis is plaque psoriasis.

638. The method of embodiment 637, wherein the plaque psoriasis is moderate to severe plaque psoriasis.

639. The method of embodiment 638, wherein the moderate to severe plaque psoriasis is chronic moderate to severe plaque psoriasis and said patients are candidates for systemic therapy or phototherapy.

640. The method of embodiment 638, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

641. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 210 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

642. The method of embodiment 641, wherein the psoriasis is plaque psoriasis.

643. The method of embodiment 642, wherein the plaque psoriasis is moderate to severe plaque psoriasis.

644. The method of embodiment 643, wherein the moderate to severe plaque psoriasis is chronic moderate to severe plaque psoriasis and said patients are candidates for systemic therapy or phototherapy.

645. The method of embodiment 643, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

646. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 280 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

647. The method of embodiment 646, wherein the psoriasis is plaque psoriasis.

648. The method of embodiment 647, wherein the plaque psoriasis is moderate to severe plaque psoriasis.

649. The method of embodiment 648, wherein the moderate to severe plaque psoriasis is chronic moderate to severe plaque psoriasis and said patients are candidates for systemic therapy or phototherapy.

650. The method of embodiment 648, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

651. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 280 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

652. The method of embodiment 651, wherein the psoriasis is plaque psoriasis.

653. The method of embodiment 652, wherein the plaque psoriasis is moderate to severe plaque psoriasis.

654. The method of embodiment 653, wherein the moderate to severe plaque psoriasis is chronic moderate to severe plaque psoriasis and said patients are candidates for systemic therapy or phototherapy.

655. The method of embodiment 653, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

656. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 280 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

657. The method of embodiment 656, wherein the psoriasis is plaque psoriasis.

658. The method of embodiment 657, wherein the plaque psoriasis is moderate to severe plaque psoriasis.

659. The method of embodiment 658, wherein the moderate to severe plaque psoriasis is chronic moderate to severe plaque psoriasis and said patients are candidates for systemic therapy or phototherapy.

660. The method of embodiment 658, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

661. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 210 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

662. The method of embodiment 661, wherein the psoriasis is plaque psoriasis.

663. The method of embodiment 662, wherein the plaque psoriasis is moderate to severe plaque psoriasis.

664. The method of embodiment 663, wherein the moderate to severe plaque psoriasis is chronic moderate to severe plaque psoriasis and said patients are candidates for systemic therapy or phototherapy.

665. The method of embodiment 663, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

666. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 210 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

667. The method of embodiment 666, wherein the psoriasis is plaque psoriasis.

668. The method of embodiment 667, wherein the plaque psoriasis is moderate to severe plaque psoriasis.

669. The method of embodiment 668, wherein the moderate to severe plaque psoriasis is chronic moderate to severe plaque psoriasis and said patients are candidates for systemic therapy or phototherapy.

670. The method of embodiment 668, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

671. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 210 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

672. The method of embodiment 671, wherein the psoriasis is plaque psoriasis.

673. The method of embodiment 672, wherein the plaque psoriasis is moderate to severe plaque psoriasis.

674. The method of embodiment 673, wherein the moderate to severe plaque psoriasis is chronic moderate to severe plaque psoriasis and said patients are candidates for systemic therapy or phototherapy.

675. The method of embodiment 673, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

676. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 280 mg every two weeks to patients weighing greater than 90 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

677. The method of embodiment 676, wherein the psoriasis is plaque psoriasis.

678. The method of embodiment 677, wherein the plaque psoriasis is moderate to severe plaque psoriasis.

679. The method of embodiment 678, wherein the moderate to severe plaque psoriasis is chronic moderate to severe plaque psoriasis and said patients are candidates for systemic therapy or phototherapy.

680. The method of embodiment 678, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

681. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 280 mg every two weeks to patients weighing greater than 100 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

682. The method of embodiment 681, wherein the psoriasis is plaque psoriasis.

683. The method of embodiment 682, wherein the plaque psoriasis is moderate to severe plaque psoriasis.

684. The method of embodiment 683, wherein the moderate to severe plaque psoriasis is chronic moderate to severe plaque psoriasis and said patients are candidates for systemic therapy or phototherapy.

685. The method of embodiment 683, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

686. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 280 mg every two weeks to patients weighing greater than 110 kg, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

687. The method of embodiment 686, wherein the psoriasis is plaque psoriasis.

688. The method of embodiment 687, wherein the plaque psoriasis is moderate to severe plaque psoriasis.

689. The method of embodiment 688, wherein the moderate to severe plaque psoriasis is chronic moderate to severe plaque psoriasis and said patients are candidates for systemic therapy or phototherapy.

690. The method of embodiment 688, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

691. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

692. The method of embodiment 691, wherein the psoriasis is plaque psoriasis.

693. The method of embodiment 692, wherein the plaque psoriasis is moderate to severe plaque psoriasis.

694. The method of embodiment 693, wherein the moderate to severe plaque psoriasis is chronic moderate to severe plaque psoriasis and said patients are candidates for systemic therapy or phototherapy.

695. The method of embodiment 693, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

696. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

697. The method of embodiment 696, wherein the psoriasis is plaque psoriasis.

698. The method of embodiment 697, wherein the plaque psoriasis is moderate to severe plaque psoriasis.

699. The method of embodiment 698, wherein the moderate to severe plaque psoriasis is chronic moderate to severe plaque psoriasis and said patients are candidates for systemic therapy or phototherapy.

700. The method of embodiment 698, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

701. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

702. The method of embodiment 701, wherein the psoriasis is plaque psoriasis.

703. The method of embodiment 702, wherein the plaque psoriasis is moderate to severe plaque psoriasis.

704. The method of embodiment 703, wherein the moderate to severe plaque psoriasis is chronic moderate to severe plaque psoriasis and said patients are candidates for systemic therapy or phototherapy.

705. The method of embodiment 703, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

706. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

707. The method of embodiment 706, wherein the psoriasis is plaque psoriasis.

708. The method of embodiment 707, wherein the plaque psoriasis is moderate to severe plaque psoriasis.

709. The method of embodiment 708, wherein the moderate to severe plaque psoriasis is chronic moderate to severe plaque psoriasis and said patients are candidates for systemic therapy or phototherapy.

710. The method of embodiment 708, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

711. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

712. The method of embodiment 711, wherein the psoriasis is plaque psoriasis.

713. The method of embodiment 712, wherein the plaque psoriasis is moderate to severe plaque psoriasis.

714. The method of embodiment 713, wherein the moderate to severe plaque psoriasis is chronic moderate to severe plaque psoriasis and said patients are candidates for systemic therapy or phototherapy.

715. The method of embodiment 713, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

716. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

717. The method of embodiment 716, wherein the psoriasis is plaque psoriasis.

718. The method of embodiment 717, wherein the plaque psoriasis is moderate to severe plaque psoriasis.

719. The method of embodiment 718, wherein the moderate to severe plaque psoriasis is chronic moderate to severe plaque psoriasis and said patients are candidates for systemic therapy or phototherapy.

720. The method of embodiment 718, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

721. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

722. The method of embodiment 721, wherein the psoriasis is plaque psoriasis.

723. The method of embodiment 722, wherein the plaque psoriasis is moderate to severe plaque psoriasis.

724. The method of embodiment 723, wherein the moderate to severe plaque psoriasis is chronic moderate to severe plaque psoriasis and said patients are candidates for systemic therapy or phototherapy.

725. The method of embodiment 723, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

726. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

727. The method of embodiment 726, wherein the psoriasis is plaque psoriasis.

728. The method of embodiment 727, wherein the plaque psoriasis is moderate to severe plaque psoriasis.

729. The method of embodiment 728, wherein the moderate to severe plaque psoriasis is chronic moderate to severe plaque psoriasis and said patients are candidates for systemic therapy or phototherapy.

730. The method of embodiment 728, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

731. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

732. The method of embodiment 731, wherein the psoriasis is plaque psoriasis.

733. The method of embodiment 732, wherein the plaque psoriasis is moderate to severe plaque psoriasis.

734. The method of embodiment 733, wherein the moderate to severe plaque psoriasis is chronic moderate to severe plaque psoriasis and said patients are candidates for systemic therapy or phototherapy.

735. The method of embodiment 733, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

736. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

737. The method of embodiment 736, wherein the psoriasis is plaque psoriasis.

738. The method of embodiment 737, wherein the plaque psoriasis is moderate to severe plaque psoriasis.

739. The method of embodiment 738, wherein the moderate to severe plaque psoriasis is chronic moderate to severe plaque psoriasis and said patients are candidates for systemic therapy or phototherapy.

740. The method of embodiment 738, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

741. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

742. The method of embodiment 741, wherein the psoriasis is plaque psoriasis.

743. The method of embodiment 742, wherein the plaque psoriasis is moderate to severe plaque psoriasis.

744. The method of embodiment 743, wherein the moderate to severe plaque psoriasis is chronic moderate to severe plaque psoriasis and said patients are candidates for systemic therapy or phototherapy.

745. The method of embodiment 743, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

746. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

747. The method of embodiment 746, wherein the psoriasis is plaque psoriasis.

748. The method of embodiment 747, wherein the plaque psoriasis is moderate to severe plaque psoriasis.

749. The method of embodiment 748, wherein the moderate to severe plaque psoriasis is chronic moderate to severe plaque psoriasis and said patients are candidates for systemic therapy or phototherapy.

750. The method of embodiment 748, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

751. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

752. The method of embodiment 751, wherein the psoriasis is plaque psoriasis.

753. The method of embodiment 752, wherein the plaque psoriasis is moderate to severe plaque psoriasis.

754. The method of embodiment 753, wherein the moderate to severe plaque psoriasis is chronic moderate to severe plaque psoriasis and said patients are candidates for systemic therapy or phototherapy.

755. The method of embodiment 753, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

756. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

757. The method of embodiment 756, wherein the psoriasis is plaque psoriasis.

758. The method of embodiment 757, wherein the plaque psoriasis is moderate to severe plaque psoriasis.

759. The method of embodiment 758, wherein the moderate to severe plaque psoriasis is chronic moderate to severe plaque psoriasis and said patients are candidates for systemic therapy or phototherapy.

760. The method of embodiment 758, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

761. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

762. The method of embodiment 761, wherein the psoriasis is plaque psoriasis.

763. The method of embodiment 762, wherein the plaque psoriasis is moderate to severe plaque psoriasis.

764. The method of embodiment 763, wherein the moderate to severe plaque psoriasis is chronic moderate to severe plaque psoriasis and said patients are candidates for systemic therapy or phototherapy.

765. The method of embodiment 763, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

766. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

767. The method of embodiment 766, wherein the psoriasis is plaque psoriasis.

768. The method of embodiment 767, wherein the plaque psoriasis is moderate to severe plaque psoriasis.

769. The method of embodiment 768, wherein the moderate to severe plaque psoriasis is chronic moderate to severe plaque psoriasis and said patients are candidates for systemic therapy or phototherapy.

770. The method of embodiment 768, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

771. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

772. The method of embodiment 771, wherein the psoriasis is plaque psoriasis.

773. The method of embodiment 772, wherein the plaque psoriasis is moderate to severe plaque psoriasis.

774. The method of embodiment 773, wherein the moderate to severe plaque psoriasis is chronic moderate to severe plaque psoriasis and said patients are candidates for systemic therapy or phototherapy.

775. The method of embodiment 773, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

776. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 140 mg every two weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

777. The method of embodiment 776, wherein the psoriasis is plaque psoriasis.

778. The method of embodiment 777, wherein the plaque psoriasis is moderate to severe plaque psoriasis.

779. The method of embodiment 778, wherein the moderate to severe plaque psoriasis is chronic moderate to severe plaque psoriasis and said patients are candidates for systemic therapy or phototherapy.

780. The method of embodiment 778, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

781. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 210 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

782. The method of embodiment 781, wherein the psoriasis is plaque psoriasis.

783. The method of embodiment 782, wherein the plaque psoriasis is moderate to severe plaque psoriasis.

784. The method of embodiment 783, wherein the moderate to severe plaque psoriasis is chronic moderate to severe plaque psoriasis and said patients are candidates for systemic therapy or phototherapy.

785. The method of embodiment 783, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

786. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 210 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

787. The method of embodiment 786, wherein the psoriasis is plaque psoriasis.

788. The method of embodiment 787, wherein the plaque psoriasis is moderate to severe plaque psoriasis.

789. The method of embodiment 788, wherein the moderate to severe plaque psoriasis is chronic moderate to severe plaque psoriasis and said patients are candidates for systemic therapy or phototherapy.

790. The method of embodiment 788, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

791. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 210 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

792. The method of embodiment 791, wherein the psoriasis is plaque psoriasis.

793. The method of embodiment 792, wherein the plaque psoriasis is moderate to severe plaque psoriasis.

794. The method of embodiment 793, wherein the moderate to severe plaque psoriasis is chronic moderate to severe plaque psoriasis and said patients are candidates for systemic therapy or phototherapy.

795. The method of embodiment 793, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

796. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 90 kg and a single or divided dose of 280 mg every two weeks to patients weighing greater than 90 kg, wherein said antibody, or IL-17RA-binding fragment thereof, comprises a heavy chain sequence comprising SEQ ID NO:1 and a light chain sequence comprising SEQ ID NO:2.

797. The method of embodiment 796, wherein the psoriasis is plaque psoriasis.

798. The method of embodiment 797, wherein the plaque psoriasis is moderate to severe plaque psoriasis.

799. The method of embodiment 798, wherein the moderate to severe plaque psoriasis is chronic moderate to severe plaque psoriasis and said patients are candidates for systemic therapy or phototherapy.

800. The method of embodiment 798, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

801. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 100 kg and a single or divided dose of 280 mg every two weeks to patients weighing greater than 100 kg, wherein said antibody, or IL-17RA-binding fragment thereof, comprises a heavy chain sequence comprising SEQ ID NO:1 and a light chain sequence comprising SEQ ID NO:2.

802. The method of embodiment 801, wherein the psoriasis is plaque psoriasis.

803. The method of embodiment 802, wherein the plaque psoriasis is moderate to severe plaque psoriasis.

804. The method of embodiment 803, wherein the moderate to severe plaque psoriasis is chronic moderate to severe plaque psoriasis and said patients are candidates for systemic therapy or phototherapy.

805. The method of embodiment 803, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

806. A method of treating psoriasis in adult and/or juvenile patients having psoriasis, comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose of 280 mg every four weeks to patients weighing less than or approximately equal to 110 kg and a single or divided dose of 280 mg every two weeks to patients weighing greater than 110 kg, wherein said antibody, or IL-17RA-binding fragment thereof, comprises a heavy chain sequence comprising SEQ ID NO:1 and a light chain sequence comprising SEQ ID NO:2.

807. The method of embodiment 806, wherein the psoriasis is plaque psoriasis.

808. The method of embodiment 807, wherein the plaque psoriasis is moderate to severe plaque psoriasis.

809. The method of embodiment 808, wherein the moderate to severe plaque psoriasis is chronic moderate to severe plaque psoriasis and said patients are candidates for systemic therapy or phototherapy.

810. The method of embodiment 808, wherein the moderate to severe plaque psoriasis is chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

811. A pharmaceutical formulation, comprising an aqueous solution of a glutamic acid buffer and an antibody comprising a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, wherein said antibody, or fragment thereof, specifically binds human IL-17 receptor A, and wherein:
 a) said glutamic acid buffer comprises a glutamic acid concentration of 5-30 mM±0.2 mM;
 b) said glutamic acid buffer comprises a pH of 4.5-5.2±0.2;
 c) said formulation further comprises 2-4% proline (w/v) and 0.005-0.02% (w/v) polysorbate 20; and
 d) said antibody is at a concentration of 100 to 150 mg/ml.

812. The pharmaceutical formulation of claim 1, wherein the antibody or fragment thereof comprises a heavy chain variable domain sequence comprising SEQ ID NO:3 and a light chain variable domain sequence comprising SEQ ID NO:4.

813. The pharmaceutical formulation of claim 1, wherein the antibody comprises a heavy chain sequence comprising SEQ ID NO:1 and a light chain sequence comprising SEQ ID NO:2, or alternatively, a heavy chain sequence comprising SEQ ID NO:12 and the light chain sequence comprising SEQ ID NO:2.

814. The pharmaceutical formulation of embodiment 811, wherein the glutamic acid buffer or acetic acid buffer concentration is 10 mM±0.2 mM.

815. The pharmaceutical formulation of embodiment 811, wherein the formulation has a pH of 4.8±0.2.

816 The pharmaceutical formulation of embodiment 811, having an isotonic or near-isotonic osmolarity of 250 to 400 osm.

817. The pharmaceutical formulation of embodiment 811, having an isotonic or near-isotonic osmolarity of 275 to 325 osm.

818. The pharmaceutical formulation of embodiment 811, comprising an osmolarity of about 300 osm/L.

819 The pharmaceutical formulation of embodiment 811, comprising 100-200 mg/mL AM-14, formulated with 5-15 mM glutamic acid, 7-9% (w/v) sucrose, 0.005-0.02% (w/v) polysorbate 20, pH 4.5-5.5±0.2.

820. The pharmaceutical formulation of embodiment 811, comprising about 140 mg/mL AM-14, formulated with 10±0.2 mM glutamic acid, 8±0.2% (w/v) sucrose, 0.01±0.002% (w/v) polysorbate 20, pH 4.8±0.2.

821. The pharmaceutical formulation of embodiment 811, comprising 100-200 mg/mL AM-14, formulated with 5-15 mM glutamic acid, 1-3% (w/v) glycine, 0.005-0.02% (w/v) polysorbate 20, pH 4.5-5.5±0.2.

822. The pharmaceutical formulation of embodiment 811, comprising about 140 mg/mL AM-14, formulated with 10±0.2 mM glutamic acid, 2±0.2% (w/v) glycine, 0.01±0.002% (w/v) polysorbate 20, pH 4.8±0.2.

823. The pharmaceutical formulation of embodiment 811, comprising 100-200 mg/mL AM-14, formulated with 5-15 mM glutamic acid, 2-4% (w/v) proline, 0.005-0.02% (w/v) polysorbate 20, pH 4.5-5.5±0.2.

824. The pharmaceutical formulation of embodiment 811, comprising about 140 mg/mL AM-14, formulated with 10±0.2 mM glutamic acid, 3±0.2% (w/v) L-proline, 0.01±0.002% (w/v) polysorbate 20, pH 4.8±0.2.

825. The pharmaceutical formulation of embodiment 811, comprising 100-200 mg/mL AM-14, formulated with 5-15 mM acetic acid, 1-3% (w/v) glycine, 0.005-0.02% (w/v) polysorbate 20, pH 4.5-5.5±0.2.

826. The pharmaceutical formulation of embodiment 81, comprising about 140 mg/mL AM-14, formulated with 10±0.2 mM acetic acid, 2±0.2% (w/v) glycine, 0.01±0.002% (w/v) polysorbate 20, pH 4.8±0.2.

827. The pharmaceutical formulation of embodiment 811, comprising 100-200 mg/mL AM-14, formulated with 5-15 mM acetic acid, 2-4% (w/v) proline, 0.005-0.02% (w/v) polysorbate 20, pH 4.5-5.5±0.2.

828. The pharmaceutical formulation of embodiment 811, comprising about 140 mg/mL AM-14, formulated with 10±0.2 mM acetic acid, 3±0.2% (w/v) L-proline, 0.01±0.002% (w/v) polysorbate 20, pH 4.8±0.2.

829. The pharmaceutical formulation of embodiment 811, comprising 100-200 mg/mL AM-14, formulated with 5-15 mM acetic acid, 7-9% (w/v) sucrose, 0.005-0.02% (w/v) polysorbate 20, pH 4.5-5.5±0.2.

830. The pharmaceutical formulation of embodiment 811, comprising about 140 mg/mL AM-14, formulated with 10±0.2 mM acetic acid, 8±0.2% (w/v) sucrose, 0.01±0.002% (w/v) polysorbate 20, pH 4.8±0.2.

831. The pharmaceutical formulation of embodiment 811, comprising 100-200 mg/mL AM-14, formulated with 5-15 mM acetic acid, 2-4% (w/v) glycerol, 0.005-0.02% (w/v) polysorbate 20, pH 4.5-5.5±0.2.

832. The pharmaceutical formulation of embodiment 811, comprising about 140 mg/mL AM-14, formulated with 10±0.2 mM acetic acid, 3±0.2% (w/v) glycerol, 0.01±0.002% (w/v) polysorbate 20, pH 4.8±0.2.

833. The pharmaceutical formulation of embodiment 811, comprising 100-200 mg/mL AM-14, formulated with 5-15 mM acetic acid, 3.5-5.5% (w/v) sorbitol, 0.005-0.02% (w/v) polysorbate 20, pH 4.5-5.5±0.2.

834. The pharmaceutical formulation of embodiment 811, comprising about 140 mg/mL AM-14, formulated with 10±0.2 mM acetic acid, 4.5±0.2% (w/v) sorbitol, 0.01±0.002% (w/v) polysorbate 20, pH 4.8±0.2.

835. The pharmaceutical formulation according to any of embodiments 811 to 834, wherein said formulation has a viscosity of 4 to 10 cP at 25 degrees C.

836. The pharmaceutical formulation according to any of embodiments 811 to 834, wherein said formulation has a viscosity of 5 to 7 cP at 25 degrees C.

837. A method of preparing a pharmaceutical formulation, comprising combining an aqueous solution of a glutamic acid or acetic acid buffer and an isolated antibody, or IL-17RA-binding fragment thereof, comprising a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, wherein said antibody specifically binds human IL-17 receptor A, and wherein:
  a) said aqueous solution of a glutamic acid or acetic acid buffer comprises a pH of 4.5 to 5.2±0.2;
  b) said glutamic acid or acetic acid buffer comprises a glutamic acid or acetic concentration of 5 to 30 mM±0.2 mM;
  c) said formulation comprises an excipient selected from the group consisting of sucrose, glycine, proline, glycerol and/or sorbitol at a concentration of 1 to 20%±0.2% (w/v); and
  d) said antibody comprises a concentration of 100 to 200 mg/ml.

838. A pharmaceutical container, comprising a vessel and an aqueous solution of the pharmaceutical formulation of any of embodiments 811 to 836.

839. The pharmaceutical container of embodiment 838, wherein the vessel is a vial, bottle, or a pre-filled syringe.

840. A kit, comprising one or more pharmaceutical containers according to embodiment 838 and instructions regarding the use thereof.

841. A method of treating IL-17-related inflammation in a human patient in need thereof, comprising administering to the patient a single or divided 70 to 1,000 mg dose of the pharmaceutical formulation of any of embodiments 811 to 836.

842. The method of embodiment 841, wherein the single or divided dose of the pharmaceutical formulation of any of embodiments 811 to 836 is administered subcutaneously, intravenously, parenterally, intradermally, intramuscularly, and/or intraperitoneally.

843. The method of embodiment 841, wherein the single or divided dose of the pharmaceutical formulation of any of embodiments 811 to 836 is approximately 140 to 800 mg and is administered by subcutaneous injection, intradermal administration, and/or intravenously.

844. A method of treating IL-17-related autoimmune disease in a human patient in need thereof, comprising administering to the patient a single or divided 70 to 1,000 mg dose of the pharmaceutical formulation of any of embodiments 811 to 836 at least once every one to six weeks.

845. The method of embodiment 844, wherein the single or divided dose of the pharmaceutical formulation of any of embodiments 811 to 836 is administered subcutaneously, intravenously, parenterally, intradermally, intramuscularly, and/or intraperitoneally.

846. The method of embodiment 844, wherein the single or divided dose of the pharmaceutical formulation of any of embodiments 811 to 836 is approximately 140 to 800 mg and is administered by subcutaneous injection, intradermal administration, and/or intravenously.

847. A method of treating psoriasis in a human patient in need thereof, comprising administering to the patient a single or divided 70 to 1,000 mg dose of the pharmaceutical formulation of any of embodiments 811 to 836 at least once every one to six weeks.

848. The method of embodiment 847, wherein the single or divided dose of the pharmaceutical formulation of any of embodiments 811 to 836 is administered subcutaneously, intravenously, parenterally, intradermally, intramuscularly, and/or intraperitoneally.

849. The method of embodiment 847, wherein the single or divided dose of the pharmaceutical formulation of any of embodiments 811 to 836 is approximately 140 to 300 mg and is administered by subcutaneous injection, intradermally, and/or intravenously.

850. A method of regulating the expression of one or more of the genes in tables 3.1, 3.2, and/or 3.3 in a psoriasis patient comprising administering an effective amount of AM-14 to the patient.

851. A method of regulating the expression of one or more of the genes in tables 3.1, 3.2, and/or 3.3 in a psoriasis patient and concomitantly reducing the PASI score in the patient by at least 10, 15, 20, 25, 30, 35, 40, 45, 50, 55, 60, 65, 70, 75, 80, 85, 90, 95, or 100% comprising administering an effective amount of AM-14 to the patient.

852. A method of regulating the expression of one or more of the genes in tables 3.1, 3.2, and/or 3.3 in 15 days or less in a psoriasis patient and concomitantly reducing the PASI score in the patient by at least 10, 15, 20, 25, 30, 35, 40, 45, 50, 55, 60, 65, 70, 75, 80, 85, 90, 95, or 100% comprising administering an effective amount of AM-14 to the patient.

853. A method of regulating the expression of one or more of the genes in tables 3.1, 3.2, and/or 3.3 in a psoriasis patient comprising administering an effective amount of an antibody that binds IL-17RA and prevents the activation of IL-17RA by one or more IL-17 ligands.

854. A method of regulating the expression of one or more of the genes in tables 3.1, 3.2, and/or 3.3 in a psoriasis patient and concomitantly reducing the PASI score in the patient by at least 10, 15, 20, 25, 30, 35, 40, 45, 50, 55, 60, 65, 70, 75, 80, 85, 90, 95, or 100% comprising administering an effective amount of an antibody that binds IL-17RA and prevents the activation of IL-17RA by one or more IL-17 ligands.

855. A method of regulating the expression of one or more of the genes in tables 3.1, 3.2, and/or 3.3 in 15 days or less in a psoriasis patient and concomitantly reducing the PASI score in the patient by at least 10, 15, 20, 25, 30, 35, 40, 45, 50, 55, 60, 65, 70, 75, 80, 85, 90, 95, or 100% comprising administering an effective amount of an antibody that binds IL-17RA and prevents the activation of IL-17RA by one or more IL-17 ligands.

856. A method of regulating the expression of one or more of the genes in tables 3.1, 3.2, and/or 3.3 in a psoriasis patient comprising administering an effective amount of a monoclonal antibody that specifically binds human IL-17A.

857. A method of regulating the expression of one or more of the genes in tables 3.1, 3.2, and/or 3.3 in a psoriasis patient and concomitantly reducing the PASI score in the patient by at least 10, 15, 20, 25, 30, 35, 40, 45, 50, 55, 60, 65, 70, 75, 80, 85, 90, 95, or 100% comprising administering an effective amount of a monoclonal antibody that specifically binds human IL-17A.

858. A method of regulating the expression of one or more of the genes in tables 3.1, 3.2, and/or 3.3 in a psoriasis patient and concomitantly reducing the PASI score in the patient by at least 50% comprising administering an effective amount of a monoclonal antibody that specifically binds human IL-17A.

859. A method of regulating the expression of one or more of the genes in tables 3.1, 3.2, and/or 3.3 in a psoriasis patient and concomitantly reducing the PASI score in the patient by at least 75% comprising administering an effective amount of a monoclonal antibody that specifically binds human IL-17A.

860. A method of regulating the expression of one or more of the genes in tables 3.1, 3.2, and/or 3.3 in a psoriasis patient comprising administering an effective amount of AM-14 to the patient.

861. A method of regulating the expression of one or more of the genes in tables 3.1, 3.2, and/or 3.3 in a psoriasis patient comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

862. A method of regulating the expression of one or more of the genes in tables 3.1, 3.2, and/or 3.3 in a psoriasis patient comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

863. A method of regulating the expression of one or more of the genes in tables 3.1, 3.2, and/or 3.3 in a psoriasis patient comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain sequence comprising SEQ ID NO:1 and a light chain sequence comprising SEQ ID NO:2.

864. A method of regulating the expression of one or more of the genes in tables 3.1, 3.2, and/or 3.3 in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

865. A method of regulating the expression of one or more of the genes in tables 3.1, 3.2, and/or 3.3 in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

866. A method of regulating the expression of one or more of the genes in tables 3.1, 3.2, and/or 3.3 in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain sequence comprising SEQ ID NO:1 and a light chain sequence comprising SEQ ID NO:2.

867. A method of regulating the expression of one or more of the genes in tables 3.1, 3.2, and/or 3.3 in 15 days or less in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody comprises a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, and wherein said antibody specifically binds human IL-17 receptor A.

868. A method of regulating the expression of one or more of the genes in tables 3.1, 3.2, and/or 3.3 in 15 days or less in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain variable domain sequence comprising SEQ ID NO:3 and a light chain variable domain sequence comprising SEQ ID NO:4, and wherein said antibody specifically binds human IL-17 receptor A.

869. A method of regulating the expression of one or more of the genes in tables 3.1, 3.2, and/or 3.3 in 15 days or less in a psoriasis patient and concomitantly reducing the PASI score in the patient by at least 75% comprising administering to said patient a pharmaceutical composition comprising 10 mM glutamic acid, 3% (w/v) L-proline, 0.01% (w/v) polysorbate 20, pH 4.8±0.2 and 140 mg/mL of an antibody in a single or divided dose, wherein said antibody, or IL-17RA-binding fragment thereof, comprises a heavy chain sequence comprising SEQ ID NO:1 and a light chain sequence comprising SEQ ID NO:2.

870. A pharmaceutical formulation, comprising an aqueous solution of a glutamic acid buffer and an antibody comprising a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, wherein said antibody, or fragment thereof, specifically binds human IL-17 receptor A, and wherein:
  a) said glutamic acid buffer comprises a glutamic acid concentration of 5-30 mM±0.2 mM;
  b) said glutamic acid buffer comprises a pH of 4.5-5.2±0.2;
  c) said formulation further comprises 2-4% proline (w/v) and 0.005-0.02% (w/v) polysorbate 20; and
  d) said antibody is at a concentration of 100 to 150 mg/ml.

871. The pharmaceutical formulation of embodiment 870, wherein the antibody or fragment thereof comprises a heavy chain variable domain sequence comprising SEQ ID NO:3 and a light chain variable domain sequence comprising SEQ ID NO:4.

872. The pharmaceutical formulation of embodiment 870, wherein the antibody comprises a heavy chain sequence comprising SEQ ID NO:1 and a light chain sequence comprising SEQ ID NO:2, or alternatively, a heavy chain sequence comprising SEQ ID NO:12 and the light chain sequence comprising SEQ ID NO:2.

873. The pharmaceutical formulation of embodiment 870, further comprising an osmolarity of 275 to 325 osm.

874. The pharmaceutical formulation of embodiment 870, further comprising a viscosity of 5 to 7 cP at 25 degrees C.

875. The pharmaceutical formulation of embodiment 870, comprising about 140 mg/mL of said antibody, formulated with 10±0.2 mM glutamic acid, 3±0.2% (w/v) L-proline, 0.01±0.002% (w/v) polysorbate 20, pH 4.8±0.2.

876. The pharmaceutical formulation of embodiment 871, comprising about 140 mg/mL of said antibody, formulated with 10±0.2 mM glutamic acid, 3±0.2% (w/v) L-proline, 0.01±0.002% (w/v) polysorbate 20, pH 4.8±0.2.

877. The pharmaceutical formulation of embodiment 872, comprising about 140 mg/mL of said antibody, formulated with 10±0.2 mM glutamic acid, 3±0.2% (w/v) L-proline, 0.01±0.002% (w/v) polysorbate 20, pH 4.8±0.2.

878. A pharmaceutical container, comprising a vessel and the pharmaceutical formulation of any of embodiments 880 to 877, wherein the vessel is a vial, bottle, pre-filled syringe, or pre-filled autoinjector syringe.

879. A kit, comprising one or more pharmaceutical containers according to embodiment 878 and instructions regarding the use thereof.

880. A method of treating psoriasis in a human patient in need thereof, comprising administering to the patient a single or divided 70 to 1,000 mg dose of an antibody, wherein said antibody is selected from the group consisting of:
  a) an antibody comprising a heavy chain CDR1 comprising SEQ ID NO:5, a heavy chain CDR2 comprising SEQ ID NO:7, a heavy chain CDR3 comprising SEQ ID NO:8, a light chain CDR1 comprising SEQ ID NO:9, a light chain CDR2 comprising SEQ ID NO:10, and a light chain CDR3 comprising SEQ ID NO:11, wherein said antibody, or fragment thereof, specifically binds human IL-17 receptor A;
  b) an antibody comprising a heavy chain variable domain sequence comprising SEQ ID NO:3 and a light chain variable domain sequence comprising SEQ ID NO:4, wherein said antibody, or fragment thereof, specifically binds human IL-17 receptor A; and
  c) an antibody comprising a heavy chain sequence comprising SEQ ID NO:1 and a light chain sequence comprising SEQ ID NO:2, or alternatively, a heavy chain sequence comprising SEQ ID NO:12 and the light chain sequence comprising SEQ ID NO:2.

881. The method of embodiment 880, wherein said patient is administered a single or divided 70 to 280 mg dose of said antibody administered at time "0" (the first administration), at one week post time "0" (week one), and then administered every two to four weeks following the week one administration.

882. The method of embodiment 881, wherein a single or divided dose of 140 mg of said antibody is administered at time "0" (the first administration), at one week post time "0" (week one), and then administered every two weeks to patients weighing less than or approximately equal to 100 kg, and wherein a single or divided dose of 280 mg of said antibody is administered at time "0" (the first administration), at one week post time "0" (week one), and then administered every two weeks to patients weighing greater than 100 kg.

883. The method of any of embodiments 880 to 882, wherein the psoriasis is selected from the group consisting of:
  a) plaque psoriasis;
  b) moderate to severe plaque psoriasis;
  c) chronic moderate to severe plaque psoriasis and said patients are candidates for systemic therapy or phototherapy; and
  d) chronic moderate to severe plaque psoriasis and wherein said patients have failed to respond to, have a contraindication to, or are intolerant to other systemic therapies including cyclosporin, methotrexate, and psoralen plus ultraviolet-A phototherapy.

884. The method of any of embodiments 880 to 883, wherein said antibody is in a pharmaceutical formulation comprising about 140 mg/mL of said antibody, formulated with 10±0.2 mM glutamic acid, 3±0.2% (w/v) L-proline, 0.01±0.002% (w/v) polysorbate 20, pH 4.8±0.2.

885. The method of embodiment 884, wherein the pharmaceutical formulation is administered subcutaneously, intradermally, intramuscularly, and/or intravenously.

TABLE A

| AM-14 sequences | | |
|---|---|---|
| AM-14 full-length heavy chain | SEQ ID NO: 1 | QVQLVQSGAEVKKPGASVKVSCKASGYTFTR YGISWVRQAPGQGLEWMGWISTYSGNTNYA QKLQGRVTMTTDTSTSTAYMELRSLRSDDTA VYYCARRQLYFDYWGQGTLVTVSSASTKGPS VFPLAPCSRSTSESTAALGCLVKDYFPEPVTV SWNSGALTSGVHTFPAVLQSSGLYSLSSVVT |

TABLE A-continued

AM-14 sequences

```
VPSSNFGTQTYTCNVDHKPSNTKVDKTVERK
CCVECPPCPAPPVAGPSVFLFPPKPKDTLMIS
RTPEVTCVVVDVSHEDPEVQFNWYVDGVEV
HNAKTKPREEQFNSTFRVVSVLTVVHQDWLN
GKEYKCKVSNKGLPAPIEKTISKTKGQPREPQ
VYTLPPSREEMTKNQVSLTCLVKGFYPSDIAV
EWESNGQPENNYKTTPPMLDSDGSFFLYSKL
TVDKSRWQQGNVFSCSVMHEALHNHYTQKS
LSLSPGK
```

EXAMPLES

Example 1

AM-14 Formulations

Numerous formulations were prepared using lab scale UF/DF (ultrafiltration/diafiltration) system at room temperature for the purpose of identifying excipients and formulations that are uniquely suited for AM-14. The UF/DF buffers were prepared at lower pH (3.5, 3.8 or 4.0) with glutamic acid or acetic acid as buffering agents and various excipients including sucrose, L-proline, glycine, sorbitol, and others.

Sample preparation from lyophilized vials for reconstitution of AM-14 at a higher concentration (180 mg/mL) was performed as follows: UF/DF of AM-14 final purified bulk (FPB) was performed from 70 mg/mL A52Su (10 mM acetic acid, 9% sucrose, pH 5.2)[ ] formulation to approximately 90 mg/mL with a 5-fold increase in diafiltration volume (ml) of a) 10 mM glutamate, 0.5% sucrose, pH 4.2, and b) 10 mM glutamate, 0.5% sucrose, pH 5.2, respectively. After UF/DF, the resulting concentrations for the above two conditions were 90.8 mg/mL at pH 5.33 for a), and 89.6 mg/mL at pH 5.63 for b) buffers, respectively. The AM-14 formulations were filtered through 0.45 micron filters and 1.25 mL were filled into 3 cc glass vials. The formulations were lyophilized. The samples prepared from buffer a) are denoted with E4.5_ (i.e., 10 mM glutamate, pH 4.5), and samples from buffer b) are denoted with E5.5_ (i.e., 10 mM glutamate, pH 5.5). At room temperature, E4.5 vials were reconstituted with 0.685 mL of one of the diluents listed in Table 1.0) and E5.5 vials were reconstituted with 0.596 mL of one of the diluents listed in Table 1.0), which is approximately half of its initial fill volume, resulting in the reconstituted formulations having a final concentration of 20 mM glutamate. After the lyophilized cakes were dissolved, the samples were ready for viscosity measurement.

Figure 2:
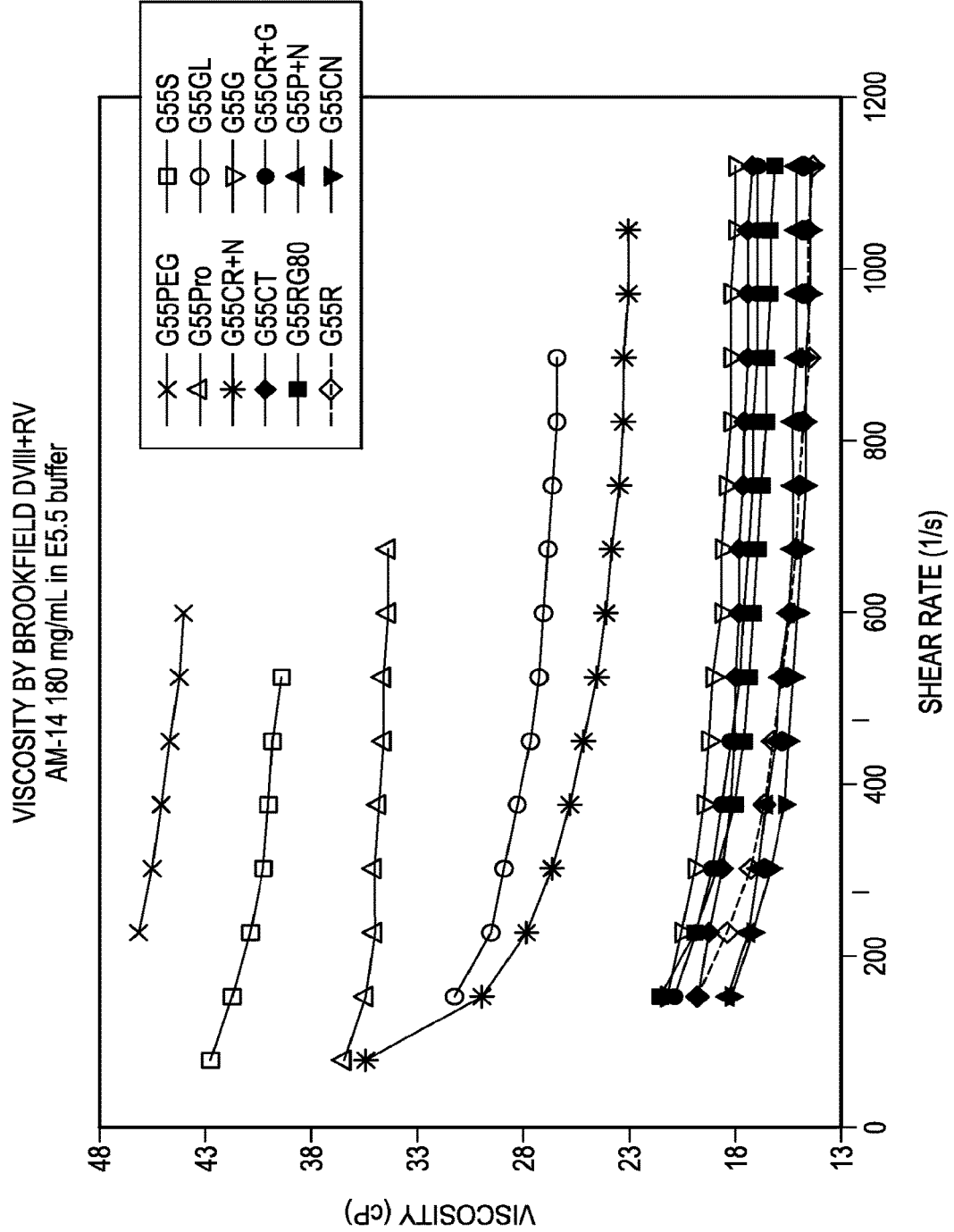
FIG. 2: A graph illustrating the relationship between viscosity and shear rate for various AM-14 formulations. Various excipients were evaluated in a 10 mM glutamate, pH 5.5 buffer with AM-14 held constant at approximately 180 mg/ml.

The viscosity of the protein liquid formulations was measured by a rheometer with the cone/plate geometry (RV 111+ model, Brookfield Engineering Labs, Inc., Middleboro, Mass.). Sample temperature was maintained at 25° C. during measurement with a water bath. The spindle speed ranged from 15 to 125 rpm with 10 rpm per increment. Data collection was carried out with Rheocalc™ software, version 2.7. At each shear condition, 4 readings were collected with 10 second interval, and each data point was the average of the 4 readings. After a new shear condition was established, the first reading was made after 30 second waiting time. See Tables 1.0 and 1.1. The viscosity results for the formulations listed in Table 1.0 were graphed as a function of shear stress and are shown in FIGS. 1 and 2.

With reference to Table 1.1, Formulation 1, having a final pH of 5.11, and Formulation 2, having a final pH of 3.33, showed significantly higher viscosity, while those formulations having a pH of 4.55 to 4.93 had much lower viscosity, demonstrating a clear optimal range of pH in a highly concentrated formulation of AM-14 that yielded lower viscosity.

TABLE 1.0

AM-14 concentrations at approximately 180 mg/ml

| Reconstitution Buffer/pH | Excipient | Viscosity (cP) | AM-14 Final pH | Clarity |
| --- | --- | --- | --- | --- |
| 10 mM glutamate, pH 4.5 | 4% sorbitol | 19.64 | 5.24 | clear |
| 10 mM glutamate, pH 4.5 | 200 mM PEG200 | 32.31 | 5.29 | clear |
| 10 mM glutamate, pH 4.5 | 2.5% glycerol (271.5 mM) | 18.29 | 5.24 | clear |
| 10 mM glutamate, pH 4.5 | 3% proline (260 mM) | 19.99 | 5.28 | clear |
| 10 mM glutamate, pH 4.5 | 160 mM glutamic acid | 12.50 | 4.98 | clear |
| 10 mM glutamate, pH 4.5 | 200 mM creatinine | 11.89 | 4.6 | clear |
| 10 mM glutamate, pH 4.5 | 200 mM L-carnitine | 12.85 | 4.8 | clear |
| 10 mM glutamate, pH 4.5 | 50 mM creatinine + 70 mM NaCl | 17.15 | 5.2 | clear |
| 10 mM glutamate, pH 4.5 | 50 mM creatinine + 110 mM glutamic acid | 12.77 | 4.9 | clear |
| 10 mM glutamate, pH 4.5 | 80 mM arginine + 80 mM glutamic acid | 14.85 | 5.05 | clear |
| 10 mM glutamate, pH 4.5 | 130 mM proline + 70 mM NaCl | 17.25 | 5.39 | clear |
| 10 mM glutamate, pH 4.5 | 160 mM glycine | 15.42 | 5.12 | clear |
| 10 mM glutamate, pH 4.5 | 160 mM betaine | 20.75 | 5.13 | clear |
| 10 mM glutamate, pH 5.5 | 4% sorbitol | 44.20 | 5.6 | clear |
| 10 mM glutamate, pH 5.5 | 200 mM PEG200 | 39.45 | 5.6 | clear |
| 10 mM glutamate, pH 5.5 | 2.5% glycerol (271.5 mM) | 34.5 | 5.6 | clear |
| 10 mM glutamate, pH 5.5 | 3% proline (260 mM) | 27.3 | 5.65 | clear |
| 10 mM glutamate, pH 5.5 | 160 mM glutamic acid | 19.02 | 5.7 | clear |

TABLE 1.0-continued

AM-14 concentrations at approximately 180 mg/ml

| Reconstitution Buffer/pH | Excipient | Viscosity (cP) | AM-14 Final pH | Clarity |
|---|---|---|---|---|
| 10 mM glutamate, pH 5.5 | 160 mM arginine-HCl, pH 5.5 | 15.74 | 5.7 | clear |
| 10 mM glutamate, pH 5.5 | 200 mM creatinine | 15.22 | 5.6 | clear |
| 10 mM glutamate, pH 5.5 | 200 mM L-carnitine | 18.07 | 5.6 | clear |
| 10 mM glutamate, pH 5.5 | 50 mM creatinine + 70 mM NaCl | 24.62 | 6.08 | clear |
| 10 mM glutamate, pH 5.5 | 50 mM creatinine + 110 mM glutamic acid | 17.97 | 5.7 | clear |
| 10 mM glutamate, pH 5.5 | 80 mM arginine + 80 mM glutamic acid | 17.42 | 5.69 | clear |
| 10 mM glutamate, pH 5.5 | 130 mM proline + 70 mM NaCl | 15.88 | 5.76 | hazy |

TABLE 1.1

Effect of pH on viscosity for highly concentrated AM-14 formulations

| Formulation | Formulation components | Excipient | Buffer | Buffer pH | Final pH | AM-14 Concentration (mg/mL) | Viscosity (cP) |
|---|---|---|---|---|---|---|---|
| 1. A48SuT | acetic acid; sucrose, and polysorbate 20 | Sucrose | Acetate | 3.8 | 5.11 | 148.95 | 12.61 |
| 2. E44GT | Glutamic acid, glycine, and polysorbate 20 | Glycine | L-glutamic acid | 3.2 | 3.33 | 148 | 19.60 |
| 3. A48GT | acetic acid, glycine, and polysorbate 20 | Glycine | Acetate | 3.8 | 4.64 | 150.3 | 7.64 |
| 4. E40/48GT | glutamic acid, glycine, polysorbate 20 | Glycine | L-glutamic acid | 4 | 4.72 | 153.84 | 6.95 |
| 5. E52GT | glutamic acid, glycine, polysorbate 20 | Glycine | L-glutamic acid | 4.2 | 4.85 | 147.99 | 6.51 |
| 6. E48PT | glutamic acid, proline, and polysorbate 20 | Proline | L-glutamic acid | 3.8 | 4.55 | 147.3 | 5.99 |
| 7. E52PT | glutamic acid, proline, and polysorbate 20 | Proline | L-glutamic acid | 4.2 | 4.93 | 147.88 | 6.69 |
| 8. E48ST | glutamic acid, sorbitol, and polysorbate 20 | Sorbitol | L-glutamic acid | 3.8 | 4.79 | 148.7 | 7.55 |
| 9. E44SuT | glutamic acid, sucrose, and polysorbate 20 | Sucrose | L-glutamic acid | 3.2 | 4.66 | 148.55 | 7.61 |
| 10. E48SuT | glutamic acid, sucrose, and polysorbate 20 | Sucrose | L-glutamic acid | 3.8 | 4.85 | 147.36 | 8.42 |

TABLE 1.1-continued

Effect of pH on viscosity for highly concentrated AM-14 formulations

| Formulation | Formulation components | Excipient | Buffer | Buffer pH | Final pH | AM-14 Concentration (mg/mL) | Viscosity (cP) |
|---|---|---|---|---|---|---|---|
| 11. A48PT | acetic acid, proline, and polysorbate 20 | Proline | Acetate | | 4.8 | 153.57 | 6.89 |

A separate study was performed to investigate the relationship between viscosity and varying concentrations of AM-14 in the A52S formulation (10 mM sodium acetate, pH 5.2, 5% sorbitol). Table 1.3 shows AM-14 was formulated at concentrations ranging from approximately 48 mg/ml to approximately 163 mg/ml. The effect on viscosity is depicted in FIG. 3.

TABLE 1.3

Figure 3:
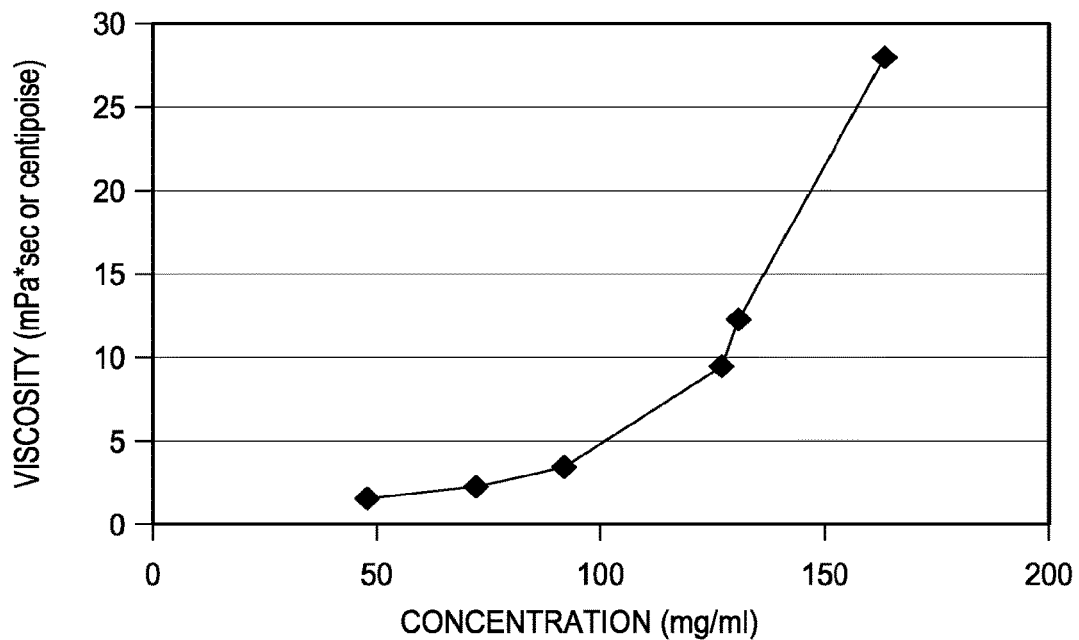
FIG. 3: A graph depicting the viscosity of AM-14 at different protein concentrations.

Viscosity of AM-14 at different concentrations (see FIG. 3)

| AM-14 A52S Concentration (mg/ml) | Density | mPa*s |
|---|---|---|
| 47.725 | 1.027807 | 1.5842 |
| 72.086 | 1.034805 | 2.2012 |
| 91.429 | 1.042012 | 3.4675 |
| 127.04 | 1.052502 | 9.3879 |
| 130.37 | 1.054458 | 12.1759 |
| 163.22 | 1.061677 | 27.9541 |

Figure 4:
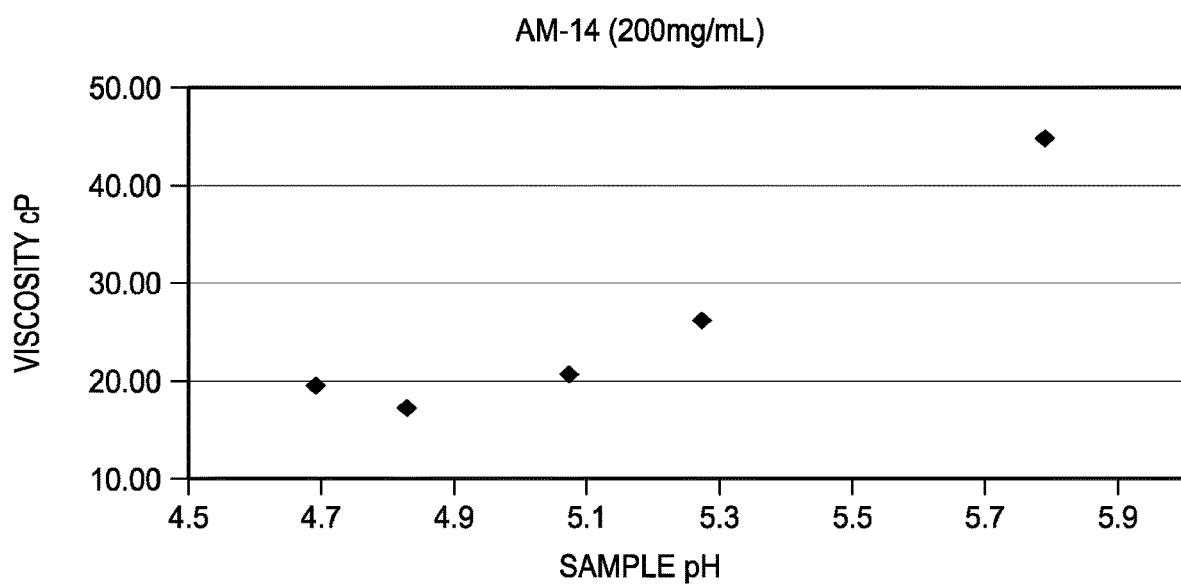
FIG. 4: A graph showing the relationship between the viscosity of an AM-14 formulation at 200 mg/ml as a function of varying pH.

In a separate study, the effect of pH on a highly concentrated formulation of AM-14 was conducted. AM-14 concentrations were approximately 200 mg/mL. The samples were prepared similarly using lyophilization process. The starting material was 70 mg/mL AM-14 in a buffer of 10 mM glutamate, pH 4.8 and 1% sucrose. The 1.5 mL of starting material was filled in 3 cc vials and then lyophilized. Each vial contained approximately 100 mg of AM-14. A series of solutions of 30 mM glutamate and 30 mM histidine at pH 3.0, 3.5, 4.0, 4.5, 5.0, 5.5, 6.0 and 6.5 were prepared. 0.5 mL of these buffers was added to the lyophilized vials to generate the material for viscosity measurement, which was about 200 mg/mL with different pH values. The effect of pH on the viscosity of AM-14 was determined and shown in FIG. 4, which depicts a subset of this data. This data demonstrates that the viscosity measured at 25° C. at higher pH, such as pH higher than 5.7 (viscosity is >40 cP) has a much higher viscosity than that seen at lower pH formulations (viscosity is greater or equal to 20 cP).

Stability studies for AM-14 were performed using either a 3 cc glass vial or a 1 mL pre-filled glass syringe. Samples were stored at 4, 25, 29, 37, 40, and 45 degrees C. Standard stability indicating assays were used to monitor the stability of the AM-14 formulations including SE-HPLC, CEX-HPLC, HIAC (sub-visible particle) and visual inspection.

1.4

4° C. stability (SE-HPLC assay), in pre-filled syringe

| | Sample | time 0 | 1 month | 3 month | Decrease in SEC % MP |
|---|---|---|---|---|---|
| 1 | A48SuT | 99.65 | 99.66 | 99.63 | 0.02 |
| 2 | E44GT | 45.63 | 40.96 | 41.65 | 3.98 |
| 3 | A48GT | 99.7 | 99.67 | 99.67 | 0.03 |
| 4 | E4048GT | 99.76 | 99.72 | 99.68 | 0.08 |
| 5 | E52GT | 99.7 | 99.7 | 99.68 | 0.02 |
| 6 | E48PT | 99.75 | 99.73 | 99.7 | 0.05 |
| 7 | E52PT | 99.71 | 99.71 | 99.7 | 0.01 |
| 8 | E48ST | 99.67 | 99.69 | 99.46 | 0.21 |
| 9 | E44SuT | 99.73 | 99.69 | 99.72 | 0.01 |
| 10 | E48SuT | 99.57 | 99.61 | 99.62 | −0.05 |

TABLE 1.5

25° C. stability; in pre-filled syringe

| | Sample | 0 | 1 m | 3 m | Decrease in SE % MP |
|---|---|---|---|---|---|
| 1 | A48SuT | 99.65 | 99.44 | 99.23 | 0.42 |
| 2 | E44GT | 45.63 | 2.6 | 1.76 | 43.87 |
| 3 | A48GT | 99.7 | 99.5 | 99.09 | 0.61 |
| 4 | E4048GT | 99.76 | 99.53 | 99.13 | 0.63 |
| 5 | E52GT | 99.7 | 99.58 | 99.23 | 0.47 |
| 6 | E48PT | 99.75 | 99.64 | 99.42 | 0.33 |
| 7 | E52PT | 99.71 | 99.63 | 99.45 | 0.26 |
| 8 | E48ST | 99.67 | 99.56 | 99.33 | 0.34 |
| 9 | E44SuT | 99.73 | 99.56 | 99.33 | 0.4 |
| 10 | E48SuT | 99.57 | 99.44 | 99.15 | 0.42 |

TABLE 1.6

Freeze-thaw stability from scale down study (1L scale) with control rate freezer

| Formulation | Excipient | buffer | Intial pH | final pH | Protein conc | Viscosity (25C) | T = 0 | After 2 freeze thaw |
|---|---|---|---|---|---|---|---|---|
| 110 mg/ml AM-14 formulated with 10 mM glutamate, 8.5% sucrose and 0.01% polysorbate 20 | Sucrose | L-glutamic acid | 3.8 | 4.8 | 110 | 3.56 | 99.77 | 99.79 |

TABLE 1.6-continued

Freeze-thaw stability from scale down study (1L scale) with control rate freezer

| Formulation | Excipient | buffer | Intial pH | final pH | Protein conc | Viscosity (25C) | T = 0 | After 2 freeze thaw |
|---|---|---|---|---|---|---|---|---|
| 150 mg/ml AM-14 formulated with 10 mM glutamate, 8.0% sucrose and 0.01% polysorbate 20 | Sucrose | L-glutamic acid | 3.8 | 4.8 | 140 | 6.7 | 99.73 | 99.71 |
| 150 mg/ml AM-14 formulated with 10 mM glutamate, 3% proline and 0.01% polysorbate 20 | Proline | L-glutamic acid | 4 | 4.8 | 140 | 4.74 | 99.73 | 99.7 |

Based on this data, embodiments of AM-14 formulations include: 100-150 mg/mL AM-14, formulated with 5-15 mM glutamic acid, 7-9% (w/v) sucrose, 0.003-0.02% (w/v) polysorbate 20, pH 4.5-5.5±0.2; such as 140 mg/mL AM-14, formulated with 10 mM glutamic acid, 8% (w/v) sucrose, 0.01% (w/v) polysorbate 20, pH 4.8±0.2; 100-150 mg/mL AM-14, formulated with 5-15 mM glutamic acid, 1-3% (w/v) glycine, 0.003-0.02% (w/v) polysorbate 20, pH 4.5-5.5±0.2, such as 140 mg/mL AM-14, formulated with 10 mM glutamic acid, 2% (w/v) glycine, 0.01% (w/v) polysorbate 20, pH 4.8±0.2; 100-150 mg/mL AM-14, formulated with 5-15 mM glutamic acid, 2-4% (w/v) proline, 0.003-0.02% (w/v) polysorbate 20, pH 4.5-5.5±0.2, such as about 140 mg/mL AM-14, formulated with 10 mM glutamic acid, 3% (w/v) L-proline, 0.01% (w/v) polysorbate 20, pH 4.8±0.2, and 140 mg/mL AM-14, formulated with 10 mM glutamic acid, 3% (w/v) L-proline, 0.01% (w/v) polysorbate 20, pH 4.8±0.2; 100-150 mg/mL AM-14, formulated with 5-15 mM acetic acid, 1-3% (w/v) glycine, 0.003-0.02% (w/v) polysorbate 20, pH 4.5-5.5±0.2, such as 140 mg/mL AM-14, formulated with 10 mM acetic acid, 2% (w/v) glycine, 0.01% (w/v) polysorbate 20, pH 4.8±0.2; 100-150 mg/mL AM-14, formulated with 5-15 mM acetic acid, 2-4% (w/v) proline, 0.003-0.02% (w/v) polysorbate 20, pH 4.5-5.5±0.2, such as 140 mg/mL AM-14, formulated with 10 mM acetic acid, 3% (w/v) L-proline, 0.01% (w/v) polysorbate 20, pH 4.8±0.2; 100-150 mg/mL AM-14, formulated with 5-15 mM acetic acid, 7-9% (w/v) sucrose, 0.003-0.02% (w/v) polysorbate 20, pH 4.5-5.5±0.2, such as 140 mg/mL AM-14, formulated with 10 mM acetic acid, 8% (w/v) sucrose, 0.01% (w/v) polysorbate 20, pH 4.8±0.2; 100-150 mg/mL AM-14, formulated with 5-15 mM acetic acid, 2-4% (w/v) glycerol, 0.003-0.02% (w/v) polysorbate 20, pH 4.5-5.5±0.2, such as 140 mg/mL AM-14, formulated with 10 mM acetic acid, 3% (w/v) glycerol, 0.01% (w/v) polysorbate 20, pH 4.8±0.2; 100-150 mg/mL AM-14, formulated with 5-15 mM acetic acid, 3.5-5.5% (w/v) sorbitol, 0.003-0.02% (w/v) polysorbate 20, pH 4.5-5.5±0.2, such as 140 mg/mL AM-14, formulated with 10 mM acetic acid, 4.5% (w/v) sorbitol, 0.01% (w/v) polysorbate 20, pH 4.8±0.2; 100-150 mg/mL AM-14, formulated with 5-15 mM glutamic acid, 7-9% (w/v) sucrose, 0.003-0.02% (w/v) polysorbate 20, pH 4.5-5.5±0.2, 4-10 cP at 25 degrees C., such as 140 mg/mL AM-14, formulated with 10 mM glutamic acid, 8% (w/v) sucrose, 0.01% (w/v) polysorbate 20, pH 4.8±0.2, 5-7 cP at 25 degrees C.; 100-150 mg/mL AM-14, formulated with 5-15 mM glutamic acid, 1-3% (w/v) glycine, 0.003-0.02% (w/v) polysorbate 20, pH 4.5-5.5±0.2, 4-10 cP at 25 degrees C., such as 140 mg/mL AM-14, formulated with 10 mM glutamic acid, 2% (w/v) glycine, 0.01% (w/v) polysorbate 20, pH 4.8±0.2, 5-7 cP at 25 degrees C.; 100-150 mg/mL AM-14, formulated with 5-15 mM glutamic acid, 2-4% (w/v) proline, 0.003-0.02% (w/v) polysorbate 20, pH 4.5-5.5±0.2, 4-10 cP at 25 degrees C., such as 140 mg/mL AM-14, formulated with 10 mM glutamic acid, 3% (w/v) L-proline, 0.01% (w/v) polysorbate 20, pH 4.8±0.2, 5-7 cP at 25 degrees C.; 100-150 mg/mL AM-14, formulated with 5-15 mM acetic acid, 1-3% (w/v) glycine, 0.003-0.02% (w/v) polysorbate 20, pH 4.5-5.5±0.2, 4-10 cP at 25 degrees C., such as 140 mg/mL AM-14, formulated with 10 mM acetic acid, 2% (w/v) glycine, 0.01% (w/v) polysorbate 20, pH 4.8±0.2, 5-7 cP at 25 degrees C.; 100-150 mg/mL AM-14, formulated with 5-15 mM acetic acid, 2-4% (w/v) proline, 0.003-0.02% (w/v) polysorbate 20, pH 4.5-5.5±0.2, 4-10 cP at 25 degrees C., such as 140 mg/mL AM-14, formulated with 10 mM acetic acid, 3% (w/v) L-proline, 0.01% (w/v) polysorbate 20, pH 4.8±0.2, 5-7 cP at 25 degrees C.; 100-150 mg/mL AM-14, formulated with 5-15 mM acetic acid, 7-9% (w/v) sucrose, 0.003-0.02% (w/v) polysorbate 20, pH 4.5-5.5±0.2, 4-10 cP at 25 degrees C., such as 140 mg/mL AM-14, formulated with 10 mM acetic acid, 8% (w/v) sucrose, 0.01% (w/v) polysorbate 20, pH 4.8±0.2, 5-7 cP at 25 degrees C.; 100-150 mg/mL AM-14, formulated with 5-15 mM acetic acid, 2-4% (w/v) glycerol, 0.003-0.02% (w/v) polysorbate 20, pH 4.5-5.5±0.2, 4-10 cP at 25 degrees C., such as 140 mg/mL AM-14, formulated with 10 mM acetic acid, 3% (w/v) glycerol, 0.01% (w/v) polysorbate 20, pH 4.8±0.2, 5-7 cP at 25 degrees C.; 100-150 mg/mL AM-14, formulated with 5-15 mM acetic acid, 3.5-5.5% (w/v) sorbitol, 0.003-0.02% (w/v) polysorbate 20, pH 4.5-5.5±0.2, 4-10 cP at 25 degrees C., such as 140 mg/mL AM-14, formulated with 10 mM acetic acid, 4.5% (w/v) sorbitol, 0.01% (w/v) polysorbate 20, pH 4.8±0.2, 5-7 cP at 25 degrees C.

Example 2

Dosages and Treatment Regimens for Treating Inflammatory Diseases in Humans with Anti-IL-17 Receptor "A" Monoclonal Antibodies Pre-Clinical Pharmacokinetics and Drug Metabolism Studies Pharmacokinetic studies included an one-month and a three-month toxicology studies. AM-14 was quantified in cynomolgus monkey serum using a validated enzyme-linked immunosorbent assay (ELISA). Briefly, microplate wells were coated with a mouse anti-AM-14 monoclonal antibody. Standards and quality controls were prepared by spiking AM-14 into a 100% cynomolgus monkey serum pool. The AM-14 in the standards, quality controls, and study samples was captured by immobilized mouse anti-AM-14 monoclonal antibody and then a second mouse anti-AM-14 monoclonal antibody conjugated to horseradish peroxidase (HRP) was added to bind the captured AM-14. A tetramethylbenzidine (TMB) substrate solution reacted with peroxide, and in the presence of HRP, created a colorimetric signal that was proportional to the amount of AM-14 bound by the capture antibody. The optical density was measured at 450 nm minus 650 nm. Data were reduced using a Logistic (auto-estimate) regression model with a weighting factor of $1/Y^2$. The nominal dynamic range of the assay for the 3 studies was 50 to 2500 ng/mL.

Single-Dose Pharmacokinetic Study

The pharmacokinetics of a single-dose pharmacokinetic study of AM-14 given to male cynomolgus monkeys following IV (intravenous) or SC (sub-cutaneous) administration objective was performed. 15 male cynomolgus monkeys were randomly assigned to 5 groups (n=3 per group) and received a 0.5 or 50 mg/kg IV dose of AM-14 or a 0.5, 5, or 50 mg/kg SC dose of AM-14.

The compartmental analysis performed (Table 2.2) estimated a first order clearance component of elimination of 1.78 mL/hr, a maximum elimination rate ($V_{max}$) of 34.4 ug/hr, and a $K_m$ of 0.984 ug/mL. When the doses of AM-14 led to serum concentrations below 0.1 ug/mL (approximately 0.1-fold the $K_m$ value), the saturable elimination pathway was totally free and the kinetics could be considered linear. Similarly, when the dose of AM-14 led to serum concentrations above 10 ug/mL (approximately 10-fold the $K_m$ value) during at least 3 to 4 half-lives, the saturable elimination component was negligible and the kinetics could also be considered linear. However, when the dose of AM-14 led to serum concentrations between 0.1 and 10 ug/mL, the non-linear component became relevant and the elimination kinetics varied depending on the dose and dose frequency; this translated into different effective half-life values.

AM-14 exhibited nonlinear pharmacokinetics after single dose IV or SC administration in cynomolgus monkeys that was consistent with target-mediated disposition, and was most pronounced following single SC administration up to 5 mg/kg. After single or multiple SC doses ranging from 5 to 350 mg/kg, the exposure increased approximately dose proportionally. No marked difference between sexes in AM-14 exposure and moderate accumulation were observed after multiple weekly dosing in cynomolgus monkeys for 1 or 3 months.

TABLE 2.1

Mean (SD) Noncompartmental Pharmacokinetic Parameter Estimates After Single-Dose Subcutaneous Administration of AM-14 to Cynomolgus Monkeys

| Dose (mg/kg) | $t_{max}$ (hr) | $C_0$ or $C_{max}$ (μg/mL) | $AUC_{0-t}$ (hr · μg/mL) | $AUC_{0-inf}$ (hr · μg/mL) | Cl or Cl/F (mL/hr) | $V_z$ or $V_z/F$ (mL) | $MRT_{0-inf}$ (hr) |
|---|---|---|---|---|---|---|---|
| (n = 3 per group) | | | | | | | |
| 0.5 IV | — | 9.79 (0.964) | 160 (44.2) | 168 (46) | 8.33 (2.64) | 142 (14.0) | 18 (3.5) |
| 0.5 SC | 27 | 1.28 (0.808) | 69.7 (43.4) | 74.2 (41) | 22.2 (11.2) | 681 (522) | 45 (9.5) |
| 5 SC | 72 | 20.7 (4.82) | 3110 (1160) | 3120 (1160) | 4.70 (1.61) | 98.7 (6.99) | 110 (8.1) |
| 50 IV | — | 673 (66.5) | 56600 (18100) | 57000 (18600) | 2.33 (0.592) | 75.2 (23.6) | 140 (47) |
| 50 SC | 72 | 166 (33.4) | 33700 (10400) | 33700 (10400) | 3.98 (1.18) | 72.2 (9.15) | 150 (28) |

Parameters are presented as average (standard deviation [SD]) to 3 significant figures, except for $t_{max}$ and $MRT_{0-inf}$
$t_{max}$ = time of $C_{max}$ after subcutaneous (SC) administration;
$C_{max}$ = maximum observed serum concentration;
$C_0$ = estimated initial concentration after intravenous (IV) bolus administration;
$AUC_{0-t}$ = area under the concentration-time curve from time 0 to the last quantifiable concentration;
$AUC_{0-inf}$ = AUC from time 0 to infinity;
CL or CL/F = clearance, calculated as Dose/$AUC_{(0-inf)}$;
$V_z$ or $V_z/F$ = apparent volume of distribution based on the terminal phase;
$MRT_{0-inf}$ = mean residence time from time 0 to infinity.

AM-14 serum concentration was shown to increase with increased dosing. After a single IV bolus, a 339-fold increase in $AUC_{0-inf}$ was observed for a 100-fold dose increase. After SC doses ranging from 0.5 to 5 mg/kg, AM-14 exposure (both $AUC_{0-inf}$ and $C_{max}$) increased greater than dose proportionally. However, after SC doses ranging from 5 to 50 mg/kg, the exposure increased approximately dose proportionally (Table 2.1).

Because the pharmacokinetic profile of AM-14 was non-linear, it was necessary to further analyze the data using a compartmental approach, and therefore, the data were fitted to a 2-compartment model with Michaelis-Menten elimination and an additional first order component of elimination.

TABLE 2.2

Compartmental Pharmacokinetic Parameter Estimates After Single-dose Subcutaneous Administration of AM-14 to Cynomolgus Monkeys

| Parameter | Description | Value (SE %) |
|---|---|---|
| $\theta_1$ | $F_{SC}$ bioavailability after SC administration | 0.977 (7.2) |
| $\theta_2$ (hr$^{-1}$) | $K_{aSC}$, Absorption rate constant for SC administration | 0.0267 (9.3) |
| $\theta_3$ (hr$^{-1}$) | $K_{12}$, Rate constant of distribution from central to peripheral | 0.0399 (20.6) |

TABLE 2.2-continued

Compartmental Pharmacokinetic Parameter Estimates
After Single-dose Subcutaneous Administration
of AM-14 to Cynomolgus Monkeys

| Parameter | Description | Value (SE %) |
|---|---|---|
| $\theta_4$ (hr$^{-1}$) | $K_{21}$, Rate constant of distribution from peripheral to central | 0.0889 (18.5) |
| $\theta_5$ (mL/hr) | CL, First order clearance | 1.78 (15.8) |
| $\theta_6$ (ug/mL) | $K_m$, Maximum rate of Elimination | 0.984 (23.6) |
| $\theta_7$ (ug/hr) | $V_m$, Michaelis-Menten constant | 34.4 (10.1) |
| $\theta_8$ (mL) | V, Volume of distribution | 224 (15.1) |
| $\sigma^2_1$ | Variance of proportional error | $0.25^2$ (13.4) |
| $\sigma^2_2$ | Variance of additive error | $99.1^2$ (27.5) |

SC = subcutaneous; SE = standard error

Clinical Effects of AM-14 in Humans

AM-14 was evaluated in two Phase 1 clinical studies. Study no. 1 was a randomized, double-blind, placebo-controlled, ascending single-dose study to evaluate the safety, tolerability, pharmacokinetics, and pharmacodynamics of AM-14 in healthy subjects and subjects with moderate to severe psoriasis. A single dose of AM-14 at 7, 21, 70, 140, 210, 350, or 420 mg SC or 21, 210, or 700 mg IV was administered, as shown in Table 2.3. This was a 2-part study in healthy subjects (Part A) and subjects with moderate to severe psoriasis (Part B). Healthy subjects were assigned to 1 of 8 sequential dosing cohorts and randomly assigned (3:1) within each cohort to receive a single SC or IV dose of AM-14 or placebo (Table 2.3). Subjects with moderate to severe psoriasis were assigned to 1 of 3 dosing cohorts and randomly assigned within each cohort to receive a single IV or SC dose of AM-14 or placebo.

AM-14 was formulated in 10 mM sodium acetate, 9% (w/v) sucrose, and 0.004% polysorbate 20, pH 5.2 at a final concentration of 70 mg/mL.

TABLE 2.3

Dose Escalation Sequence for Study No. 1 (healthy subjects and subjects with moderate to severe psoriasis)

| Part | Cohort | Dose/Route | No. on AM-14 | No. on Placebo | Subject Description |
|---|---|---|---|---|---|
| A | 1 | 7 mg SC | 6 | 2 | Healthy volunteer |
| A | 2 | 21 mg SC | 6 | 2 | Healthy volunteer |
| A | 3 | 21 mg IV | 3 | 1 | Healthy volunteer |
| A | 4 | 70 mg SC | 6 | 2 | Healthy volunteer |
| A | 5 | 210 mg SC | 6 | 2 | Healthy volunteer |
| A | 6 | 210 mg IV | 4[a] | 1 | Healthy volunteer |
| A | 7 | 420 mg SC | 6 | 2 | Healthy volunteer |
| A | 8 | 700 mg IV | 6 | 2 | Healthy volunteer |
| B | 9 | 700 mg IV | 8 | 2 | Moderate to severe psoriasis |
| B | 10 | 140 mg SC | 4 | 1 | Moderate to severe psoriasis |
| B | 11 | 350 mg SC | 8 | 2 | Moderate to severe psoriasis |

IV = intravenous; SC = subcutaneous
[a]The protocol specified 3 AM-14 subjects for this cohort; however, 4 AM-14 subjects were enrolled.

Study No. 2 is a Phase 1 b, randomized, double-blind, placebo-controlled, ascending multiple-dose study to evaluate the safety, tolerability, pharmacokinetics, pharmacodynamics and efficacy of AM-14 in subjects with rheumatoid arthritis. Approximately 110 subjects have received multiple SC or IV doses of AM-14 or matching placebo (Table 2.4). Subjects were randomized 3:1 in cohorts 1 to 3 and 5 and 6.

TABLE 2.4

Cohort and Dosing Schedule for Study No. 2 (rheumatoid arthritis)

| Cohort No. | Part | Dose & Route | No. of Active Subjects | No. of Placebo Subjects | Total No. of Subjects |
|---|---|---|---|---|---|
| 1 | A | 50 mg SC q2wks | 6 | 2 | 8 |
| 2 | A | 140 mg SC q2wks | 6 | 2 | 8 |
| 3 | A | 210 mg SC q2wks | 6 | 2 | 8 |
| 4 | B | Dose used in Part A | 35 | 35 | 70 |
| 5 | A | 420 mg IV on days 1 & 29 | 6 | 2 | 8 |
| 6 | A | 700 mg IV on days 1 & 29 | 6 | 2 | 8 |
| Total | | | 65 | 45 | 110 |

Pharmacodynamics of AM-14 in Humans

Two assays measuring pharmacodynamic responses to AM-14 were implemented in the clinical trials. A receptor occupancy assay allowed for assessment of target coverage and an ex vivo whole blood stimulation assay was used to evaluate functional IL-17R blockade.

Receptor Occupancy (RO) Assay

Single Dose in Healthy Subjects and Subjects with Psoriasis

Figure 5:
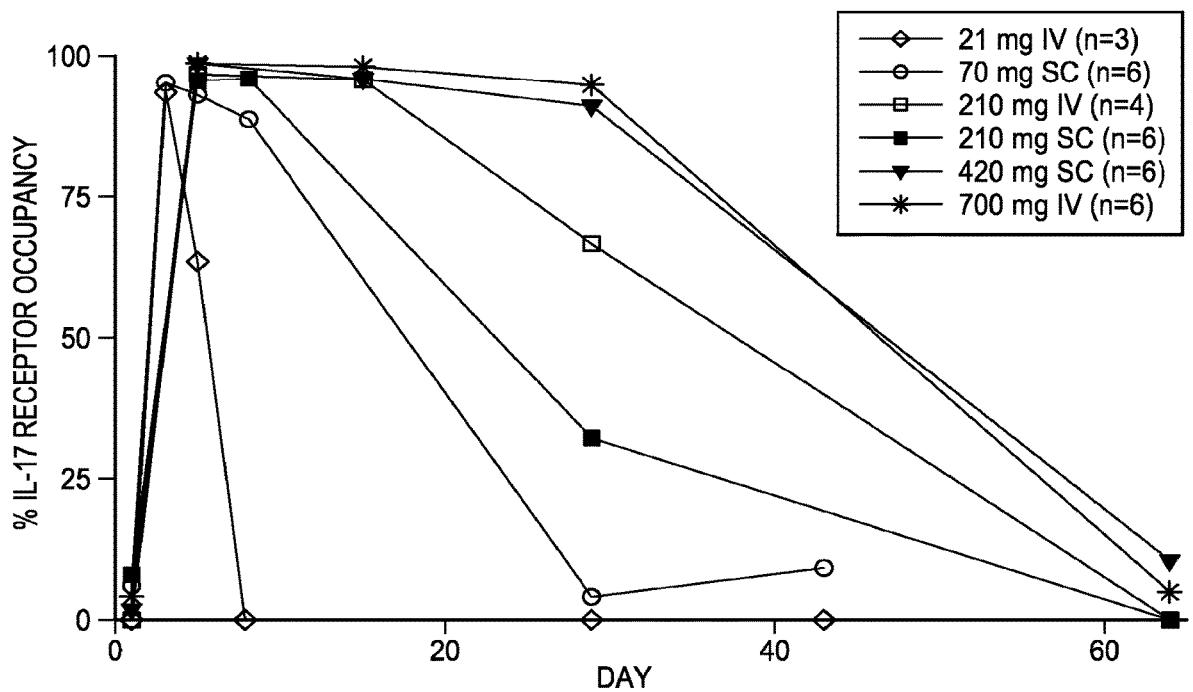
FIG. 5: A graph showing the mean percent IL-17 receptor occupancy as a function of time in healthy volunteers receiving AM-14 doses between 21 and 700 mg.

A semi-quantitative flow cytometric assay was developed to measure the expression of IL-17 receptor in subjects, allowing for estimates of biochemical coverage by AM-14 on lymphocytes, monocytes, and granulocytes, with each cell type easily identifiable by standard flow cytometry gating procedures known in the art. Blood specimens from subjects were collected on days −1, 1 (predose), 3, 5, 8 or 15, 29, 43, 64, and 85. The RO calculation was obtained using IL-17R coverage by AM-14 (with a competitive labeled antibody) in combination with total IL-17R expression (using a non-competitive IL-17R antibody). The results of the mean percent RO in healthy volunteers receiving AM-14 doses between 21 and 700 mg are summarized in FIG. 5 and FIG. 6, respectively. Mean values for AM-14 occupancy of the IL-17 receptor on granulocytes of healthy volunteers are shown These data demonstrate biochemical coverage of the IL-17 receptor on whole blood granulocytes at various times pre-dose (0) or post-dose of AM-14 administered either by the subcutaneous (—) or intravenous (----) route. Receptor occupancy was calculated from a baseline-normalized ratio AM-14-PE (competitive anti-IL17R mAb) to M204-PE (non-competitive anti-IL-17R mAb) multiplied by 100%. Technical variability in the assay at low levels of occupancy can generate values below zero, which are arbitrarily set to the x-axis. This includes datapoints from the 21 mg IV cohort (Days 1, 8, 29, and 43) and the 210 mg IV and SC groups (Day 64).

Figure 6:
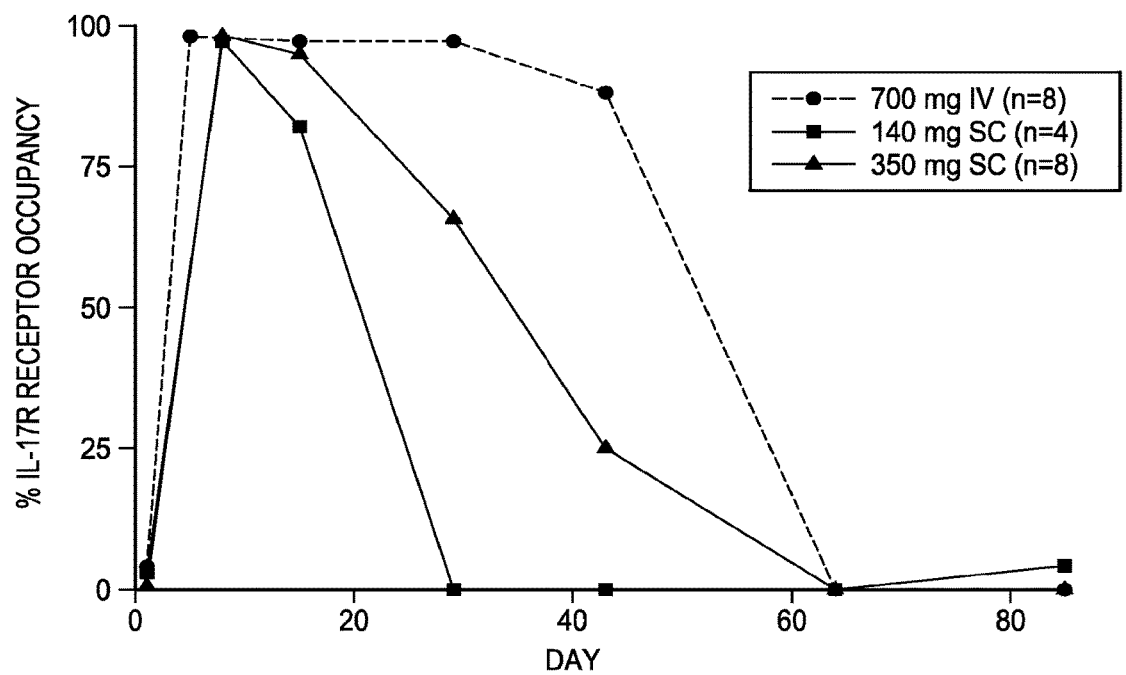
FIG. 6: A graph showing the mean percent IL-17 receptor occupancy as a function of time in psoriasis patients receiving AM-14 doses of 140, 210 and 700 mg.

The results of the mean percent RO in patients with psoriasis receiving AM-14 doses between 21 and 700 mg are summarized in FIG. 6. Mean values for AM-14 occupancy of the IL-17 receptor on granulocytes of patients with psoriasis are shown. These data demonstrate biochemical coverage of the IL-17 receptor on whole blood granulocytes at various times pre-dose (0) or post-dose. Receptor occupancy was calculated from a baseline-normalized ratio of AM-14-PE (competitive anti-IL17R mAb) to M204-PE (non-competitive anti-IL-17R mAb) multiplied by 100%. Technical variability in the assay at low levels of occupancy can generate values below zero, which are arbitrarily set to the x-axis. This includes 2 datapoints from the 140 mg SC cohort and 2 data points from the 350 mg SC cohort.

Maximal coverage was observed at the first sampling time in all subjects, at all dosage levels. Partial RO was observed at days 3 and 5 at the 7 and 21 mg SC dose levels. Greater than 90% mean RO was achieved for the 21 mg IV dose level and all cohorts treated with 70 mg AM-14 and higher. More prolonged RO was detectable as AM-14 dose levels escalated. Greater than 90% IL-17R RO was observed from 5 to 29 days post-treatment in individuals receiving 420 or 700 mg AM-14 in a single dose. This data shows that healthy volunteers and psoriasis patients exhibited similar RO profiles when administered equivalent doses of AM-14. There were no apparent changes in the percentage of monocytes, granulocytes, lymphocytes, or lymphocyte subsets, including T cells, B cells, and natural killer cells.

Multiple Doses in Subjects with RA

Figure 7:
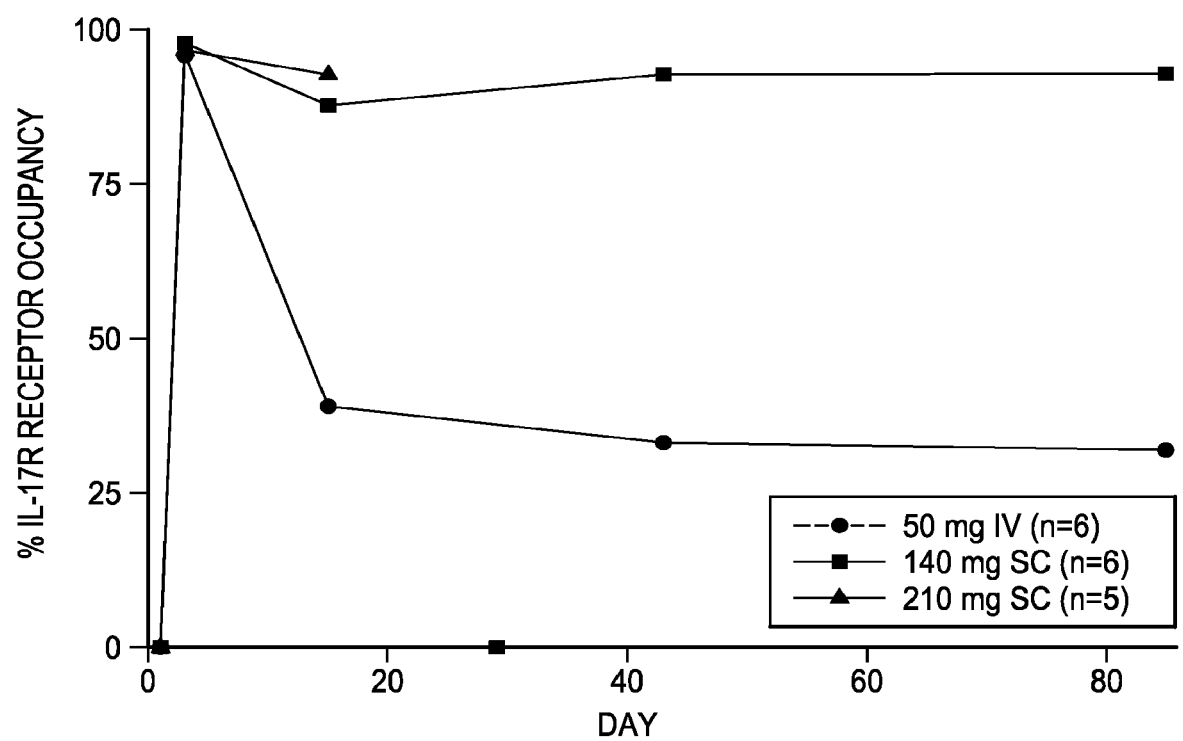
FIG. 7: A graph showing the mean percent IL-17 receptor occupancy as a function of time in rheumatoid arthritis receiving AM-14 doses between 50 and 210 mg.

Blood specimens from subjects were collected on days −1, 1 (predose), 3, 15, 43, and 85 and assayed using a semi-quantitative flow cytometric assay. Results of mean percent RO in rheumatoid arthritis (RA) patients receiving ascending doses of AM-14 are summarized in FIG. 7. Notably there were no differences between RA subjects and healthy volunteers in expression levels of IL-17R or AM-14 binding to leukocytes based on comparative in vitro studies in these populations. FIG. 7 shows the mean IL-17 receptor occupancy on granulocytes in RA patients pre-dose (0) or post-dose AM-14 treatment. Receptor occupancy was calculated from a baseline-normalized ratio AM-14-PE (competitive anti-IL17R mAb) to M204-PE (non-competitive anti-IL-17R mAb). Technical variability in the assay at low levels of occupancy can generate values below zero, which are arbitrarily set to the x-axis. This includes day −1 of the 50 and 140 mg cohorts and day 1 of the 210 mg cohort.

Maximal granulocyte RO by AM-14 was observed 3 days post-treatment at all dose levels. Patients enrolled in cohort 1 (50 mg) exhibited 95% RO at Day 3 and partial RO (32% to 39%) when drug reached trough levels on Days 15, 43, and 85. All patients in cohort 2 (140 mg) exhibited greater than 95% RO on Day 3, and greater than 80% RO on Day 15. At Day 43, RO was greater than 90% in all patients, suggesting some degree of accumulation of AM-14. Receptor occupancy remained above 90% in 5 of 6 patients at Day 85 and all patients exhibited greater than 80% RO. Data through Day 15 for cohort 3 (210 mg) showed that patients exhibited greater than 95% RO at Day 3. There were no apparent changes in the percentage of monocytes, granulocytes, lymphocytes, or lymphocyte subsets including T cells, B cells, and natural killer cells in any cohort of RA patients treated with AM-14.

Whole Blood Stimulation Assay

Assessment of Biological Effects of AM-14 Using an Ex Vivo Whole Blood Stimulation Assay To demonstrate a functional biological effect of AM-14 on IL-17R signaling, a pharmacodynamic assay using human whole blood was developed and incorporated into Study no. 1. In this assay, human whole blood was collected pre- and post-dosing with AM-14 and then stimulated with TNF and a dose-titration of IL-17 for 4 hours. The cells were then lysed and the lysate was subsequently analyzed for IL-17 responsive genes, including IL-6, using a branched DNA (bDNA) signal amplification assay. In the presence of AM-14, the induction of IL-6 mRNA is competitively inhibited, with an observed increase in EC50 for IL-17 dependent increases in expression. These data can be expressed quantitatively as a shift in the EC50 response to IL-17 relative to the predose baseline for each patient.

The EC50 curves for IL-17 stimulation of IL-6 mRNA (as measured by the bDNA assay) were significantly shifted compared with predose after a single dose of AM-14. Some level of functional signaling blockade was noted in all AM-14-treated healthy subjects from cohort 4 (70 mg SC) on day 5, and all AM-14-treated healthy subjects in cohorts 5 (210 mg SC) to cohort 8 (700 mg IV) on day 15. In cohort 9 (700 mg IV), all 4 tested AM-14-treated psoriasis subjects showed functional blockade at day 29, and 3 of 4 subjects showed blockade at day 43. The average log 10 EC50 shift for each cohort at the tested time points is shown in Table 2.5.

TABLE 2-5

AM-14 Leads to Functional Blockade of IL-17 Signaling in an Ex Vivo Assay

| Cohort | Dose | 30 min[a] | Day 5[a] | Day 8[a] | Day 15[a] | Day 29[a] | Day 43[a] | Day 64[a] |
|---|---|---|---|---|---|---|---|---|
| 1 | 7 mg SC | | −0.04 | −0.27 | | | −0.24 | |
| 2 | 21 mg SC | | 0.22 | 0.22 | | | 0.35 | |
| 3 | 21 mg IV | 2.08 | | | 0.4 | | 0.19 | |
| 4 | 70 mg SC | | 1.32 | 0.91 | | | −0.04 | |
| 5 | 210 mg SC | | 2.35 | | 1.22 | | | −0.13 |
| 6 | 210 mg IV | 2.49 | | | 2.09 | | | −0.24 |
| 7 | 420 mg SC | | 2.1 | | 2.12 | | | 0.15 |
| 8 | 700 mg IV | 1.72 | | | 1.74 | | | −0.99 |
| 9 | 700 mg IV | | | | | 1.95 | 1.46 | |
| 10 | 140 mg SC | | | | | 0.45 | 0.27 | |
| 11 | 350 mg SC | | | | | 2.02 | 0.45 | |
| | Placebo[b] | 0.03 | −0.08 | 0.19 | 0 | 0.04 | 0.27 | 0.05 |

[a]The log EC50 shift was calculated from the postdose sample minus the average log EC50 of 2 predose samples per subject. The mean log EC50 shift is reported for the 3 to 6 tested subjects in each cohort
[b]The mean value of placebo samples across all cohorts collected at that same time point postdose Competitive Antagonism Model for Whole Blood Stimulation Data Preliminary pharmacokinetic/pharmacodynamic analyses using a competitive antagonist model enabled the modeling of the effects of AM-14 on IL-17R function based on the ex vivo whole blood stimulation (WBS) assay. The dissociation constant ($K_i$) was estimated to be 51 ng/mL, and the AM-14 $IC_{50}$ and $IC_{90}$ levels of IL-17R inhibition were estimated to be within the ranges of approximately 130 to 540 and approximately 2860 to 15600 ng/mL, respectively, when IL-17 concentration is assumed to range from 0.5 to 50 ng/mL.

Pharmacokinetics of AM-14 in Humans

Serum Pharmacokinetics in Single Dose in Healthy Subjects and Subjects with Psoriasis Single-dose IV and SC AM-14 pharmacokinetic data were obtained for the healthy subjects in cohorts 1 to 8 and the psoriasis subjects in cohorts 9 to 11. AM-14 serum concentrations were not detectable in any sample from cohort 1 (7 mg SC) or in the majority of samples from cohort 2 (21 mg SC). The AM-14 serum concentration vs time profiles from all other healthy volunteer cohorts exhibited nonlinear pharmacokinetics and the exposure (as assessed by the maximum observed concentration [$C_{max}$] and the area under the concentration-time curve from time 0 to the last quantifiable concentration [$AUC_{0-t}$]) increased greater than dose proportionally (Table 2.6). After 70, 210, or 420 mg SC administration, the median time to $C_{max}$ ($t_{max}$) ranged from 48 to 168 hours. The apparent bioavailability after SC administration was estimated to be approximately 70% based on simultaneous pharmacokinetic modeling of all SC and IV cohort data. Pharmacokinetic parameters for 700 mg IV dosing in psoriasis subjects appeared to be comparable to those in healthy volunteers based on direct comparison of 700 mg IV concentration-time curves in healthy volunteer and psoriasis subjects (cohort 8 and cohort 9). Two separate biomarker assays were implemented to determine the biological activity of AM-14 in whole blood, including receptor occupancy and functional blockade of the IL-17 receptor, as described above. Both assays demonstrated a direct relationship between the serum concentrations of AM-14 and the functional readouts of these assays, including target (IL-17R) coverage and log EC50 shift measured by the whole blood stimulation assay. Samples with measurable circulating AM-14 consistently showed IL-17 receptor occupancy and an increase in log EC50, with higher shifts at higher concentrations.

TABLE 2.6

Mean (SD) Pharmacokinetic Parameters of AM-14 in Healthy Volunteers (Cohorts 1 to 8) and Psoriasis Subjects (Cohorts 9 to 11)

| Cohort | Dose and route (mg) | $T_{max}$ (hr) | $C_{max}$ (ug/mL) | $AUC_{0-t}$ (ug · hr/mL) |
|---|---|---|---|---|
| 1 (HV) | 7 SC | NC | NC | NC |
| 2 (HV) | 21 SC | NC | NC | NC |
| 3 (HV) | 21 IV | 0.6 | 6.67 | 238 |
|  |  | (0.6-4.0) | (2.11) | (78.9) |
| 4 (HV) | 70 SC | 48 | 2.54 | 313 |
|  |  | (48-96) | (1.37) | (213) |
| 5 (HV) | 210 SC | 96 | 10.6 | 2790 |
|  |  | (72-96) | (8.93) | (2740) |
| 6 (HV) | 210 IV | 0.7 | 63.9 | 8280 |
|  |  | (0.6-0.7) | (12.6) | (1440) |
| 7 (HV) | 420 SC | 168 | 23.6 | 9360 |
|  |  | (96-168) | (5.37) | (2550) |
| 8 (HV) | 700 IV | 0.7 | 159 | 36000 |
|  |  | (0.7-0.8) | (29.5) | (8850) |
| 9 (PsO) | 700 IV | 2.0 | 198 | 39800 |
|  |  | (0.5-4.0) | (39.6) | (8610) |
| 10 (PsO) | 140 SC | 48 | 5.47 | 631 |
|  |  | (48-48) | (3.00) | (347) |
| 11[a] (PsO) | 350 SC | 168 | 11.5 | 3030 |
|  |  | (48-168) | (5.72) | (1980). |

[a]Only partial data available for cohort 11
$C_{max}$ and $AUC_{0-t}$ were reported as mean (SD) values while $t_{max}$ was reported as median (range).
All values were rounded to 3 significant figures after calculations were performed, except $t_{max}$.
$AUC_{0-t}$ = area under the concentration-time curve from time 0 to the last quantifiable concentration; $C_{max}$ = maximum observed concentration; $t_{max}$ = time at observed maximum concentration; NC = not calculated due to most samples below limit of quantitation; HV = healthy volunteer; PsO = psoriasis subject.

Serum Pharmacokinetics in Multiple Doses in Subjects with RA

Preliminary multi-dose SC AM-14 pharmacokinetic data were obtained from RA subjects in the phase 1 b study. AM-14 serum concentration data were available through the end of study for all cohort 1 subjects (50 mg every 2 weeks) and up to day 85 for majority of the cohort 2 subjects (140 mg every 2 weeks). AM-14 exhibited nonlinear pharmacokinetics in RA subjects and the exposure (as assessed by $C_{max}$ and $AUC_{0-t}$) after the first and the last ($6^{th}$) SC dose increased greater than dose proportionally from the 50 to 140 mg dose (Table 2.7). The median $t_{max}$ ranged from 36 to 96 hours. Minimal accumulation was observed after 6 doses of 50 mg SC administered every 2 weeks, whereas the accumulation was minimal after 140 mg administered every 2 weeks. Pharmacokinetics of AM-14 after the first SC dose of 140 mg in RA subjects appeared to be comparable to those after single 140 mg SC dosing in psoriasis subjects (cohort 10; $C_{max}$=5.47±3.00 µg/mL, $AUC_{0-t}$=631±347 µg·hr/mL).

TABLE 2.7

Mean (SD) Pharmacokinetic Parameters of AM-14 in RA Subjects (Cohorts 1 and 2)

| Cohort | Dose and route (mg) | Phase | $T_{max}$ (hr) | $C_{max}$ (µg/mL) | $AUC_{0-t}$ (µg · hr/mL) |
|---|---|---|---|---|---|
| 1 | 50 SC q2w | $1^{st}$ dose | 36.0 | 0.742 | 41.6 |
|  |  |  | (4.0-48.0) | (0.522) | (38.6) |
|  |  | $6^{th}$ dose | 48.0 | 1.35 | 95.9 |
|  |  |  | (24.0-48.0) | (1.07) | (73.7) |
| 2 | 140 SC q2w | $1^{st}$ dose | 96.0 | 5.67 | 864 |
|  |  |  | (48.0-96.0) | (2.98) | (668) |
|  |  | $6^{th}$ dose[a] | 96.0 | 5.93 | 1200 |
|  |  |  | (48.0-96.0) | (5.15) | (1240) |

$C_{max}$ and $AUC_{0-t}$ were reported as mean (SD) values while $t_{max}$ was reported as median (range).
All values were rounded to 3 significant figures after calculations were performed, except $t_{max}$ which was presented to one decimal figure
$AUC_{0-t}$ = area under the concentration-time curve from time 0 to the last quantifiable concentration; $C_{max}$ = maximum observed concentration; q2w = every 2 weeks; $t_{max}$ = time at observed maximum concentration
[a]Only partial data available for the last dose of cohort 2.

Psoriasis Study Results

Fifty-seven healthy subjects were enrolled into cohorts 1 to 8; 43 subjects received AM-14 and 14 subjects received placebo. Twenty-five subjects with moderate to severe psoriasis were enrolled into cohorts 9 to 11. In cohort 9, 8 subjects received AM-14 and 2 subjects received placebo; in cohort 10, 4 subjects received AM-14 and 1 subject received placebo, and in cohort 11, 8 subjects received AM-14 and 2 subjects received placebo.

PASI scores for all psoriasis subjects (A-J) in cohort 9 through day 85 (end of study) are presented in Table 2.8. PASI scores for all psoriasis subjects (A-E) in cohort 10 cantly ($\alpha=0.05$) higher in the 350 mg SC group compared with placebo on Days 15 and 43; similar results were observed for the 140 mg SC group on Day 15 ($\alpha=0.05$).

TABLE 2.8

PASI Responses for Cohort 9

| Cohort 9 PASI score | A | B | C-PBO | D | E | F | G | H-PBO | I | J |
|---|---|---|---|---|---|---|---|---|---|---|
| Pre dose | 17.4 | 15.2 | 26.2 | 11.6 | 11.0 | 16.0 | 12.6 | 11.8 | 12.5 | 12.1 |
| Day 15 | 6.6 | 6.1 | 17.8 | 5.2 | 6.4 | 7.8 | 5.0 | 8.4 | 2.7 | 2.9 |
| Day 29 | 4.9 | 2.8 | 17.0 | 4.1 | 5.2 | 4.8 | 2.4 | 9.5 | 2.1 | 0.4 |
| Day 43 | 4.1 | 0.9 | 19.5 | 1.3 | 2.4 | 4.5 | 1.0 | 8.8 | 2.8 | 0.0 |
| Day 64 | 7.0 | 4.5 | 21.2 | 2.2 | 1.8 | 9.5 | 2.4 | 11.4 | 2.8 | 0.0 |
| Day 85 | 7.6 | 5.1 | 18.0 | 3.7 | 4.7 | 14.3 | 8.2 | 12.9 | 10.8 | 0.0 |
| %PASI Reduction | A | B | C-PBO | D | E | F | G | H-PBO | I | J |
| Day 15 | 62% | 60% | 32% | 55% | 42% | 51% | 60% | 29% | 78% | 76% |
| Day 29 | 72% | 82% | 35% | 65% | 53% | 70% | 81% | 19% | 83% | 97% |
| Day 43 | 76% | 94% | 26% | 89% | 78% | 72% | 92% | 25% | 78% | 100% |
| Day 64 | 60% | 70% | 19% | 81% | 84% | 41% | 81% | 3% | 78% | 100% |
| Day 85 | 56% | 66% | 31% | 68% | 57% | 11% | 35% | -9% | 14% | 100% | through day 85 (end of study) are presented in Table 2.10. PASI scores for all psoriasis subjects (A-J) in cohort 11 through day 85 (end of study) are presented in Table 2.11.

In cohort 9 (700 mg IV) maximal PASI effects were observed at day 43, at which time a 75% reduction in PASI score (PASI 75) was observed in 7 of 8 (88%) subjects receiving AM-14 (Table 2.8). All subjects receiving AM-14 in cohort 9 reached a PASI 50 (50% reduction) by day 29, while no subjects receiving placebo attained a PASI 50 response at any time point. A PASI 90 response (90% reduction from baseline PASI score) was observed in 3 of 8 (38%) subjects by day 43 receiving 700 mg IV AM-14 (Tables 2.8 and 2.9). Compared to the high dose group of PsO subjects (700 mg IV), there were lower PASI responses for subjects receiving 140 mg and 350 mg of AM-14 given SC. As shown in Table 2.10, only 1 of 4 subjects had a significant PASI response (>50%) in the 140 mg SC dose group and this response was gone by day 43. In the 350 mg SC cohort, 6 of 8 and 5 of 8 subjects achieved PASI 50 and PASI 75, respectively, during the course of the study (Table 2.11).

There was a positive relationship between AM-14 dose and PASI 50/75/90 response among the AM-14-treated subjects. No subjects who received placebo achieved a PASI 50 response or greater at any postdose time point. The mean percent improvement in PASI score increased with increasing AM-14 dose through Day 29. The 700 mg IV and 350 mg SC groups had higher mean percent improvement in PASI scores than the placebo group at all postdose time points. A total of 7 of 8 (88%) and 5 of 8 (63%) subjects in the 700 mg IV and 350 mg SC groups, respectively, achieved a PASI 75 score or greater response. The 140 mg SC group had higher mean percent improvement in PASI scores than the placebo group up to Day 29, with 2 of 4 subjects (50%) achieving a PASI 50 response at any postdose time point.

The mean PGA improvement from baseline scores was higher in the 700 mg IV group compared with the placebo group at all time points; these differences were statistically significant ($\alpha=0.05$) at all time points based on post hoc analyses, an exception was the mean PGA improvement score on Day 85 (p=0.0510). Based on post hoc analyses, the mean PGA improvement scores from baseline were signifi-

TABLE 2.9

PASI Response for Cohort 9 - Percent Improvement over Time by Treatment Group

| PASI Response | Time Point | Placebo n/N (%) | AM-14 at 700 mg dose (IV) n/N (%) |
|---|---|---|---|
| ≥50% | Day 15 | 0/2(0) | 7/8(88) |
|  | Day 29 | 0/2(0) | 8/8(100) |
|  | Day 43 | 0/2(0) | 8/8(100) |
|  | Day 64 | 0/2(0) | 7/8(88) |
|  | Day 85 | 0/2(0) | 4/8(50) |
| ≥75% | Day 15 | 0/2(0) | 2/8(25) |
|  | Day 29 | 0/2(0) | 5/8(63) |
|  | Day 43 | 0/2(0) | 7/8(88) |
|  | Day 64 | 0/2(0) | 4/8(50) |
|  | Day 85 | 0/2(0) | 1/8(13) |
| ≥90% | Day 15 | 0/2(0) | 0/8(0) |
|  | Day 29 | 0/2(0) | 1/8(13) |
|  | Day 43 | 0/2(0) | 3/8(38) |
|  | Day 64 | 0/2(0) | 1/8(13) |
|  | Day 85 | 0/2(0) | 1/8(13) |

N = Number of subjects who received treatment and had an assessment at each visit
n = Number of responders at each visit

TABLE 2.10

PASI Responses for Cohort 10

|  | A | B | C | D | E-PBO |
|---|---|---|---|---|---|
| Cohort 10 PASI score |  |  |  |  |  |
| Pre dose | 12.6 | 15.4 | 10.5 | 11.0 | 16.8 |
| Day 15 | 12.0 | 11.6 | 5.2 | 8.1 | 17.2 |
| Day 29 | 11.6 | 5.4 | 6.6 | 9.9 | 16.2 |
| Day 43 | 12.1 | 9.8 | 8.1 | 9.8 | 14.8 |
| Day 64 | 15.6 | 13.6 | 8.9 | 10.1 | 15.9 |
| Day 85 | 12.5 | 15.6 | 8.9 | 9.6 | 16.5 |
| % PASI Reduction |  |  |  |  |  |
| Day 15 | 5% | 25% | 50% | 26% | -2% |
| Day 29 | 8% | 65% | 37% | 10% | 4% |
| Day 43 | 4% | 36% | 23% | 11% | 12% |
| Day 64 | -24% | 12% | 15% | 8% | 5% |
| Day 85 | 1% | -1% | 15% | 13% | 2% |

TABLE 2.11

| PASI Responses for Cohort 11 | | | | | | | | | | |
|---|---|---|---|---|---|---|---|---|---|---|
| Cohort 11 PASI score | A | B | C | D-PBO | E | F | G | H | I | J-PBO |
| Pre dose | 13.3 | 17.8 | 14.2 | 12.5 | 6.4 | 13.4 | 19.0 | 13.3 | 12.0 | 16.3 |
| Day 15 | 6.9 | 13.6 | 12.6 | 12.5 | 0.0 | 3.4 | 9.2 | 4.0 | 4.0 | 11.7 |
| Day 29 | 7.8 | 11.8 | 12.8 | 11.0 | 2.4 | 0.4 | 7.2 | 2.8 | 2.1 | 11.7 |
| Day 43 | 10.4 | 7.8 | 14.4 | 10.7 | 1.0 | 7.5 | 4.8 | 4.8 | 2.0 | 12.7 |
| Day 64 | 11.3 | 7.4 | 13.1 | 12.5 | 2.4 | 5.9 | 4.5 | 5.6 | 6.0 | 11.3 |
| Day 85 | 11.0 | 12.2 | 14.0 | 12.5 | 2.4 | 6.2 | 7.6 | 5.2 | 5.8 | 12.6 |
| %PASI Reduction | A | B | C | D-PBO | E | F | G | H-PBO | I | J-PBO |
| Day 15 | 48% | 24% | 11% | 0% | 100% | 75% | 52% | 70% | 67% | 28% |
| Day 29 | 41% | 34% | 10% | 12% | 63% | 97% | 62% | 79% | 83% | 28% |
| Day 43 | 22% | 56% | −1% | 14% | 84% | 44% | 75% | 64% | 83% | 22% |
| Day 64 | 15% | 58% | 8% | 0% | 63% | 56% | 76% | 58% | 50% | 31% |
| Day 85 | 17% | 31% | 1% | −2% | 63% | 54% | 60% | 61% | 52% | 23% |

Rheumatoid Arthritis Study Results

To date, all subjects in cohorts 1-3 (50 mg SC, 140 mg SC and 210 mg SC) have completed the study. All 24 subjects enrolled in cohorts 1-3 were receiving concomitant MTX (n=23) or leflunomide (n=1). To date all subjects in cohort 5 (420 mg IV) have completed dosing, and 6 of 8 subjects in cohort 6 (700 mg IV) have been enrolled. AM-14 has been well tolerated at the doses tested (50, 140, and 210 mg SC).

Pharmacokinetic/Pharmacodynamic Modeling

Compartmental pharmacokinetic modeling was conducted on AM-14 serum concentration time data from the healthy volunteers (cohorts 3 to 8). A two-compartment model with parallel linear and nonlinear elimination pathways and an added compartment for SC absorption was used to describe the AM-14 concentration-time data. The nonlinear elimination pathway was modeled via Michaelis-Menten kinetics, with resulting maximum elimination rate ($V_{max}$) and Michaelis-Menten constant ($K_m$) of 1290 μg/day/mL (4% SE) and 14.9 ng/mL (270% SE), respectively. The estimated human pharmacokinetic parameters were used to simulate pharmacokinetic concentration-time profiles and calculate exposures (AUC and $C_{max}$) across a range of single and multiple IV and SC doses for potential clinical study. The single-dose predictions compared well with subsequent available data from the psoriasis cohorts (cohorts 9 to 11). The multiple dose predictions also compared well with available data from cohorts 1 and 2 of the phase 1 b study, although with less accumulation of concentration than expected for the 140 mg every 2 weeks dosing. Additionally, the model also predicted well for AM-14 pharmacokinetics in RA subjects in the phase 1 b study, suggesting comparable pharmacokinetics of AM-14 among healthy and disease (both RA and psoriasis) populations.

Pharmacokinetic/Pharmacodynamic Relationships

Figure 8:
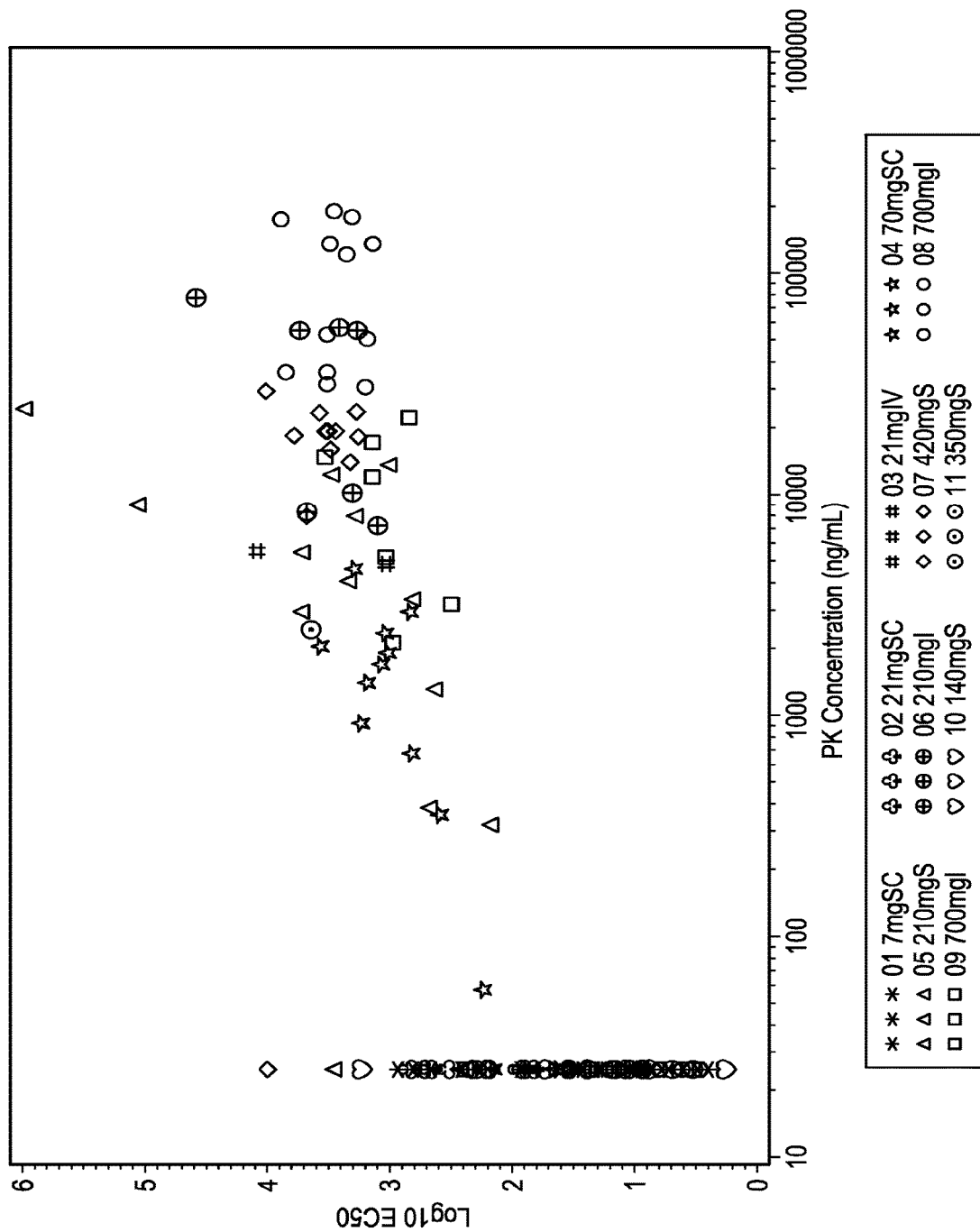
FIG. 8: A graph showing monotonically increasing relationship between the pEC50 shift measured by the whole blood stimulation assay and the concentration of circulating AM-14 measured by the pharmacokinetic assay. The concentration of AM-14 is on the x-axis and the pEC50 shift is on the y-axis.

There was a monotonically increasing relationship between the pEC50 shift measured by the whole blood stimulation assay and the concentration of circulating AM-14 measured by the pharmacokinetic assay, as shown in FIG. 8. The concentration of AM-14 is on the x-axis and the pEC50 shift is on the y-axis. The log EC50 shift is measured from the average of 2 baseline samples. The lower limit of quantitation (LLOQ) for the PK assay was 50 ng/mL, and therefore post-dose samples below the LLOQ are plotted at 25 ng/mL on the x-axis, and have log EC50 values predominantly below 2. The mean log EC50 shift for placebo samples is 0.02±0.6. Samples with measurable circulating AM-14 consistently show an increase in log EC50, with higher shifts at higher concentrations. Similar to placebo samples, the log EC50 shift with samples at low concentrations of AM-14, below the LLOQ of 50 ng/mL, is limited. The overall relationship fits a model of competitive inhibition between AM-14 and IL-17A.

Figure 9:
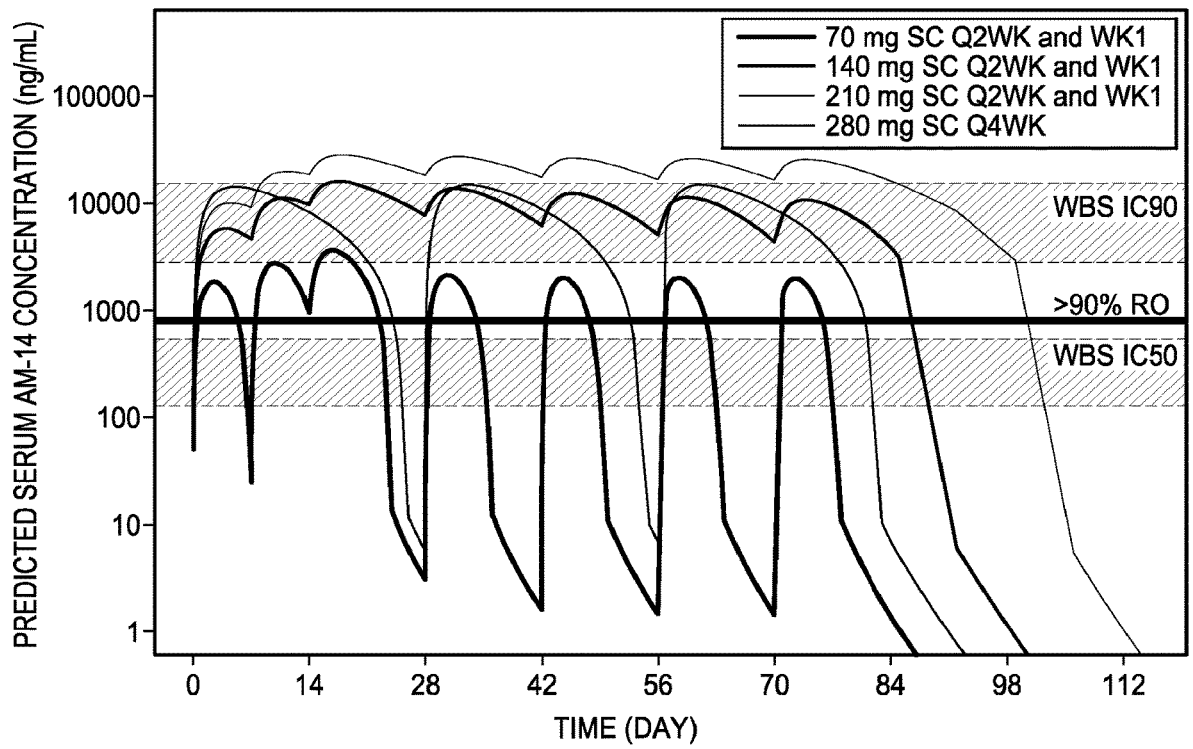
FIG. 9: A graphical depiction of the predicted mean AM-14 pharmacokinetic profiles based on modeling of the single dose study

AM-14 proposed doses and dosing regimens are depicted in FIG. 9 based on modeling described above. The $IC_{50}$ and $IC_{90}$ levels for AM-14 are based on data from the ex vivo whole blood stimulation assay, and uses a competitive antagonism PK/PD model over an IL-17 concentration range of 0.5 to 50 ng/mL. $IC_{50/90}$: AM-14 serum concentration that inhibits the increase of IL-6 mRNA level by 50/90% in the ex vivo whole blood assay. The 70 mg dose (with week 1 load) is projected to achieve significant exposure above the $IC_{50}$ level. The 140 and 210 mg doses administered every 2 weeks (with an additional dose at week 1) are expected to achieve sustained exposure within and above, respectively, the expected $IC_{90}$ range for the duration of the study period. The 280 mg dose administered every 4 weeks is also expected to achieve exposure within the expected $IC_{90}$ range, but with trough excursions below the $IC_{50}$ range.

The exposure margins were estimated as the ratio of exposure in cynomolgus monkeys post-dose on day 78 at 90 mg/kg SC to the predicted human exposure at steady state. The mean $AUC_{0-168\ hr}$ and $C_{max}$ after dosing on Day 78 in the monkey toxicokinetic study was 159,000 ug-hr/mL and 1180 ug/mL, respectively. The predicted steady state $AUC_{0-336\ hr}$ after the third dose of 70, 140, or 210 mg doses administered every 2 weeks (with week 1 load) were 552, 4320, and 8230 ug-hr/mL and the predicted steady state $AUC_{0-672\ hr}$ after the third and final dose of 280 mg administered every 4 weeks was 5280 ug-hr/mL. The 2-week margins based on AUC of the predicted human exposures relative to the exposures in the toxicity studies for 70, 140, and 210 mg are 576, 74, and 39, respectively. For the 280 mg dose, the predicted 4 week margin was 121.

Pharmacokinetic (PK) data (serum drug concentrations measured at pre-specified time points) of AM-14 were collected for each subject in Study 1. Pharmacodynamic (PD) data (PASI score at baseline and pre-specified times post dose) were also collected for subjects in the final three cohorts (subjects diagnosed with moderate to severe plaque psoriasis). Modeling was performed on preliminary data to characterize the PK response in all subjects (based on actual dose administered) and to characterize the PD response (based on individual PK response).

Figure 10:
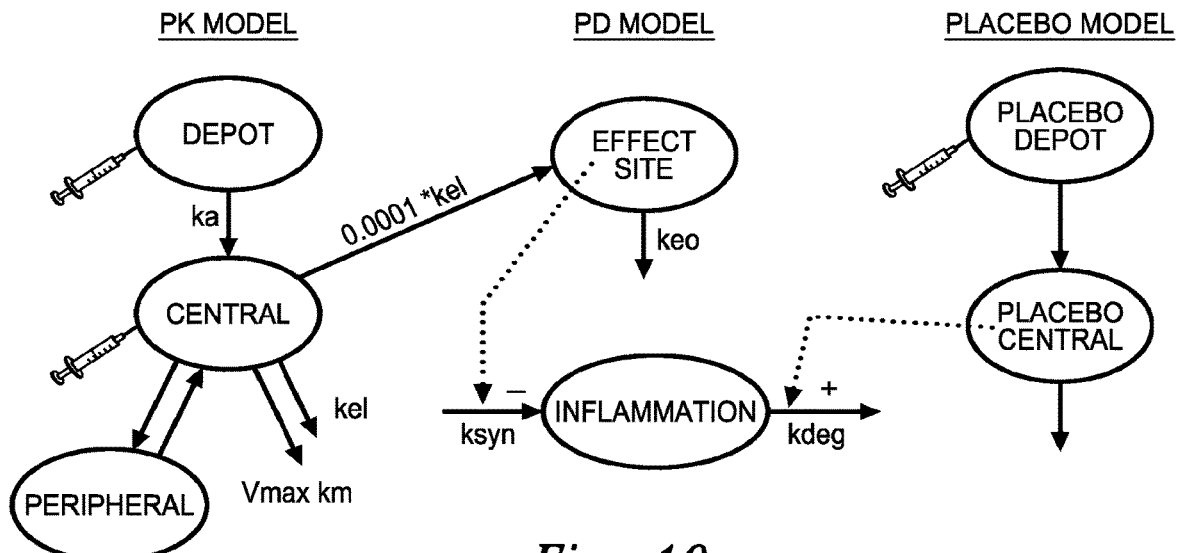
FIG. 10: A schematic of the PK-PD model used in some forms of analysis. The syringe indicates sites of dosing: a bolus to the depot (SC); an infusion to the central compartment (IV); or initiation of a placebo effect. Inflammation (as measured by PASI score) is represented by an inflammation compartment with endogenous rates of synthesis (ksyn) and degradation (kdeg). Drug concentrations in the effect compartment act to decrease ksyn and thereby decreasing inflammation. The placebo effect is modeled as a hypothetical compartment with its own kinetics. The placebo effect acts to increase kdeg and thereby decreasing inflammation.

A two compartment PK model with parallel linear and non-linear (Michaelis-Menten) elimination pathways and an added compartment for subcutaneous dose absorption was determined to best fit the data (see FIG. 10). Variance components were incorporated characterizing between-patient variability as well as residual variability. To model the PD, a peripheral effect site compartment was added to the model coupled with an indirect response model of inflammation synthesis and degradation. Placebo absorption and time-course compartments were compartment also added to model the time course of placebo response. Key assumptions in the model included: inflammation was measured as PASI score; drug concentrations in the effect site compartment inhibited inflammation synthesis; placebo effect acted to stimulate reduction of inflammation for all subjects; and endogenous synthesis (rate) of inflammation occurred until dose administration. Other PD models were also investigated but were found to be less optimal. The nonlinear mixed effects software NONMEM VI (Icon Development Solutions, Ellicott City, Md., USA.) was used to fit all models to data.

Figure 11:
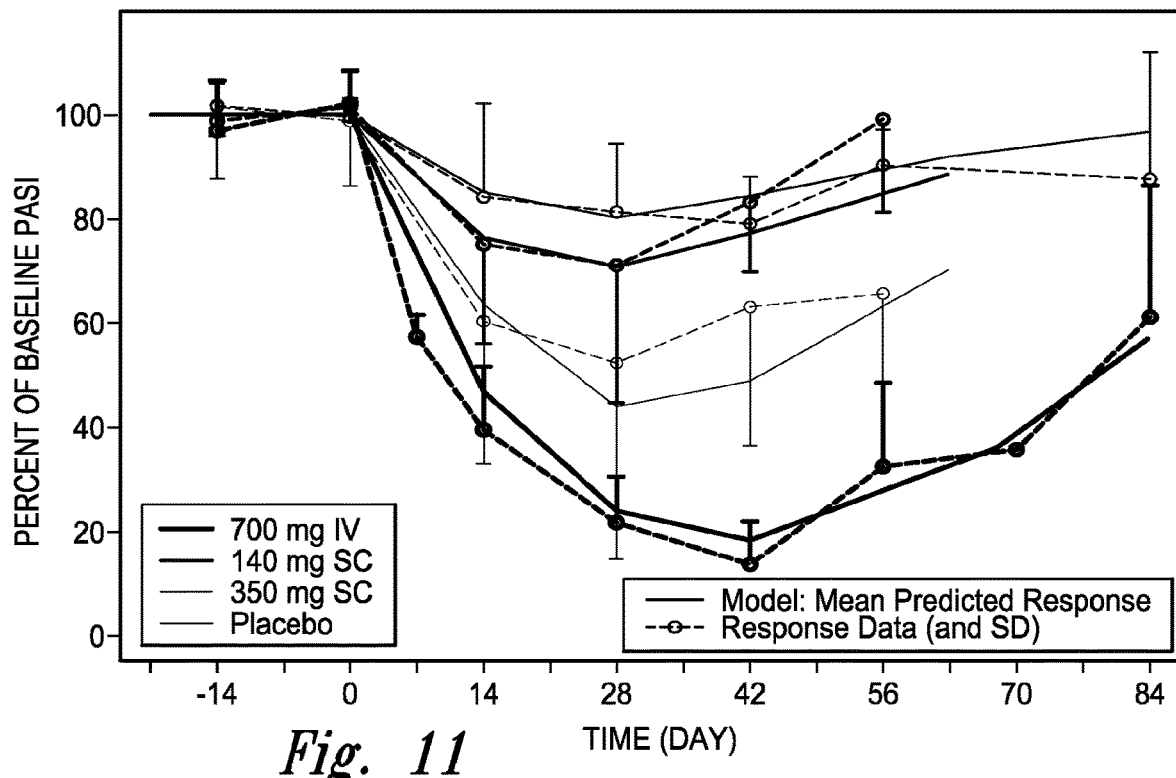
FIG. 11: A depiction of the mean model-predicted PASI (as percent of baseline) compared to mean (SD) observed PASI data (as percent of baseline by cohort) over time after single dose administration of AM-14 or placebo.

FIG. 11 compares observed and predicted mean PASI response time-course (as percent change from baseline) after single dose administration of AM-14 or placebo. The model characterizes well the actual PASI response data. Mean peak response for the highest dose (700 mg IV) was greater than 80% PASI improvement.

FIG. 12 presents predicted time course of mean PASI response for four multiple dose scenarios (over 12 weeks) including placebo effect based on the model developed from single dose data. The modeled placebo response was assumed to act after only the first dose, this being a conservative estimate. The mean response for the 140 mg SC dose (at WK 0, 1, 2, 4, 6, 8, 10) was expected to exceed 50% PASI improvement for much of the study period including the 12 week (day 84) primary efficacy endpoint. The mean response for the 210 and 280 mg SC doses (at WK 0, 1, 2, 4, 6, 8, 10) was expected to exceed 75% PASI improvement for much of the study period including the 12 week (day 84) primary efficacy endpoint. The predicted response for repeated 210 and 280 mg dosing is similar to, but of longer duration than, that observed for the single 700 mg IV dose, as shown in FIG. 11.

FIG. 13 depicts predicted week 12 dose responses for a range of doses (mg SC) given at WK 0, 1, 2, 4, 6, 8, and 10 based on the response predicted in FIG. 12 at day 84 (week 12). Dose-response curves (with 90% CI) are given for mean week 12 PASI response and percent of subjects expected to achieve PASI 50, 75, 90 at week 12.

Example 3

Gene Regulation in Psoriasis Patients with an IL-17 Antagonistic Antibody

The following data demonstrates that inhibition of IL-17R activation strongly influences gene regulation in psoriasis patients. Therefore, aspects of the invention include methods of regulating gene expression in psoriasis patients using IL-17 antagonistic antibodies. An "IL-17 antagonistic antibody" is an antibody that inhibits IL-17A or IL-17A/F from activating its cognate receptor(s) including IL-17RA, IL-17RC, and IL-17RA/RC. IL-17 antagonistic antibodies includes antibodies against IL-17RA or antibodies against IL-17A and/or IL-17A/F.

In patients from cohort 9 of Study 1 (see Example 2), predose 6 mm skin punch biopsies were taken from a non-lesional location and from a lesion that was large enough to support two further nearby biopsies after dosing. Two subsequent biopsies were taken two weeks and six weeks after treatment with AM-14, at the predesignated lesional positions, regardless of skin lesional appearance at the time of biopsy. The biopsies were immediately sliced longitudinally, with one half immediately placed into liquid nitrogen, and the other half frozen in standard OCT medium for IHC (immunohistochemistry). Placement into liquid nitrogen was specified to happen in less than two minutes after initial punch, and the OCT freezing specified to happen within five minutes of the initial punch. The frozen punches were maintained at −70 C or in dry ice.

RNA was prepared using standard Qiagen® or Ambion® RNA isolation kits from the punches without allowing them to thaw. The RNA was checked for quality and yield, and then processed with the NuGen Ovation® labeling kits for analysis on Affymetrix® U133plus2 microarrays. The data were transferred as .CEL files into Rosetta Resolver for analysis.

Ratios (Resolver id numbers 69671, 69672, and 69673) were calculated between the three sets of lesional samples (Predose, Day 15, and Day 43) versus the non-lesional baseline samples, to generate fold-change values, using only the Cohort 9 samples from patients receiving AM-14. Arrays used were barcodes skn47471, skn47475, skn48862, skn48866, skn48870, skn48876, skn48879, skn48883 (non-lesional), skn47470, skn47474, skn48861, skn48865, skn48869, skn48875, skn48878, skn48882 (lesional), skn47472, skn47476, skn48863, skn48867, skn48871, skn48877, skn48880, skn48884 (Day 15 Lesional), skn47473, skn47477, skn48864, skn48868, skn51554, skn48881, skn51556, and skn51557 (Day 43 Lesional). A set of sequences were identified as being increased in lesional versus non-lesional skin. Some of these sequences were selected for having high fold-change values, and others were selected from being commonly mentioned in the literature as being associated with the immunopathology of psoriasis or being a known drug target for the treatment of psoriasis, such as IL-23 and TNF.

An additional Resolver Ratio Experiment (#68458) of non-lesional versus lesional psoriasis gene expression was created using samples from psoriasis patients external to Study 1 (purchased through Asterand®, plc., Detroit, Mich.) These samples included microarray barcodes skn41609, skn41610, skn41611, skn41613, skn41614, skn41616, skn41617, skn41618, skn41619, skn41620, skn41621, skn41622, skn41623, skn41624, skn41625, skn41626, skn41698, skn41699, skn41702, skn47051, skn47052, skn47053, skn47054, skn47055, skn47056, skn47057, skn47058, skn47059, skn47060, skn47061, and skn47062. This ratio was used to confirm that the selected probe sets all represented sequences that were regulated in psoriasis, and could be properly observed in the study. The ratio values in this comparison were not as high as in the comparison between pre-dose lesional and non-lesional samples from the Study 1, which may be a result of various treatments being used by the individuals providing the external samples, who may not have had the same restrictions on medications.

TABLE 3.1

Psoriasis associated sequences have highly elevated expression in lesional relative to non-lesional skin, and almost completely resolve in lesional skin after treatment with AM-14. Gene (primary sequence) names are the current annotated Entrez names for the Affymetrix ® sequences whose IDs are the sequence codes in the second column.

| Primary Sequence Name | Sequence Code | 68458 External PsO NL vs. PsO L | 69671 Cohort 9 Pre NL vs. Cohort 9 Pre L | 69672 Cohort 9 Pre NL vs. Cohort 9 D 15 | 69673 Cohort 9 Pre NL vs. Cohort 9 D 43 |
|---|---|---|---|---|---|
| | | | Fold-Change | | |
| CXCL13 | 205242_at | 9.3 | 20.9 | 6.6 | 6.5 |
| GZMB | 210164_at | 3.7 | 7.8 | 2.6 | 1.6 |
| IFNG | 210354_at | 6.3 | 8.5 | 2.5 | 3.0 |
| IL12B | 207901_at | 10.0 | 4.3 | 0.8 | 1.0 |
| IL17A | 216876_s_at | 5.0 | 9.3 | 1.8 | 0.8 |
| IL17F | 234408_at | 3.2 | 3.4 | 0.9 | 1.0 |
| IL19 | 220745_at | 3.6 | 33.9 | 1.1 | 1.2 |
| IL1B | 39402_at | 6.5 | 24.0 | 1.4 | 0.9 |
| IL20 | 224071_at | 4.4 | 12.9 | 1.5 | 1.4 |
| IL22 | 222974_at | 3.1 | 10.7 | 1.6 | 1.0 |
| IL23A | 220054_at | 2.2 | 2.7 | 1.0 | 1.0 |
| IL8 | 202859_x_at | 3.9 | 58.9 | 1.1 | 0.7 |
| KRT16 | 209800_at | 4.4 | 6.5 | 1.0 | 1.5 |
| KRT6A | 209125_at | 2.8 | 3.3 | 1.1 | 1.2 |
| MMP12 | 204580_at | 5.8 | 4.3 | 0.6 | 0.9 |
| MX1 | 202086_at | 3.6 | 3.5 | 1.9 | 1.5 |
| NOS2 | 210037_s_at | 3.2 | 4.6 | 0.9 | 1.3 |
| S100A7A | 232170_at | 11.0 | 33.1 | 0.9 | 1.2 |
| S100A8 | 202917_s_at | 2.8 | 4.3 | 2.3 | 2.1 |
| S100A9 | 203535_at | 6.2 | 14.1 | 1.3 | 1.6 |
| SERPINB13 | 216258_s_at | 3.8 | 24.5 | 1.7 | 3.0 |
| SERPINB3 | 210413_x_at | 11.5 | 55.0 | 1.7 | 2.3 |
| SERPINB4 | 211906_s_at | 16.2 | 91.2 | 1.1 | 1.3 |
| TNF | 207113_s_at | 1.5 | 1.5 | 1.0 | 0.9 |
| Average | | 5.6 | 18.5 | 1.6 | 1.6 |

PsO = psoriasis; NL = non-lesional; L = lesional; Pre = predose

Notably in Table 3.1, many of the genes reduce their expression almost to the non-lesional baseline within two weeks of treatment with AM-14, in some cases going below the pre-dose level seen in the non-lesional skin. Notably, TNF is reduced to the non-lesional expression level (Fold-change=1.0), as is IL23A. IL19 is reduced to only 10 to 20% above non-lesional expression (Fold-change=1.1 to 1.2), while IL12B is actually reduced to below the non-lesional level (Fold-change=0.8 to 1.0). These changes are achieved within two weeks and broadly maintained at these low levels at six weeks. These unprecedented changes are very rapid across a wide set of genes that are implicated in the pathogenesis of psoriasis. To further dissect the changes in gene expression into functional groups of genes, RNAs from cytokine-stimulated keratinocytes were profiled on the Affymetrix® U133 chips. Triplicate stimulations for IL-17A and for IFN-gamma were averaged in ratios (#49933, and #49939) against triplicate controls. Profiles used were barcodes skn48829, skn48833, skn48837 (control), skn48830, skn48834, skn48838, (IL-17A), and skn48832, skn48836, skn48840 (IFN-gamma). Sequences (i.e., partial sequences of the designated genes) were selected from each stimulation experiment that would allow preferential monitoring of the effect of that cytokine. For example, sequences selected for the IFN-gamma signature were highly statistically significant, all induced at least 10-fold with IFN-gamma, and not induced more than 1.2 fold (20% increase) by IL-17A. Because IFN-gamma is such a strong stimulus, it was more difficult to select sequences for IL-17A that were unaffected by IFN-gamma, but in a similar fashion, IL-17A signature sequences were all statistically significant, more highly induced than other sequences with similar expression and were not induced significantly more by IFN-gamma. For both sets, the sequences were required to have increased expression in psoriasis lesional skin as compared to non-lesional. These two sets could then allow separate measurements of inflammation along each axis to dissect the effects of AM-14 treatment.

As shown below in table 3.2, eighteen sequences were selected for the IL-17 signature based on their elevation in the IL-17A keratinocyte stimulation, without higher skewed expression in the IFN-gamma stimulations. In both the external psoriasis samples and in the Cohort 9 samples, the sequences are elevated in psoriatic lesional skin. As can be seen in the last two columns, these sequences have a dramatic reduction in expression, returning close to non-lesional levels after AM-14 treatment. From an average of over 28-fold higher expression in the predose lesional biopsies, they return to an average of less than two-fold within two weeks after treatment with AM-14. Some, including the defensins S100A7 and DEF4B have expression levels below the original non-lesional levels.

TABLE 3.2

Expression of IL-17A inducible genes in keratinocytes treated with IL-17A or IFN-gamma, or in psoriasis skin samples. Eighteen sequences were chosen as elevated with IL-17A stimulation for 24-hours in human keratinocytes, and their fold-change values determined for induction in keratinocytes after 24-hour cytokine stimulation, non-lesional versus lesional external samples, or from psoriatic lesions (with or without AM-14 treatment) in comparison to pre-dose non-lesional samples.

| | | Experiment ID | | | | | |
|---|---|---|---|---|---|---|---|
| | | 49933 | 49939 | 68458 | 69671 | 69672 | 69673 |
| | | Experiment Name | | | | | |
| Primary Sequence Name | Sequence Code | Neg Control vs. IL-17A | Neg Control vs. IFNg | PsO NL vs. PsO L | 20060279 Predose Non-lesional vs. PreDose Lesional | 20060279 Predose Non-lesional vs. D15 | 20060279 Predose Non-lesional vs. D43 |
| | | Fold-Change | | | | | |
| C15orf148 | 223484_at | 4.7 | 5.5 | 2.5 | 3.8 | 0.6 | 0.8 |
| CCL20 | 205476_at | 4.2 | 0.9 | 5.8 | 28.8 | 1.7 | 1.4 |

TABLE 3.2-continued

Expression of IL-17A inducible genes in keratinocytes treated with IL-17A or IFN-gamma, or in psoriasis skin samples. Eighteen sequences were chosen as elevated with IL-17A stimulation for 24-hours in human keratinocytes, and their fold-change values determined for induction in keratinocytes after 24-hour cytokine stimulation, non-lesional versus lesional external samples, or from psoriatic lesions (with or without AM-14 treatment) in comparison to pre-dose non-lesional samples.

| | | Experiment ID | | | | | |
|---|---|---|---|---|---|---|---|
| | | 49933 | 49939 | 68458 | 69671 | 69672 | 69673 |
| | | Experiment Name | | | | | |
| Primary Sequence Name | Sequence Code | Neg Control vs. IL-17A | Neg Control vs. IFNg | PsO NL vs. PsO L | 20060279 Predose Non-lesional vs. PreDose Lesional | 20060279 Predose Non-lesional vs. D15 | 20060279 Predose Non-lesional vs. D43 |
| | | Fold-Change | | | | | |
| CXCL1 | 204470_at | 3.4 | 1.7 | 4.4 | 38.9 | 4.6 | 4.1 |
| CXCL6 | 206336_at | 6.0 | 0.5 | 4.2 | 17.8 | 1.5 | 1.2 |
| DEFB4 | 207356_at | 45.7 | 5.4 | 8.9 | 33.1 | 0.6 | 0.8 |
| IL1F9 | 220322_at | 5.4 | 2.8 | 4.9 | 22.9 | 1.6 | 2.9 |
| LCN2 | 212531_at | 3.7 | 0.5 | 8.5 | 13.8 | 3.8 | 4.2 |
| PDZK1IP1 | 219630_at | 10.2 | 11.5 | 2.6 | 6.0 | 1.0 | 1.6 |
| PDZK1IP1 | 1553589_a_at | 9.8 | 10.7 | 2.6 | 7.1 | 1.1 | 1.4 |
| RHCG | 219554_at | 2.8 | 1.2 | 4.6 | 11.2 | 0.6 | 0.7 |
| S100A12 | 205863_at | 4.1 | 2.1 | 14.1 | 95.5 | 1.7 | 0.3 |
| S100A7 | 205916_at | 6.8 | 2.1 | 1.9 | 2.9 | 1.3 | 1.4 |
| SAA1 | 208607_s_at | 4.3 | 3.7 | 1.6 | 3.7 | 3.5 | 4.9 |
| SAA1 | 214456_x_at | 2.9 | 2.8 | 2.0 | 3.6 | 4.0 | 3.7 |
| SPRR2C | 220664_at | 5.9 | 0.9 | 10.5 | 32.4 | 0.5 | 0.5 |
| TMPRSS11D | 207602_at | 7.8 | 6.3 | 4.1 | 89.1 | 2.3 | 0.8 |
| VNN3 | 220528_at | 83.2 | 11.0 | 8.9 | 100.0 | 2.9 | 1.7 |
| ZC3H12A | 218810_at | 3.2 | 1.8 | 3.0 | 4.7 | 1.7 | 1.4 |
| | Average | 11.9 | 4.0 | 5.3 | 28.6 | 1.9 | 1.9 |

As shown below in Table 3.3, thirty-three sequences were selected for the IFN-gamma signature based on their elevation in the IFN-gamma keratinocyte stimulation, without higher expression in the IL-17A stimulations. In both the external psoriasis samples and in Study 1 samples, the sequences are elevated in lesional skin. As can be seen in the last two columns, these sequences have a substantial, but incomplete reduction in expression, returning towards non-lesional levels following treatment with AM-14. Some, such as CCL2 and IRF1 have non-lesional or lower expression levels within two weeks of treatment with AM-14 while others such as CCL7 and TNFRSF9 continue to decrease over time.

TABLE 3.3

Expression of IFN-gamma inducible genes in keratinocytes stimulated with IL-17A or IFN-gamma, or in psoriasis skin samples. Thirty-three sequences were chosen as elevated with IL-17A stimulation for 24-hours in human keratinocytes, and their fold-change values determined for induction in keratinocytes after 24-hour cytokine stimulation, non-lesional versus lesional external samples, or from psoriatic lesions (with or without AM-14 treatment) in comparison to pre-dose non-lesional samples.

| | | Experiment ID | | | | | |
|---|---|---|---|---|---|---|---|
| | | 49933.0 | 49939.0 | 68458.0 | 69671.0 | 69672.0 | 69673.0 |
| | | Experiment Name | | | | | |
| Primary Sequence Name | Sequence Code | Neg Control vs. IL-17A | Neg Control vs. IFNg | PsO NL vs. PsO L | 20060279 Predose Non-lesional vs. PreOose Lesional | 20060279 Predose Non-lesional vs. 015 | 20060279 Predose Non-lesional vs. 043 |
| | | Fold-Change | | | | | |
| 1570541_s_at | 1570541_s_at | 1.0 | 100.0 | 5.5 | 6.5 | 2.1 | 1.9 |
| 239979_at | 239979_at | 0.8 | 17.0 | 4.2 | 3.3 | 2.4 | 2.2 |
| ACE2 | 219962_at | 1.0 | 31.6 | 4.9 | 8.5 | 1.5 | 1.6 |
| AIM2 | 206513_at | 0.8 | 100.0 | 5.5 | 4.3 | 1.9 | 1.7 |
| APOL1 | 209546_s_at | 0.9 | 63.1 | 2.7 | 2.6 | 1.3 | 1.1 |
| APOL6 | 219716_at | 0.9 | 17.8 | 3.3 | 2.7 | 1.1 | 0.8 |
| APOL6 | 241869_at | 0.7 | 41.7 | 4.1 | 1.9 | 1.1 | 1.0 |

TABLE 3.3-continued

Expression of IFN-gamma inducible genes in keratinocytes stimulated with IL-17A or IFN-gamma, or in psoriasis skin samples. Thirty-three sequences were chosen as elevated with IL-17A stimulation for 24-hours in human keratinocytes, and their fold-change values determined for induction in keratinocytes after 24-hour cytokine stimulation, non-lesional versus lesional external samples, or from psoriatic lesions (with or without AM-14 treatment) in comparison to pre-dose non-lesional samples.

| | | Experiment ID | | | | | |
|---|---|---|---|---|---|---|---|
| | | 49933.0 | 49939.0 | 68458.0 | 69671.0 | 69672.0 | 69673.0 |
| | | | | Experiment Name | | | |
| Primary Sequence Name | Sequence Code | Neg Control vs. IL-17A | Neg Control vs. IFNg | PsO NL vs. PsO L | 20060279 Predose Non-lesional vs. PreOose Lesional Fold-Change | 20060279 Predose Non-lesional vs. 015 | 20060279 Predose Non-lesional vs. 043 |
| CCL22 | 207861_at | 0.9 | 22.4 | 3.5 | 3.5 | 0.9 | 1.2 |
| CCL5 | 1405_i_at | 0.2 | 22.4 | 1.5 | 1.4 | 2.2 | 2.1 |
| CCL5 | 204655_at | 0.3 | 20.0 | 1.4 | 1.3 | 2.3 | 1.8 |
| CCL7 | 208075_s_at | 0.5 | 89.1 | 3.8 | 5.4 | 1.6 | 1.0 |
| CCL8 | 214038_at | 0.8 | 100.0 | 1.7 | 1.8 | 1.3 | 1.0 |
| CLEC7A | 221698_s_at | 0.9 | 21.4 | 2.8 | 3.6 | 1.9 | 1.7 |
| EBI3 | 219424_at | 0.4 | 21.4 | 3.6 | 3.1 | 1.3 | 1.1 |
| GBP4 | 235175_at | 1.0 | 100.0 | 1.8 | 1.2 | 1.3 | 1.1 |
| GBP5 | 238581_at | 0.8 | 100.0 | 6.6 | 4.6 | 3.1 | 2.1 |
| GBP5 | 229625_at | 0.8 | 91.2 | 3.0 | 3.3 | 2.6 | 2.2 |
| IFIT3 | 204747_at | 0.9 | 21.4 | 2.9 | 3.0 | 1.1 | 1.3 |
| IL12RB1 | 1552584_at | 0.6 | 61.7 | 2.0 | 2.3 | 1.7 | 1.6 |
| IL2RG | 204116_at | 0.6 | 67.6 | 2.0 | 2.0 | 1.3 | 1.5 |
| IL32 | 203828_s_at | 0.5 | 19.5 | 2.1 | 1.4 | 1.5 | 1.8 |
| IRF1 | 238725_at | 0.8 | 83.2 | 1.9 | 1.3 | 1.0 | 0.9 |
| ISG20 | 33304_at | 1.0 | 53.7 | 3.2 | 3.2 | 1.3 | 1.3 |
| ISG20 | 204698_at | 1.2 | 45.7 | 2.9 | 2.8 | 1.3 | 1.1 |
| LIPA | 236156_at | 0.7 | 27.5 | 2.9 | 2.3 | 1.4 | 1.0 |
| RSAD2 | 213797_at | 1.1 | 46.8 | 6.0 | 9.8 | 2.5 | 1.6 |
| RSAD2 | 242625_at | 1.1 | 52.5 | 4.5 | 3.9 | 1.3 | 1.1 |
| RTP4 | 219684_at | 0.6 | 100.0 | 4.3 | 6.0 | 3.2 | 1.9 |
| SAMD9L | 226603_at | 0.8 | 19.1 | 1.7 | 1.5 | 1.4 | 1.3 |
| SLC15A3 | 219593_at | 1.0 | 100.0 | 1.3 | 1.0 | 1.0 | 1.0 |
| TNFRSF9 | 211786_at | 0.6 | 14.1 | 3.1 | 3.3 | 2.1 | 1.5 |
| TRIM10 | 221627_at | 0.7 | 21.4 | 4.2 | 13.8 | 3.6 | 3.6 |
| XAF1 | 206133_at | 0.9 | 16.6 | 2.3 | 1.8 | 1.6 | 1.2 |
| | Average | 0.8 | 51.7 | 3.1 | 3.4 | 1.7 | 1.5 |

The gene sets for IL-17A and IFN-gamma response were further trimmed to remove two sequences each that had extremely high correlation coefficients with another sequence from the same gene. The probe sets 208607_s_at (SAA1) and 219630_at (PDZK1IP1) were dropped from the IL-17A signature set in Table 3.2, and the probe sets 1405_i_at (CCL5) and 213797_at (RSAD2) were excluded from the IFN-gamma signature set in Table 3.3. The remaining sequences were used to calculate a Mahalanobis distance based on a core set of skin profiles from normal individuals for each sequence set (Table 3.4). In this calculation, the set of base case normal skin samples are used to define the mean for each sequence and a sequence set covariance matrix, which is used in combination with the normalized sequence intensities of each sample to define a Mahalanobis distance metric for that sample on that gene set. Distances were also calculated for external non-lesional, and lesional samples, which are in a similar range to the pre-dose samples from Study 1. Not surprisingly for these two sets of inflammatory cytokine-regulated gene sets, the lesional skin samples have much higher signature distances than the non-lesional samples. This is true for both the external sample set, and for the pre-dose samples for this study. Surprisingly, the large pre-dose signature distances are dramatically decreased with a single dose of AM-14, with the IFN-gamma signature distance dropping most of the way towards the non-lesional value, and the IL-17A signature distance dropping even below the non-lesional value.

TABLE 3.4

| | Average Mahalanobis Distance | |
|---|---|---|
| | IFN-gamma Distance | IL17A Distance |
| NonLesional PreDose | 674 | 10403 |
| Lesional PreDose | 8465 | 627631 |
| Lesional Day 15 | 2338 | 4133 |
| Lesional Day 43 | 1705 | 1329 |
| NonLesional External | 712 | 82285 |
| Lesional External | 11122 | 649648 |

Overall these data show a dramatic molecular change (i.e., downregulating genes that are implicated in the pathogenesis of psoriasis) in the psoriasis lesional skin as a result of AM-14 treatment that happens rapidly and is sustained or increased through six weeks after dosing. The change is observed across a wide range of genes that are involved in inflammation and recognized as being affected by psoriasis. It is also observed in a set of genes that are upregulated by IFN-gamma in keratinocytes, and is most striking in a set of genes that are upregulated by IL-17A. This genotypic response correlates with the percent reduction in PASI scores shown in Example 2 for patients treated with AM-14. The rapidity of the morphological and genotypic responses in the psoriasis patients treated with AM-14 is unprecedented and may be unique to AM-14 (and the other anti-IL-17RA antibodies disclosed herein) as well as IL-17RA antagonists, as defined herein, such as antibodies that bind IL-17A and block its binding to IL-17RA and/or IL-17RC and/or heteromeric receptors comprising IL-17RA and IL-17RC.

Example 4

Figure 14:
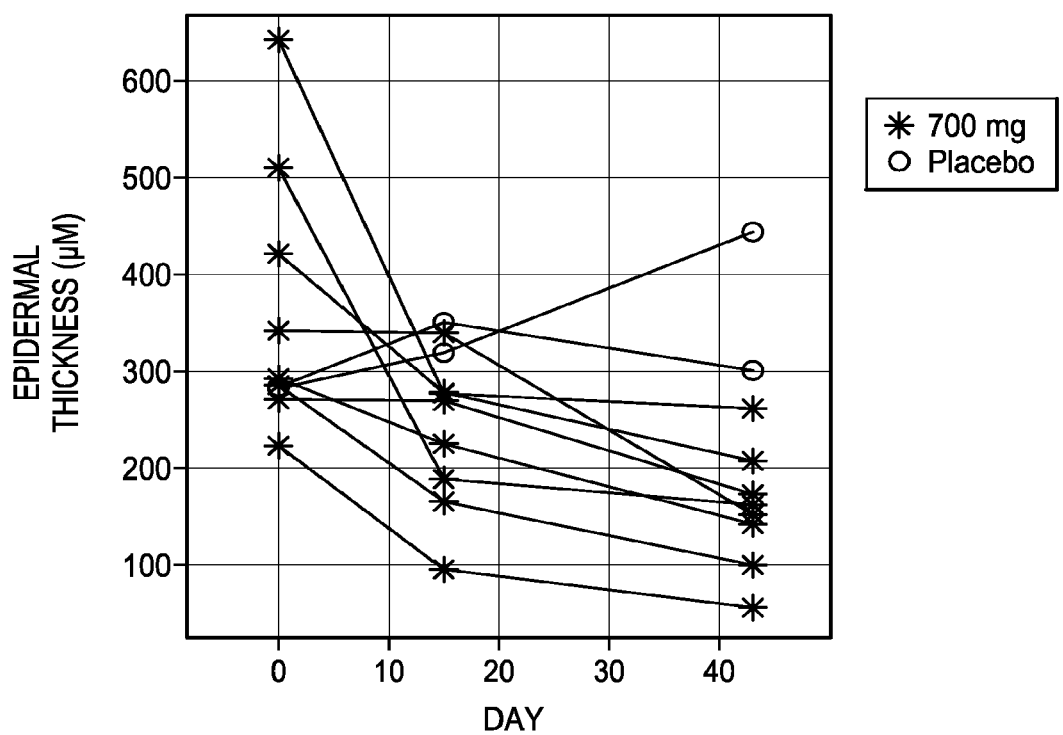
FIG. 14: A graph depicting changes in epidermal thickness over time in subjects receiving AM-14 (filled object) compared to placebo (empty circles). Administration of AM-14 led to significant reductions in epidermal thickness in psoriasis subjects compared to placebo.
Figure 15:
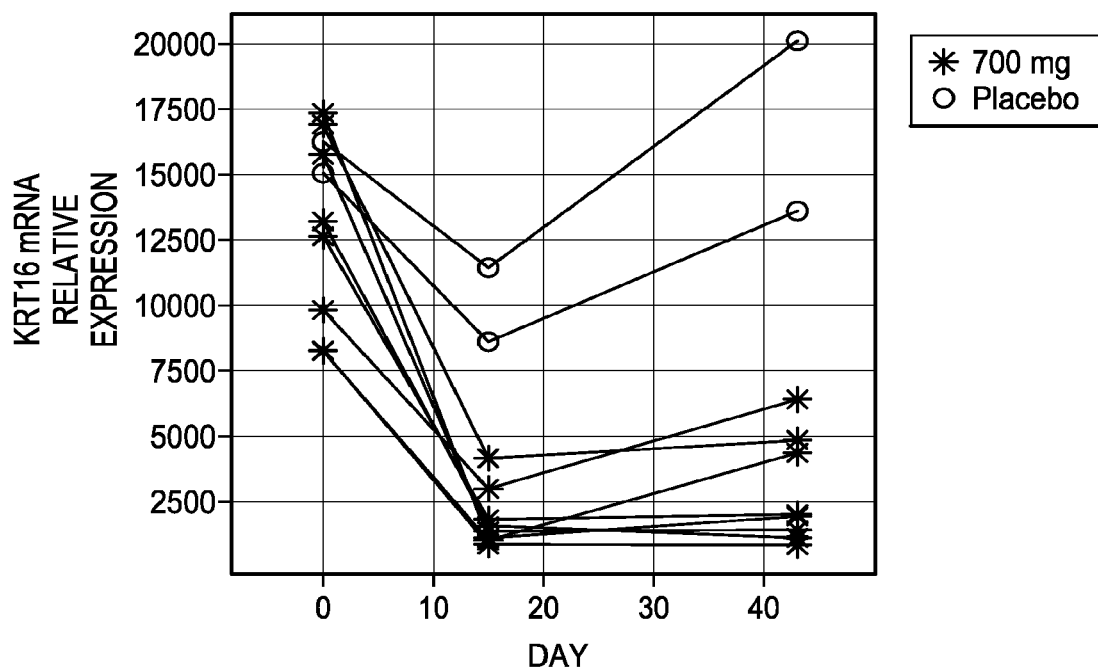
FIG. 15: A graph depicting changes in Keratin-16 (KRT16) over time in subjects receiving AM-14 (filled object) compared to placebo (empty circles). Administration of AM-14 led to significant reductions in KRT16 mRNA in psoriasis subjects compared to placebo.
Figure 16:
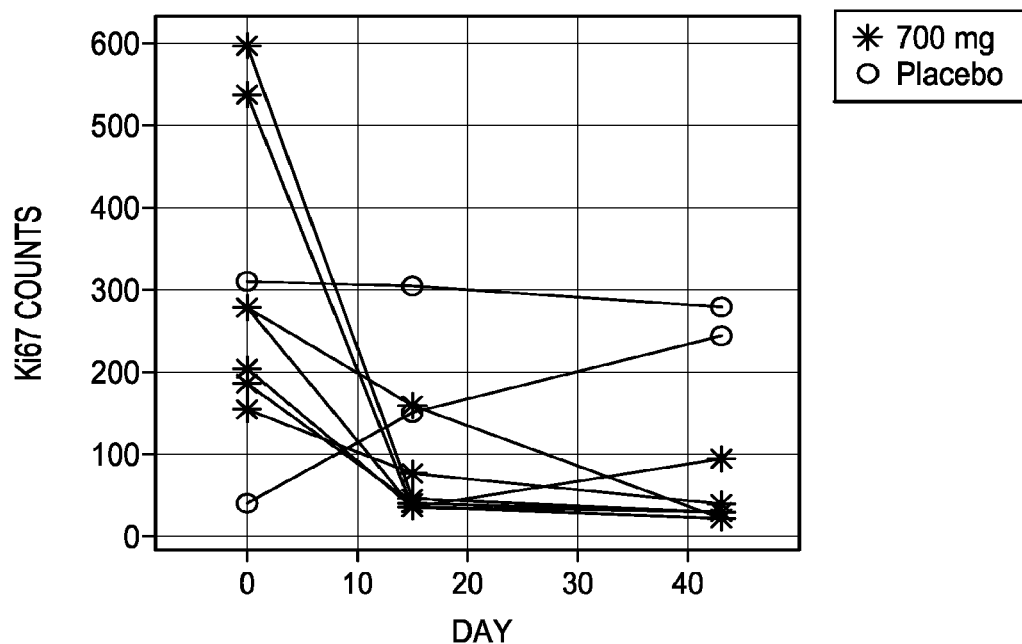
FIG. 16: A graph depicting changes in Ki67 counts over time in subjects receiving AM-14 (filled object) compared to placebo (empty circles). AM-14 led to significant reductions in Ki67 counts in psoriasis subjects compared to placebo.

Histological Analysis of Psoriasis Patients Treated with an Anti-IL-17 Receptor "A" Monoclonal Antibody The following experiments demonstrate that inhibition of IL-17R activation strongly influences histopathological responses in psoriasis patients. Treatment with AM-14 (700 mg IV single doses) in subjects with psoriasis led to significant improvements in multiple histopathologic parameters compared to placebo. These parameters including epidermal thickness, Ki-67 and Keratin-16 levels. These data are presented in FIGS. 14, 15, and 16. FIG. 14 shows the changes in epidermal thickness over time in subjects receiving AM-14 (filled object). Administration of AM-14 led to significant reductions in epidermal thickness in psoriasis subjects compared to placebo. compared to placebo (empty circles). FIG. 15 depicts the changes in Keratin-16 (KRT16) over time in subjects receiving AM-14 (filled object) compared to placebo (empty circles). Administration of AM-14 led to significant reductions in KRT16 mRNA in psoriasis subjects compared to placebo. FIG. 16 depicts the changes in Ki67 counts over time in subjects receiving AM-14 (filled object) compared to placebo (empty circles). Administration of AM-14 led to significant reductions in Ki67 counts in psoriasis subjects compared to placebo.

In addition, treatment with AM-14 as described in the preceding paragraph reduced the numbers of infiltrating dermal leukocyte subsets (CD3+, CD11c+, CD8+, DC-LAMP+) as described in Table 4.0. The reductions in leukocyte subsets indicate that both T-cells (CD3+ and CD8+) and mature dendritic cells (CD11c+ and DC-LAMP+) were reduced by treatment with AM-14. Both of these cellular subsets have been implicated in amplifying and maintaining the pro-inflammatory milieu in psoriatic skin. The histopathologic data correlated with significant PASI improvements, as 7 of 8 subjects achieved at least 75% improvement in PASI score at week 6. Together these data identify numerous histologic consequences of IL-17 activation and subsequent inhibition in human skin by AM-14.

TABLE 4.0

| Subject | NL | LS d 0 | LS d 14 | LS d 42 |
|---|---|---|---|---|
| CD3+ | | | | |
| AM-14A | 92 | 305 | 258 | 149 |
| AM-14 B | 171 | 139 | 144 | 83 |
| PBO A | 8 | 155 | 508 | 247 |
| AM-14 C | 27 | 368 | 253 | 105 |
| AM-14 D | 50 | 507 | 0 | 176 |
| PBO B | 37 | 295 | 338 | 374 |
| AM-14 E | NA | 600 | 284 | 201 |
| AM-14 F | 57 | 143 | 153 | 168 |
| AM-14 G | 54 | 248 | 244 | 88 |
| AM-14 H | 46 | 177 | 102 | 54 |
| mean | 71 | 311 | 180 | 128 |
| sd | 48 | 171 | 98 | 53 |
| CD11c+ | | | | |
| AM-14 A | 189 | 478 | 336 | 168 |
| AM-14 B | 57 | 205 | 124 | 167 |
| PBO A | 30 | 141 | 264 | 298 |
| AM-14 C | 85 | 322 | 696 | 85 |
| AM-14 D | 72 | 463 | 235 | 228 |
| PBO B | 77 | 192 | 488 | 985 |
| AM-14 E | | 358 | 156 | 156 |
| AM-14 F | 108 | 987 | 318 | 150 |
| AM-14 G | 42 | 128 | 93 | 78 |
| AM-14 H | 79 | 204 | 285 | 109 |
| mean | 90 | 393 | 280 | 143 |
| sd | 48 | 271 | 191 | 50 |
| CD8+ | | | | |
| AM-14 A | | | | |
| AM-14 B | 35 | 103 | 61 | 19 |
| PBO A | 11 | 64 | 92 | 43 |
| AM-14 C | 56 | 56 | 150 | 39 |
| AM-14 D | 26 | 118 | 165 | 89 |
| PBO B | 7 | 30 | 60 | 172 |
| AM-14 E | | 231 | 67 | 46 |
| AM-14 F | 6 | 284 | 55 | 106 |
| AM-14 G | 47 | 28 | 64 | 48 |
| AM-14 H | 72 | 132 | 63 | 48 |
| mean | 40 | 136 | 89 | 56 |
| sd | 23 | 92 | 47 | 30 |
| DC-LAMP | | | | |
| AM-14 A | | | | |
| AM-14 B | 10 | 48 | 19 | 11 |
| PBO A | 0 | 92 | 60 | 59 |
| AM-14 C | 5 | 67 | 148 | 8 |
| AM-14 D | 0 | 32 | 15 | 45 |
| PBO B | 0 | 98 | 142 | 250 |
| AM-14 E | | 267 | 5 | 2 |
| AM-14 F | 0 | 150 | 28 | 14 |
| AM-14 G | 0 | 42 | 6 | 4 |
| AM-14 H | 0 | 56 | 3 | 0 |
| mean | 3 | 95 | 32 | 12 |
| sd | 4 | 86 | 52 | 15 |

Example 5

Glutamate Formulation Sting Study

Six formulation buffers were tested in a total of 72 healthy human participants over a three-day period of time. None of the buffers contained antibody. Participants assessed and recorded perceived pain/stinging after each buffer injection using 100-mm visual analog scale where larger numbers represent more pain (referred to as VAS). After all injections were administered, participants ranked-ordered the buffers by pain/stinging perceived from least to most painful (buffers 1-6).

The following six buffers were assessed:
A: 10 mM sodium acetate, pH 5.2, 9% sucrose, 0.004% polysorbate 20;
B: 10 mM sodium glutamate, pH 4.8, 9% sucrose, 0.01% polysorbate 20;
C: 30 mM sodium glutamate, pH 4.8, 8% sucrose, 0.01% polysorbate 20;
D: 10 mM sodium acetate, pH 4.8, 3% L-proline, 0.01% polysorbate 20;
E: 30 mM sodium glutamate, pH 4.8, 3% L-proline, 0.01% polysorbate 20; and
F: 20 mM sodium citrate, pH 5.0, 5% sorbitol.

Buffer A was the AM-14 formulation buffer used in the clinical studies described in Examples 2-4 and 6 and was designated as the "comparator" buffer. Buffer F was a citrate-based buffer and was considered a "positive control" buffer for assessing relative pain/stinging due to its reputation in the art for causing stinging in subcutaneous injections.

The results of the study demonstrate that: (a) subcutaneous injection of the positive control buffer (F) resulted in measurable transient localized pain (stinging) at injection site (mean VAS score=56.9 mm (SD=±30.64), median VAS score=59.5 mm); (b) subcutaneous injection of the other buffers (A-E) resulted in significantly less reported stinging (mean VAS scores ranging from 12.1 mm to 28.4 mm, median VAS scores of 4.5 mm to 15.0 mm, p<0.0001); (c) based on mean VAS scores, the order (least to worst) of reported stinging by the buffers was B<A<D<E<C<F; (d) based on median VAS scores, the order (least to worst) of reported stinging by the buffers was B<A<D<C<E<F; (e) after all injections were administered, participants ranked the buffers (1-6) by sting perceived from least to most painful. The median participant ranking of sting was buffers A=B=D<buffers C=E<buffer F; (f) pair-wise comparisons of VAS scores demonstrated that sting induced by comparator buffer A and buffers B and D were indistinguishable (p=0.47 and 0.07, respectively), however, stinging induced by buffer B was less than that for buffer D (p=0.01), and that buffers containing 30 mM glutamate (buffer C and E) caused somewhat more stinging than the buffer containing 10 mM glutamate (buffer B, p≤0.0005). The pair-wise comparisons are provided in Table 5.0, below.

This data demonstrates the unexpected result that a 10 mM glutamate-based formulation does not induce an unacceptable degree of stinging in humans upon subcutaneous injection.

TABLE 5.0

Summary of Pairwise Vehicle Comparison of Pain Scores

| Treatments Compared | Difference | Confidence Interval Coverage | Lower | Upper | p-value |
| --- | --- | --- | --- | --- | --- |
| A vs F | −42.3 | 90 | −48.0 | −36.6 | <0.0001 |
| B vs F | −44.8 | 95 | −51.6 | −38.0 | <0.0001 |
| C vs F | −28.4 | 95 | −35.3 | −21.6 | <0.0001 |
| D vs F | −36.0 | 95 | −42.8 | −29.2 | <0.0001 |
| E vs F | −32.6 | 95 | −39.5 | −25.8 | <0.0001 |
| A vs B | 2.5 | 90 | −3.2 | 8.2 | 0.4700 |
| A vs D | −6.3 | 90 | −12.0 | −0.6 | 0.0711 |
| B vs D | −8.8 | 95 | −15.6 | −2.0 | 0.0117 |
| B vs C | −16.4 | 95 | −23.2 | −9.5 | <0.0001 |
| B vs E | −12.2 | 95 | −19.0 | −5.3 | 0.0005 |

Example 6

AM-14 Phase 2 Psoriasis Study

A Phase 2 randomized, double-blind, placebo-controlled, multiple-dose study to evaluate the safety, tolerability, and efficacy of AM-14 in subjects with moderate to severe plaque psoriasis was performed to establish a dose-response efficacy profile of AM-14 compared with placebo as measured by the percent improvement from baseline in Psoriasis Area and Severity Index (PASI) score at week 12 and to identify an appropriate dose regimen for future trials. For additional information see ClinicalTrials.gov Identifier no. NCT00975637.

Inclusion Criteria:
Subject has had stable moderate to severe plaque psoriasis for at least 6 months
Subject has received at least one previous phototherapy or systemic psoriasis therapy or has been a candidate to receive phototherapy or systemic psoriasis therapy in the opinion of the investigator
Subject has involved BSA 10% and PASI 12 at screening and at baseline.

Exclusion Criteria:
Subject diagnosed with erythrodermic psoriasis, pustular psoriasis, medication-induced, or medication-exacerbated psoriasis
Evidence of skin conditions at the time of the screening visit (eg, eczema, guttate psoriasis) that would interfere with evaluations of the effect of IP on psoriasis
Subject has any active CTCAE grade 2 or higher infection
Subject has a significant concurrent medical condition or laboratory abnormalities, as defined in the study protocol
Subject has used the following therapies within 14 days of the first dose: UVB therapy or topical psoriasis therapies other than Class I or II topical steroids
Subject has used the following therapies within 28 days of the first dose: Class I or II topical steroids, UVA therapy (with or without psoralen), or systemic psoriasis therapies
Subject has used the following therapies within 3 months of the first dose: adalimumab, alefacept, etanercept, infliximab, certolizumab, or live vaccines
Subject has used an anti-IL12/IL23 inhibitor within 6 months of the first dose
Subject has previously used an anti-IL17 biologic therapy, efalizumab, or rituximab The study evaluated the efficacy of AM-14 compared with placebo as measured by the percent improvement in PASI score at week 12. After signing informed consent forms, completing all screening assessments, and meeting all eligibility criteria, approximately 175 subjects were randomized in a 1:1:1:1:1 ratio and received AM-14 and/or placebo at day 1 and weeks 1, 2, 4, 6, 8, and 10. Subjects were randomized to receive AM-14 received 70, 140, or 210 mg at day 1 and weeks 1, 2, 4, 6, 8, and 10 or 280 mg at day 1 and weeks 4 and 8. For approximately 50 subjects, additional samples at additional timepoints for PK analysis were collected as a sub-study. For approximately 175 subjects in the main study, PK assessments with sparse sampling were performed. Randomization was stratified to assure treatment balance in the PK substudy and by body mass index (above and below 35). Skin samples were collected from approximately 32 subjects at a subgroup of participating sites at day 1 (1 each, lesional and nonlesional), week 2 (lesional only), and week 12 (lesional only). Serum, plasma, and blood RNA was collected for all subjects.

AM-14 was provided as a sterile, preservative-free liquid containing 70 mg/mL AM-14 formulated in 10 mM sodium acetate, 9% sucrose, 0.004% w/v polysorbate 20 at pH 5.2. The formulation was supplied as a frozen liquid in glass vials containing 1 mL deliverable volume (single use only). Placebo clinical supply was provided in glass vials as a frozen, sterile protein-free solution. The vials were single-use vials containing approximately 1 mL of vehicle solution per vial. The control group received placebo at day 1 and weeks 1, 2, 4, 6, 8, and 10 (Q2WK+week 1). Other subjects received one or more placebo shots as needed to maintain the blinded nature of the study.

PASI assessments were performed by a blinded assessor. The blinded assessor was a healthcare professional who has been certified as trained with the standard PASI training material provided by Amgen. To maintain the blind, the assessor did not have any other interaction with the subjects other than the PASI, sPGA, and BSA involvement assessments. The assessor did not discuss the subject's clinical status or have access to the subjects' medical records or CRFs including prior assessment data. PASI assessments were performed by the same assessor throughout the study.

The PASI 75, 90, and 100 responses at week 12 are provided in Table 6.0, below. This study shows AM-14 is efficacious at treating psoriasis (in particular, moderate to severe plaque psoriasis) at doses ranging from 70 to about 300 mg, and specifically at doses of 70, 140, 210, and 280 mg at the dosing regimens described above. These data show that AM-14 showed efficacy over placebo at all doses tested (70, 140, 210, and 280)

TABLE 6.0

PASI 75, 90, 100 Responses at Week 12

|  | Placebo (N = 38) n/N1 (%) | AM-14 70 mg q2W (N = 39) n/N1 (%) | AM-14 140 mg q2W (N = 39) n/N1 (%) | AM-14 210 mg q2W (N = 40) n/N1 (%) | AM-14 280 mg q4W (N = 42) n/N1 (%) |
|---|---|---|---|---|---|
| PASI 75 Response | 0/38 (0.0%) | 13/39 (33.3%) | 30/39 (76.9%) | 33/40 (82.5%) | 28/42 (66.7%) |
| P value |  | <0.0001 | <0.0001 | <0.0001 | <0.0001 |
| PASI 90 Response | 0/38 (0.0%) | 7/39 (17.9%) | 28/39 (71.8%) | 30/40 (75.0%) | 24/42 (57.1%) |
| P value |  | 0.0057 | <0.0001 | <0.0001 | <0.0001 |
| PASI 100 Response | 0/38 (0.0%) | 4/39 (10.3%) | 15/39 (38.5%) | 25/40 (62.5%) | 12/42 (28.6%) |
| P value |  | 0.0452 | <0.0001 | <0.0001 | 0.0003 |

N = Number of participants randomized
n = Number of responders
N1 = Number of participants who were randomized and had a valid measurement value at week 12, after imputation % = n/N1*100
P value is for comparison between each AM-14 dose group and placebo and is nominal without multiplicity adjustment
P value was based on the Cochran-Mantel-Haenszel Test stratified by BMI (Body Mass Index) group (≤35, >35) and adjusted for baseline PASI group (≤median (17.45), >median (17.49))
NRI (NonResponder Imputation) was used to impute missing data

The invention claimed is:

1. A method of treating Sjögren's syndrome, dermatomyositis, or systemic lupus erythematosus in a human patient in need thereof, which method comprises administering to the patient an effective amount of a formulation comprising (i) 30 mM glutamic acid, (ii) a pH of 4.8±0.2, (iii) 3±0.2% proline (w/v), (iv) 0.01±0.002% (w/v) polysorbate 20, and (v) about 140 mg/mL of a human monoclonal antibody or an antigen-binding fragment thereof that binds to human IL-17 Receptor A, wherein the human monoclonal antibody comprises:

(a) a heavy chain CDR1 comprising the amino acid sequence of SEQ ID NO: 5, a heavy chain CDR2 comprising the amino acid sequence of SEQ ID NO: 7, a heavy chain CDR3 comprising the amino acid sequence of SEQ ID NO: 8, and a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11;

(b) a heavy chain variable domain comprising the amino acid sequence of SEQ ID NO: 3 and a light chain variable domain comprising the amino acid sequence of SEQ ID NO: 4; or (c) a heavy chain comprising the amino acid sequence of SEQ ID NO: 1 or SEQ ID NO: 12 and a light chain comprising the amino acid sequence of SEQ ID NO: 2.

2. The method of claim 1, wherein the formulation is administered to the patient once a week, once every two weeks, or once every four weeks.

3. The method of claim 1, wherein the formulation is administered to the patient subcutaneously, intramuscularly, or intravenously.

4. The method of claim 1, wherein the patient suffers from Sjögren's syndrome.

5. The method of claim 1, wherein the patient suffers from dermatomyositis.

6. The method of claim 1, wherein the patient suffers from systemic lupus erythematosus.

* * * * *

SEQUENCE LISTING

<160> NUMBER OF SEQ ID NOS: 12

<210> SEQ ID NO 1
<211> LENGTH: 442
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Arg Gln Leu Tyr Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
                180                 185                 190

Gly Thr Gln Thr Tyr Thr Cys Asn Val Asp His Lys Pro Ser Asn Thr

-continued

```
                195                 200                 205
Lys Val Asp Lys Thr Val Glu Arg Lys Cys Cys Val Glu Cys Pro Pro
210                 215                 220
Cys Pro Ala Pro Pro Val Ala Gly Pro Ser Val Phe Leu Phe Pro Pro
225                 230                 235                 240
Lys Pro Lys Asp Thr Leu Met Ile Ser Arg Thr Pro Glu Val Thr Cys
            245                 250                 255
Val Val Val Asp Val Ser His Glu Asp Pro Glu Val Gln Phe Asn Trp
            260                 265                 270
Tyr Val Asp Gly Val Glu Val His Asn Ala Lys Thr Lys Pro Arg Glu
            275                 280                 285
Glu Gln Phe Asn Ser Thr Phe Arg Val Val Ser Val Leu Thr Val Val
            290                 295                 300
His Gln Asp Trp Leu Asn Gly Lys Glu Tyr Lys Cys Lys Val Ser Asn
305                 310                 315                 320
Lys Gly Leu Pro Ala Pro Ile Glu Lys Thr Ile Ser Lys Thr Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
370                 375                 380
Asn Tyr Lys Thr Thr Pro Pro Met Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
Gln Lys Ser Leu Ser Leu Ser Pro Gly Lys
                435                 440

<210> SEQ ID NO 2
<211> LENGTH: 214
<212> TYPE: PRT
<213> ORGANISM: Homo sapiens

<400> SEQUENCE: 2

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
                20                  25                  30
Leu Ala Trp Phe Gln Gln Lys Pro Gly Gln Ala Pro Arg Pro Leu Ile
            35                  40                  45
Tyr Asp Ala Ser Thr Arg Ala Thr Gly Val Pro Ala Arg Phe Ser Gly
        50                  55                  60
Ser Gly Ser Gly Thr Asp Phe Thr Leu Thr Ile Ser Ser Leu Gln Ser
65                  70                  75                  80
Glu Asp Phe Ala Val Tyr Tyr Cys Gln Gln Tyr Asp Asn Trp Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 116
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
                100                 105                 110

Thr Val Ser Ser
        115
```

<210> SEQ ID NO 4
<211> LENGTH: 107
<212> TYPE: PRT
<213> ORGANISM: Homo sapiens

<400> SEQUENCE: 4

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Phe Gln Gln Lys Pro Gly Gln Ala Pro Arg Pro Leu Ile
            35                  40                  45

Tyr Asp Ala Ser Thr Arg Ala Thr Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
                100                 105
```

<210> SEQ ID NO 5
<211> LENGTH: 5
<212> TYPE: PRT
<213> ORGANISM: Homo sapiens

<400> SEQUENCE: 5

Arg Tyr Gly Ile Ser
1               5

<210> SEQ ID NO 6
<211> LENGTH: 17
<212> TYPE: PRT
<213> ORGANISM: Homo sapiens

<400> SEQUENCE: 6

Trp Ile Ser Thr Tyr Ser Gly Asn Thr Asn Tyr Ala Gln Lys Leu Gln
1               5                   10                  15

Gly

<210> SEQ ID NO 7
<211> LENGTH: 16
<212> TYPE: PRT
<213> ORGANISM: Homo sapiens

<400> SEQUENCE: 7

Trp Ile Ser Thr Tyr Ser Gly Asn Thr Asn Tyr Ala Gln Lys Leu Gln
1               5                   10                  15

<210> SEQ ID NO 8
<211> LENGTH: 7
<212> TYPE: PRT
<213> ORGANISM: Homo sapiens

<400> SEQUENCE: 8

Arg Gln Leu Tyr Phe Asp Tyr
1               5

<210> SEQ ID NO 9
<211> LENGTH: 11
<212> TYPE: PRT
<213> ORGANISM: Homo sapiens

<400> SEQUENCE: 9

Arg Ala Ser Gln Ser Val Ser Ser Asn Leu Ala
1               5                   10

<210> SEQ ID NO 10
<211> LENGTH: 7
<212> TYPE: PRT
<213> ORGANISM: Homo sapiens

<400> SEQUENCE: 10

Asp Ala Ser Thr Arg Ala Thr
1               5

<210> SEQ ID NO 11
<211> LENGTH: 9
<212> TYPE: PRT
<213> ORGANISM: Homo sapiens

<400> SEQUENCE: 11

Gln Gln Tyr Asp Asn Trp Pro Leu Thr
1               5

<210> SEQ ID NO 12
<211> LENGTH: 441
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380
```

```
Asn Tyr Lys Thr Thr Pro Pro Met Leu Asp Ser Asp Gly Ser Phe Phe
385                 390             395                 400

Leu Tyr Ser Lys Leu Thr Val Asp Lys Ser Arg Trp Gln Gln Gly Asn
            405             410                 415

Val Phe Ser Cys Ser Val Met His Glu Ala Leu His Asn His Tyr Thr
            420             425                 430

Gln Lys Ser Leu Ser Leu Ser Pro Gly
        435             440
```